(12) United States Patent
Hickmann et al.

(10) Patent No.: US 10,913,704 B2
(45) Date of Patent: Feb. 9, 2021

(54) 2,3,7-TRIMETHYLOCT-6-ENYL ACETATE AND 3,7-DIMETHYL-2-METHYLENE-OCT-6-ENYL ACETATE AND DERIVATIVES THEREOF AND THEIR USE AS AROMA CHEMICALS

(71) Applicant: BASF SE, Ludwigshafen am Rhein (DE)

(72) Inventors: Volker Hickmann, Ludwigshafen am Rhein (DE); Stefan Ruedenauer, Lampertheim (DE); Ralf Pelzer, Lampertheim (DE); Vijay Narayanan Swaminathan, Ludwigshafen am Rhein (DE); Shrirang Hindalekar, Mumbai (IN); Nitin Gupte, Mumbai (IN); Sadanand Ardekar, Mumbai (IN); Mileen Kadam, Mumbai (IN)

(73) Assignee: BASF SE

( * ) Notice: Subject to any disclaimer, the term of this patent is extended or adjusted under 35 U.S.C. 154(b) by 0 days.

(21) Appl. No.: 16/611,120

(22) PCT Filed: May 4, 2018

(86) PCT No.: PCT/EP2018/061457
§ 371 (c)(1),
(2) Date: Nov. 5, 2019

(87) PCT Pub. No.: WO2018/206415
PCT Pub. Date: Nov. 15, 2018

(65) Prior Publication Data
US 2020/0190014 A1 Jun. 18, 2020

(30) Foreign Application Priority Data

May 6, 2017 (IN) .............................. 201721016017
Jun. 23, 2017 (EP) ..................................... 17177666

(51) Int. Cl.
*A61K 8/18* (2006.01)
*A61Q 13/00* (2006.01)
*A61K 8/00* (2006.01)
*C07C 69/145* (2006.01)
*C07C 67/40* (2006.01)
*C11B 9/00* (2006.01)

(52) U.S. Cl.
CPC ............ *C07C 69/145* (2013.01); *C07C 67/40* (2013.01); *C11B 9/0019* (2013.01)

(58) Field of Classification Search
USPC .......................................... 512/27, 26, 25, 1
See application file for complete search history.

(56) References Cited

U.S. PATENT DOCUMENTS

| | | | |
|---|---|---|---|
| 3,463,818 A | 8/1969 | Blumenthal | |
| 10,106,477 B2 | 10/2018 | Fenlon et al. | |
| 10,315,975 B2 | 6/2019 | Strautmann et al. | |
| 2008/0064624 A1* | 3/2008 | Narula | A61Q 13/00 512/20 |
| 2018/0134680 A1 | 5/2018 | Siegel et al. | |
| 2018/0273458 A1 | 9/2018 | Strautmann et al. | |
| 2019/0169108 A1 | 6/2019 | Hickmann et al. | |

OTHER PUBLICATIONS

Chemiker Zeitung, [The Chemists Journal], vol. 97, No. 2, pp. 67-73.
"Working with Hazardous Chemicals", Organic Syntheses, 1941, vol. 1, p. 330.
"Working with Hazardous Chemicals", Organic Syntheses, 1925, vol. 4, p. 39.
International Preliminary Report on Patentability for PCT/EP2018/061457 dated Jul. 30, 2018.

* cited by examiner

*Primary Examiner* — Jessica Whiteley
(74) *Attorney, Agent, or Firm* — Faegre Drinker Biddle & Reath LLP

(57) ABSTRACT

The present invention relates to 2,3,7-Trimethyloct-6-enyl acetate and 3,7-dimethyl-2-methylene-oct-6-enyl acetate and derivatives thereof and their use as aroma chemicals.

20 Claims, No Drawings

2,3,7-TRIMETHYLOCT-6-ENYL ACETATE AND 3,7-DIMETHYL-2-METHYLENE-OCT-6-ENYL ACETATE AND DERIVATIVES THEREOF AND THEIR USE AS AROMA CHEMICALS

CROSS-REFERENCE TO RELATED APPLICATIONS

This application is a national stage application (under 35 U.S.C. § 371) of PCT/EP2018/061457, filed May 4, 2018, which claims benefit of Indian Application No. 201721016017, filed May 6, 2017, and European Application No. 17177666.9, filed June 2017 all of which are incorporated herein by reference in their entirety.

BACKGROUND

Despite a large number of existing aroma chemicals (fragrances and flavorings), there is a constant need for new components in order to be able to satisfy the multitude of properties desired for extremely diverse areas of application. These include, firstly, the organoleptic properties, i.e. the compounds should have advantageous odiferous (olfactory) or gustatory properties. Furthermore, aroma chemicals should, also have additional positive secondary properties, such as e.g. an efficient preparation method, the possibility of providing better sensory profiles as a result of synergistic effects with other fragrances, a higher stability under certain application conditions, a higher extendibility, a better staying power, etc.

U.S. Pat. No. 3,463,818 relates to a process for producing a-methylene- and a-methyl-aldehydes and -alcohols and derivatives thereof, useful as perfumes; and to the products so produced.

US2008/0064624 relates cyclohexyl, cyclopentyl and acyclic ester compounds and the incorporation and use of the compounds as fragrance material. US2008/0064624 discloses 6-octen-1-ol,3,7-dimethyl-2-methylene acetate. This compound is synthesized by esterification of 2-methylene-3,7-dimethyl-6-octen-1-ol and acetic anhydride and only a racemic mixture is obtained.

It is known that esters of higher alcohols may be prepared by reacting these with carbonyl halides or with carboxylic anhydrides. A disadvantage of the reaction with carbonyl halides is that hydrohalic acids are formed in the reaction thereof, which generally lead to problems of corrosion, and elimination of water in the case of tertiary alcohols and thereby causing numerous polymerizations. The disadvantage in the reaction with carboxylic anhydrides is that equimolar amounts of the corresponding carboxylic acid are formed in the reaction mixture, which must be removed in the work-up and the reuse thereof can be technically complex.

It is further known that acetic acid esters may be prepared by reacting hydroxyl group-containing compounds with ketene. Various catalysts may be used for the reaction of hydroxyl group-containing compounds with ketene, e.g. Brønsted acids such as sulfuric acid, p-toluenesulfonic acid, phosphoric acid, potassium hydrogen sulfate or Lewis acids such as boron trifluoride or boron trifluoride etherate. However, various disadvantages have also been described for the catalyzed reaction of ketenes. For instance, acidic catalysts may cause corrosion in metal apparatuses or lead to the undesired formation of resin-like impurities. In addition, it can often be difficult to remove them again from the reaction mixture.

Methods and devices for preparing ketene are described, for example, in Organic Syntheses, Coll. Vol. 1, p. 330 (1941) and Vol. 4, p. 39 (1925) and in the Chemiker Zeitung [The Chemists Journal] 97, No. 2, pages 67 to 73 (1979).

Aroma substances and fragrances have a high profile of requirements. Even minimal by-products may negatively impact the quality of the aroma substance or fragrance. Moreover, methods for preparing aroma substances and fragrances which only comprise few method steps and require less feedstocks are desirable for environmental reasons.

The object of the present invention is to provide new aroma chemicals with advantageous properties. These aroma chemicals should specifically have pleasant odiferous properties.

Moreover, the object of the present invention is to provide a method for preparing acetate compounds and their derivatives which have the advantages mentioned above over the prior art. It has now been found, surprisingly, that this object is achieved by the method according to the invention.

SUMMARY OF THE INVENTION

The invention provides compounds of the formula (I)

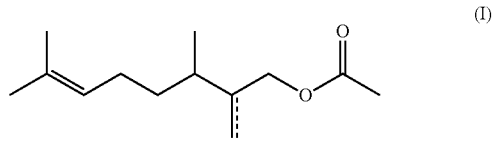

wherein $\equiv\equiv\equiv$ is a single or a double bond, selected from the compound of the formula (I.a) and the compound of formula (I.b)

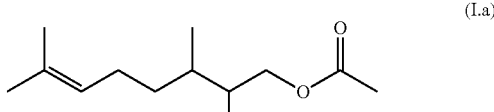

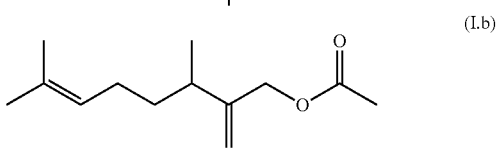

and the stereo isomers thereof.

In particular, the invention provides compounds of the formula (I)

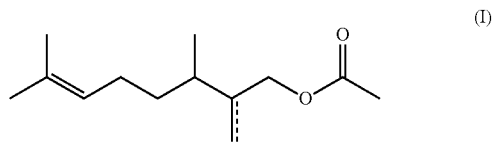

wherein
═══ is a single or a double bond,
selected from the compound of the formula (I.a)

(I.a)

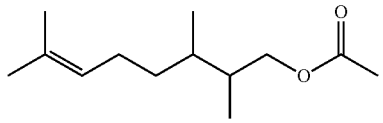

the compound of formula (I.b)

(I.b)

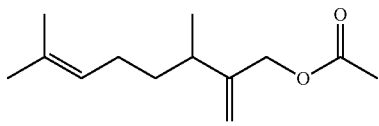

and stereo isomers thereof and mixtures thereof, with the proviso that compound (I.b) is not a racemate.

In a further embodiment A compound of the formula (I)

(I)

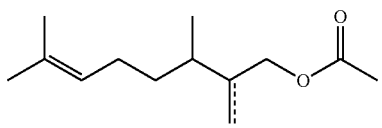

wherein
═══ is a single or a double bond,
selected from
the compound of the formula (I.a)

(I.a)

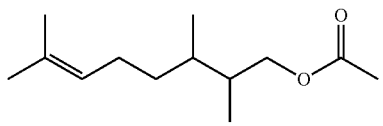

the compound of formula (I.b)

(I.b)

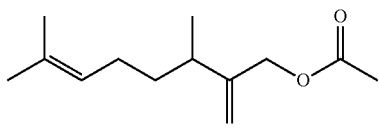

and the stereo isomers thereof.

In a preferred embodiment, the invention provides compounds selected from the compounds of formulae (I.a1), (I.a2), (I.a3), (I.a4) and mixtures thereof.

(I.a1)

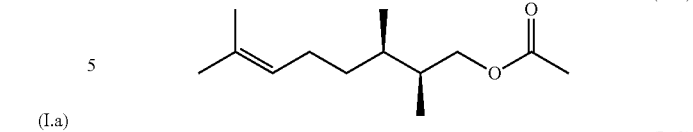

(I.a2)

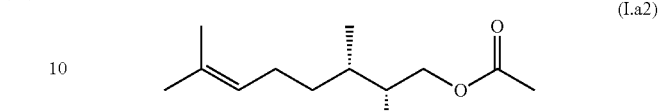

(I.a3)

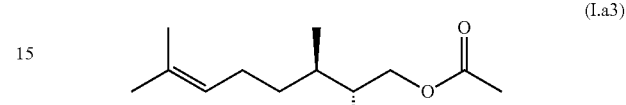

(I.a4)

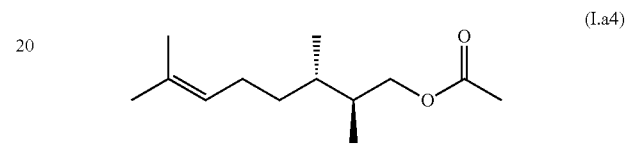

In another preferred embodiment, the invention provides compounds selected from the compounds of formulae (I.b1), (I.b2) and mixtures thereof, preferably one compound (I.b1) or (I.b2) is present in an amount of at least 60% by weight, based on the total weight of compound (I.b1) and (I.b2).

(I.b1)

(I.b2)

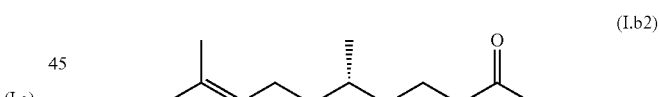

The invention further provides compositions comprising at least two compounds selected from the compounds the formula (I). Preferably the compositions comprising at least two compounds selected from compounds of the formulae (I.a1), (I.a2), (I.a3) (I.a4), (I.b1) and (I.b2) with the proviso that a composition consists only of the racemate of compound of (I.b1) and (I.b2) is excluded.

In a preferred embodiment the compositions comprising at least two compounds selected from compounds of the formulae (I.a1), (I.a2), (I.a3) and (I.a4).

In another preferred embodiment the compositions comprising at least two compounds selected from compounds of the formulae (I.b1) and (I.b2), preferably one compound (I.b1) or (I.b2) is present in an amount of at least 60% by weight, based on the total weight of compound (I.b1) and (I.b2).

The invention further provides methods for preparing compounds of the formula (I.a),

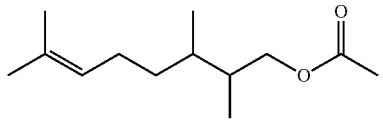
(I.a)

comprising the steps of
a) providing a compound of the formula (II.a),

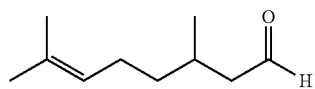
(II.a)

b) subjecting the compound of the formula (II.a) to an aldol condensation reaction with formaldehyde to obtain a compound of the formula (II.b)

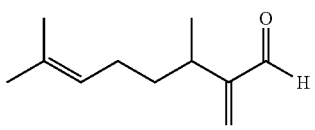
(II.b.)

c11) subjecting the compound of the formula (II.b) obtained in step b) to a hydrogenation reaction to obtain a compound of the formula (II.c)

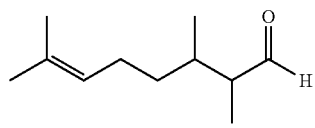
(II.c)

c12) reacting the compound of the formula (II.c) with a reducing agent to obtain a compound of the formula (II.d)

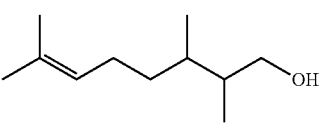
(II.d)

c13) subjecting the compound of the formula (II.d) to an esterification reaction using ethenone to obtain the compound of the formula (I.a).

The invention further provides methods for preparing compounds of the formula (I.b),

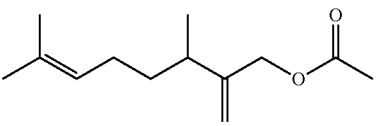
(I.b)

comprising the steps of
a) providing a compound of the formula (II.a),

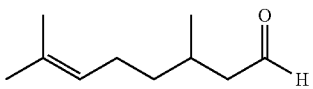
(II.a)

b) subjecting the compound of the formula (II.a) to an aldol condensation reaction with formaldehyde to obtain a compound of the formula (II.b)

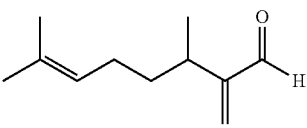
(II.b.)

c21) reacting the compound of the formula (II.b) obtained in step b) with a reducing reaction to obtain a compound of the formula (II.e),

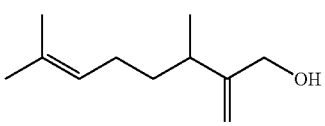
(II.e)

c22) subjecting the compound of the formula (II.e) to an esterification reaction using ethenone to obtain the compound of the formula (I.b).

The invention further provides a use of a compound of the formula (I) selected from compounds of formulae (I.a) and (I.b) as defined above as aroma chemical. The invention further provides a use of a composition as defined above comprising at least two compounds selected from the compound of the formula (I), which are preferably selected from the compounds of the formulae (I.a1), (I.a2), (I.a3), (I.a4), (I.b1), and (I.b2) as aroma chemical.

The use of a composition as defined above comprising at least two compounds, which are selected from the compounds of the formulae (I.a1), (I.a2), (I.a3) and (I.a4) as aroma chemical is preferred.

In another embodiment the use of a composition as defined above comprising at least two compounds, which are selected from the compounds of the formulae (I.b1), and (I.b2) as aroma chemical is preferred.

The invention further provides a use of a compound selected from compounds of the formulae (II.a), (II.b), (II.c), (II.d), and (II.e) as aroma chemical. The invention further provides a use of a composition of at least two compounds selected from compounds of the formulae (II.a), (II.b), (II.c), (II.d), and (II.e), as aroma chemical.

The invention further provides aroma substances and/or fragrance compositions comprising
i) at least a compound of the formula (I) selected from compounds of formulae (I.a) and (I.b) or a composition comprising at least two compounds selected from the compounds of formula (I),
ii) optionally at least one further aroma chemical different from the component i), and
iii) optionally at least one diluent,
with the proviso that the composition comprises at least one component ii) or iii).

The compounds of formulae (I) are selected from compounds of formulae (I.a) and (I.b). Preferably the compounds of formula (I) are selected from the compounds of the formulae (I.a1), (I.a2), (I.a3), (I.a4), (I.b1), and (I.b2).

A perfumed or fragranced product comprising at least a compound of the formula (I) selected from compounds of formulae (I.a) and (I.b) or a composition comprising at least two compounds selected from the compounds of formula (I), which are preferably selected from the compounds of the formulae (I.a1), (I.a2), (I.a3), (I.a4), (I.b1), and (I.b2).

A method for scenting a product, particularly for imparting and/or enhancing an odor or flavor, in which at least a compound of the formula (I) selected from compounds of formulae (I.a) and (I.b) or a composition comprising at least two compounds selected from the compounds of formula (I), which are preferably selected from the compounds of the formulae (I.a1), (I.a2), (I.a3), (I.a4), (I.b1), and (I.b2) is used.

DESCRIPTION OF THE INVENTION

The invention has the following advantages:
The compounds exhibit advantageous aroma properties.
The compounds are obtainable on industrial scale and in simple reactions.
The compounds are easily accessible via an effective synthesis route.

In the context of the present invention, the chemical structure formulas that do not explicitly show a specific stereochemical orientation usually mean all possible stereo isomers and mixtures thereof, unless indicated otherwise. For example, the formula (I) represents the isomers of formulae (I.a1), (I.a2), (I.a3), and (I.a4) and the formula (II.a) represents the isomers of formulae (II.a1) and (II.a2).

Compounds of Formula (I)

The invention provides compounds of formula (I) as defined herein, wherein $\;=\;$ is a single or a double bond.

The compounds of formula (I) are selected from compounds of the formula (I.a) and (I.b) and the stereoisomers of the compounds of formulae (I.a) and (I.b), with the proviso that compounds of formula (I.b) is not a racemate.

In this context of the invention the compounds of formulae (I.a) and (I.b) encompass the stereoisomers (I.a1), (I.a2), (I.a3), (I.a4), (I.b1) and (I.b2). Each stereoisomer has preferably a purity of at least 70%, more preferably of at least 80%, especially at least 95%.

In a special embodiment the compounds of formula (I) are selected from compounds of the formula (I.a) the stereoisomers thereof.

In the context of the invention mixtures of the stereoisomers encompass mixtures of different ratio of (I.a1), (I.a2), (I.a3), (I.a4), (I.b1) and (I.b2), wherein a mixture that contains only (I.b1) and (I.b2) in an ratio of 50:50 is excluded.

The stereoisomers of compounds of the formula (I.a) are selected from the compounds of the formulae (I.a1), (I.a2), (I.a3), and (I.a4).

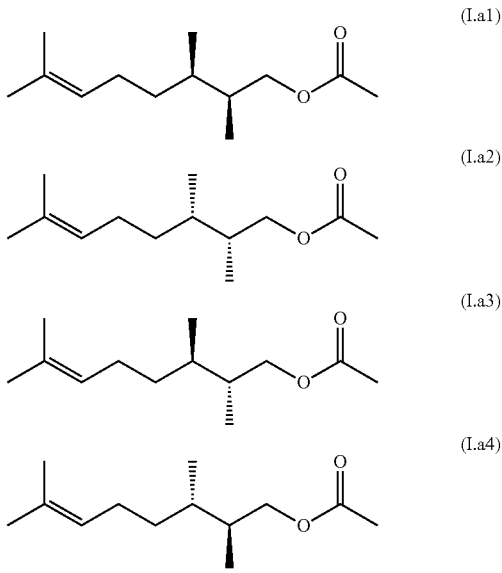

The compounds (I.a1) and (I.a2) can be named as syn-isomers and/or syn-diastereomers. The compounds (I.a3) and (I.a4) can be named as trans-isomers and/or anti-diastereomers. Similar applies for similar isomers.

The stereo isomers of compounds of the formula (I.b) are selected from the compounds of the formulae (I.b1) and (I.b2).

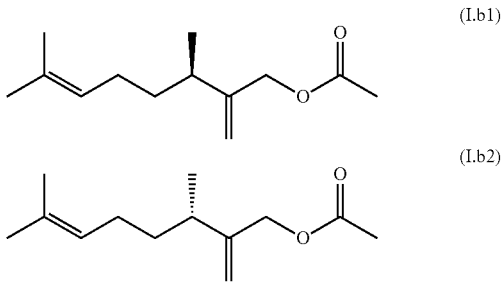

Compositions comprising at least two compounds selected from the compounds of formula (I).

The invention provides compositions comprising at least two compounds selected from the compounds of the formula (I). Thus, the invention provides compositions comprising at least two compounds selected from the compounds of the formulae (I.a1), (I.a2), (I.a3), (I.a4), (I.b1), and (I.b2).

In a preferred embodiment, the compositions according to the invention comprise at least two compounds selected from the compounds of the formulae (I.a1), (I.a2), (I.a3), and (I.a4). Preferably, those compositions comprise the compounds of formulae (I.a1), (I.a2), (I.a3), and (I.a4).

In one variant, those compositions preferably comprise the compounds of the formulae (I.a1) and (I.a2) in ratios of 30:70 to 70:30, preferably 35:65 to 65:35, more preferably 45:55 to 55:45, even more preferably 49:51 to 51:49.

In another variant, those compositions preferably comprise the compounds of the formulae (I.a3) and (I.a4) in ratios of 30:70 to 70:30, preferably 35:65 to 65:35, more preferably 45:55 to 55:45, even more preferably 49:51 to 51:49.

In a preferred variant, those compositions comprise the compounds of the formulae (I.a1) and (I.a2) in ratios of 30:70 to 70:30, preferably 35:65 to 65:35, more preferably 45:55 to 55:45, even more preferably 49:51 to 51:49 and the compounds of the formulae (I.a3) and (I.a4) in ratios of 30:70 to 70:30, preferably 35:65 to 65:35, more preferably 45:55 to 55:45, even more preferably 49:51 to 51:49.

In another variant, those compositions preferably comprise the compound of the formula (I.a1) in an amount of more than 70%, preferably at least 80%, more preferably at least 90%, and even more preferably more than 95%, based on the total amount of compounds (I.a1) and (I.a2).

In another variant, those compositions preferably comprise the compound of the formula (I.a3) in an amount of more than 70%, preferably at least 80%, more preferably at least 90%, and even more preferably more than 95%, based on the total amount of compounds (I.a3) and (I.a4).

In another variant, those compositions preferably comprise the compound of the formula (I.a1) in an amount of more than 70%, preferably at least 80%, more preferably at least 90%, and even more preferably more than 95%, based on the total amount of compounds (I.a1) and (I.a2), and the compound of the formulae (I.a3) in an amount of more than 70%, preferably at least 80%, more preferably at least 90%, and even more preferably more than 95%, based on the total amount of compounds (I.a3) and (I.a4).

In another variant, those compositions preferably comprise the compound of the formula (I.a2) in an amount of more than 70%, preferably at least 80%, more preferably at least 90%, and even more preferably more than 95%, based on the total amount of compounds (I.a1) and (I.a2).

In another variant, those compositions preferably comprise the compound of the formula (I.a4) in an amount of more than 70%, preferably at least 80%, more preferably at least 90%, and even more preferably more than 95%, based on the total amount of compounds (I.a3) and (I.a4).

In another variant, those compositions preferably comprise the compound of the formula (I.a2) in an amount of more than 70%, preferably at least 80%, more preferably at least 90%, and even more preferably more than 95%, based on the total amount of compounds (I.a1) and (I.a2), and the compound of the formulae (I.a4) in an amount of more than 70%, preferably at least 80%, more preferably at least 90%, and even more preferably more than 95%, based on the total amount of compounds (I.a3) and (I.a4).

In another preferred embodiment, the compositions according to the invention comprise compounds of the formulae (I.b1) and (I.b2), with the proviso that a composition that consists only of the racemate of compound of (I.b1) and (I.b2) is excluded.

In one variant, those compositions preferably comprise the compound of the formulae (I.b1) in an amount of more than 70%, preferably at least 80%, more preferably at least 90%, and even more preferably more than 95%, based on the total amount of compounds (I.b1) and (I.b2).

In another variant, those compositions preferably comprise the compound of the formulae (I.b2) in an amount of more than 70%, preferably at least 80%, more preferably at least 90%, and even more preferably more than 95%, based on the total amount of compounds (I.b1) and (I.b2).

In a preferred embodiment the ratio of compound (I.b1):(I.b2) in those compositions are 75:25 to 95:5, preferably 80:20 to 90:10. In another preferred embodiment the ratio of compound (I.b2):(I.b1) in those compositions are 75:25 to 95:5, preferably 80:20 to 90:10.

Methods for Preparing Compounds of the Formula (I)

The invention further provides methods for preparing a compound of the formula (I) comprising the steps of a) providing a compound of the formula (II.a), b) subjecting the compound of the formula (II.a) to an aldol condensation reaction with formaldehyde to obtain a compound of the formula (II.b)

and either further comprising the steps of c11) subjecting the compound of the formula (II.b) obtained in step b) to a hydrogenation reaction to obtain a compound of the formula (II.c)

c12) reacting the compound of the formula (II.c) with a reducing agent to obtain a compound of the formula (II.d)

c13) subjecting the compound of the formula (II.d) to an esterification reaction using ethenone to obtain the compound of the formula (I.a), or comprising the steps of c21) reacting the compound of the formula (II.b) obtained in step b) with a reducing reaction to obtain a compound of the formula (II.e), c22) subjecting the compound of the formula (II.e) to an esterification reaction using ethenone to obtain the compound of the formula (I.b).

Step a)

The methods for preparing a compound of the formula (I) comprise the step of a) providing a compound of the formula (II.a).

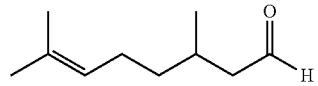

(II.a)

The compound of formula (II.a) is commercially available as "citronellal". The compound of formula (II.a) has two stereo isomers, namely the compound of the formula (II.a1), which is known as (R)-(+)-citronellal and the compound of the formula (II.a2), which is known as (S)-(−)-citronellal.

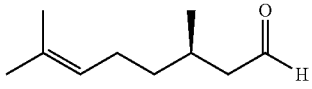

(II.a1)

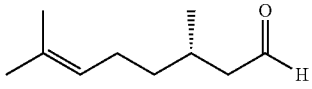

(II.a2)

The (S)-(−)-citronellal is available under CAS 5949-05-3, the (R)-(+)-citronellal is available under CAS 2385-77-5, and a (+−)-citronellal is available under CAS 106-23-0.

The compound of formula (II.a) represents both the individual isomer as well as a mixture thereof.

Step b)

The methods for preparing a compound of the formula (I) further comprise the step of b) subjecting the compound of the formula (II.a) to an aldol condensation reaction with formaldehyde to obtain a compound of the formula (II.b)

The compound of formula (II.b) has two stereo isomers, namely the compounds of the formulae (II.b1) and (II.b2).

For step b), suitable aldol condensation reactions are known to skilled persons. Usually, the aldol condensation reaction in step b) is carried out using aqueous formaldehyde. The reaction is usually carried out at temperatures in the range of 10 to 60° C. using isopropanol/water as solvent.

Step c11)

The methods for preparing compound of the formula (I.a) comprise the steps of a) providing a compound of the formula (II.a), b) subjecting the compound of the formula (II.a) to an aldol condensation reaction with formaldehyde to obtain a compound of the formula (II.b), and c11) subjecting the compound of the formula (II.b) obtained in step b) to a hydrogenation reaction to obtain a compound of the formula (II.c)

The compound of formula (II.c) has four stereo isomers, namely the compounds of the formulae (II.c1), (II.c2), (II.c3), and (II.c4).

For step c11), suitable hydrogenation reactions are known to skilled persons. Usually, the hydrogenation reaction in step c11) is carried out using molecular hydrogen in the presence of a catalyst. Preferably, palladium on carbon, Pd/C, is used as catalyst in step c11).

Step c12)

The methods for preparing compound of the formula (I.a) further comprise the step of c12) reacting the compound of the formula (II.c) with a reducing agent to obtain a compound of the formula (II.d)

The compound of formula (II.d) has four stereo isomers, namely the compounds of the formulae (II.d1), (II.d2), (II.d3), and (II.d4).

For step c12), suitable reducing agents are known to skilled persons. Usually, the reaction in step c12) is carried out in using a reducing agent which is selected from hydride compounds.

Suitable hydride compounds for the reaction in step c12) are for example covalent hydrides, ionic hydrides, metallic hydrides, and transition metal hydride complexes. Preferably, the hydride compound is selected from boron hydrides, and aluminium hydrides. In particular, the hydride compound is selected from sodium borohydride (NaBH$_4$), diisobutylaluminium hydride (DIBAL), sodium bis(2-methoxyethoxy)-aluminiumhydride (Red-Al®) and lithium aluminium hydride (LiAlH$_4$).

With borohydrides, the reaction in step c12) is carried out in an organic solvent such as methanol at temperatures in the range of −20 to +30° C. With aluminium hydrides, the reaction is carried out at temperatures in the range of −30 to +80° C. in etheral solvents such as diethyl ether, methyl tert-butyl ether (MTBE), tetrahydrofuran (THF), 2-methyl-tetrahydrofuran (Me-THF) or toluene. Common reaction conditions are known to persons skilled in the art.

Step c13)

The methods for preparing compound of the formula (I.a) further comprise the step of c13) subjecting the compound of the formula (II.d) to an esterification reaction using ethenone to obtain the compound of the formula (I.a).

For step c13), suitable reaction conditions for esterification reactions using ethenone are known to persons skilled in the art.

Ethenone is preferably generated by high temperature pyrolysis of acetone or acetic acid at temperatures generally higher than 650° C. The temperature is preferably in the range from 650 to 1000° C., particularly preferably from 700 to 900° C.

In a specific embodiment, ethenone is prepared under reduced pressure. The pressure is preferably in the range from about 100 to 900 mbar, particularly preferably from 300 to 500 mbar, especially from 350 to 450 mbar. In an alternative embodiment, ethenone is prepared at ambient pressure. In this case, the pressure is preferably in the range from about 950 to 1050 mbar.

Since ethenone is an exceptionally reactive compound which has a strong tendency to dimerize forming diketenes, the ethenone compound is used in the method according to the invention which has preferably been prepared only briefly beforehand. The method according to the invention is rendered particularly advantageous when using ethenone which has been prepared directly prior to the reaction in the method according to the invention, for example, by thermal cleavage of acetone, acetic acid or acetic anhydride.

In a first variant of the method according to the invention, the ethenone is introduced into the reaction mixture below the liquid surface such that it sparges the reaction mixture. The ethenone is advantageously fed into the reaction mixture under intensive stirring so that no ethenone substantially converts into the gas phase in relatively large amounts. The pressure of the ketene must be sufficiently high in order to overcome the hydrostatic pressure of the reaction mixture above the ethenone input, optionally supported by a stream of inert gas, e.g. nitrogen.

The ethenone can be introduced via any suitable devices. Good distribution and rapid mixing are important here. Suitable devices are, for example, sparging lances which may be fixed in position or preferably nozzles. The nozzles can be provided at or near the bottom of the reactor. For this purpose, the nozzles may be configured as openings from a hollow chamber surrounding the reactor. However, preference is given to using immersed nozzles with suitable feed lines. A plurality of nozzles can, for example, be arranged in the form of a ring. The nozzles may point upward or downward. The nozzles preferably point obliquely downward.

In a second variant of the method according to the invention, the ethenone is prepared under reduced pressure and reacted under reduced pressure with the alcohol compound. The pressure during the preparation and reaction of the ethenone is preferably in the range from about 100 to 900 mbar, particularly preferably from 300 to 500 mbar, especially from 350 to 450 mbar.

Methods and apparatuses for preparing ethenone are described, for example, in Organic Syntheses, Coll. Vol. 1, p. 330 (1941) and Vol. 4, p. 39 (1925) and in Chemiker Zeitung [The Chemists Journal] 97, No. 2, pages 67 to 73 (1979).

An excess of the ethenone can lead to undesired side reactions. Therefore, the reaction of the compound of the general formula (II.d) with the ketene is preferably carried out using at most equimolar amounts of the ketene. The compound of formula (II.d) is preferably reacted with the ketene in such a way that an accumulation of the ketene in the reaction mixture is avoided at all times in the reaction. The reaction of the compound of the formula (II.d) with the ketene preferably takes place in such a way that ketene is introduced into the reaction mixture until the conversion of compound of formula (II.d) is at least 90%, preferably at least 95%. The compound of the formula (II.d) is preferably subjected to a reaction with ketene at a temperature in the range of 0 to 150° C., preferably 40 to 120° C. and more preferably 80 to 100° C.

In a first preferred embodiment, the compound of the formula (II.d) is subjected to a reaction with the ketene in the absence of an added catalyst.

In a second preferred embodiment, the compound of the formula (A) is subjected to a reaction with the ketene in the presence of a catalyst. Preference is given to using at least one zinc salt as catalyst which may also be present as a hydrate or polyhydrate. Particular preference is given to using a zinc salt of a carboxylic acid as catalyst, especially a monocarboxylic acid having 1 to 18 carbon atoms or dicarboxylic acid having 2 to 18 carbon atoms. These include, e.g. zinc formate, zinc acetate, zinc propionate, zinc butyrate, zinc stearate, zinc succinate or zinc oxalate. Particular preference is given to zinc acetate. It is very advantageous in the method according to the invention that the catalysts generally only have to be used in very small amounts, which makes the method more cost-effective and facilitates the work-up of the reaction mixture. This applies in particular to using a zinc salt as catalyst. The catalyst is preferably used in an amount of 0.01 to 2% by weight, particularly preferably 0.02 to 0.5% by weight, based on the total amount of the compound (II.d).

To perform the reaction according to the invention, it is advantageous to proceed in such a way that said reaction is carried out in a suitable reaction vessel comprising, as essential components, a good stirring and/or mixing device, a metering device for ethenone, a heating device to start the reaction and to maintain the reaction temperature during the postreaction, a cooling device to remove the heat of reaction of the exothermic reaction and a vacuum pump. For an optimal reaction regime, it is advantageous to meter in the ketene such that it is never present in excess in the reaction mixture and that the reaction mixture is always thoroughly mixed. For an optimal reaction regime, it is further advantageous to avoid adding ketene too rapidly and to clearly determine the end of the reaction, e.g. by monitoring the reaction heat.

It is also possible to detect ethenone, for example, by IR spectroscopy by means of the characteristic carbonyl band.

By means of the method according to the invention, it is possible to prepare the compounds of the formula (II.d) in a technically simple manner in high purities and nevertheless in excellent yields and space-time yields. Since the reactants are essentially completely converted to products, the method according to the invention is characterized by a maximum atom economy.

Step c21)

The methods for preparing compound of the formula (I.b) comprise the steps of a) providing a compound of the formula (II.a), b) subjecting the compound of the formula (II.a) to an aldol condensation reaction with formaldehyde to obtain a compound of the formula (II.b), and c21) reacting the compound of the formula (II.b) obtained in step b) with a reducing agent to obtain a compound of the formula (II.e).

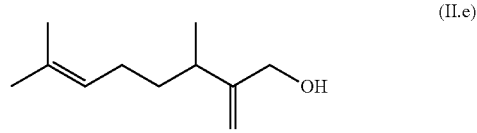

(II.e)

The compound of formula (II.e) has two stereo isomers, namely the compounds of the formulae (II.e1) and (II.e2).

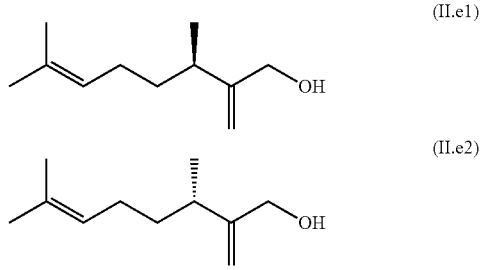

(II.e1)

(II.e2)

For step c21), suitable reaction conditions are known to skilled persons. Usually, the reaction in step c21) is carried out under those conditions mentioned herein for the reaction step c12). Thus, usually the reaction in step c21) is carried out in using a reducing agent which is selected from hydride compounds.

Suitable hydride compounds for the reaction in step c21) are for example covalent hydrides, ionic hydrides, metallic hydrides, and transition metal hydride complexes. Preferably, the hydride compound is selected from boron hydrides, and aluminium hydrides. In particular, the hydride compound is selected from sodium borohydride ($NaBH_4$), diisobutylaluminium hydride (DIBAL), sodium bis(2-methoxyethoxy)-aluminiumhydride (Red-Al®) and lithium aluminium hydride ($LiAlH_4$).

With borohydrides, the reaction in step c21) is carried out in an organic solvent such as methanol at temperatures in the range of −20 to +30° C. With aluminium hydrides, the reaction is carried out at temperatures in the range of −30 to +80° C. in etheral solvents such as diethyl ether, methyl tert-butyl ether (MTBE), tetrahydrofuran (THF), 2-methyl-tetrahydrofuran (Me-THF) or toluene. Common reaction conditions are known to persons skilled in the art.

Step c22)

The methods for preparing compound of the formula (I.b) further comprise the step of c22) subjecting the compound of the formula (II.e) to an esterification reaction using ethenone to obtain the compound of the formula (I.b).

For step c22), suitable reaction conditions for esterification reactions using ethenone are known to skilled persons. Usually, the reaction in step c22) is carried out under those conditions mentioned herein for the reaction step c13).

Thus, the features mentioned herein for the reaction step c13), thus for the reaction of the compound of formula (II.d) to the compound of formula (I.a), apply mutatis mutandis for the reaction step 22), thus for the reaction of the compound of the formula (II.e) to the compound of the formula (I.b)

Use as Aroma Chemical

An aroma chemical, also known as aroma compound, odorant, aroma, fragrance, or flavor, is a chemical compound that has a smell or odor. A chemical compound typically has a smell or odor when it is sufficiently volatile to be transported to the olfactory system, typically in the upper part of the nose.

The invention further provides a use of a compound of the formula (I) selected from compounds of formulae (I.a) and (I.b) as aroma chemical. Preferred compounds of the formula (I) are those mentioned herein.

The invention further provides a use of a composition comprising at least two compounds selected from the compounds of the formula (I), which are preferably selected from the compounds of the formulae (I.a1), (I.a2), (I.a3), (I.a4), (I.b1), and (I.b2) as aroma chemical. Preferred composition comprising at least two compounds selected from the compounds of the formula (I) are those mentioned herein.

The invention further provides a use of a compound selected from compounds of the formulae (II.a), (II.b), (II.c), (II.d), and (II.e) as aroma chemical. The invention further provides a use of a composition of at least two compounds selected from compounds of the formulae (II.a), (II.b), (II.c), (II.d), and (II.e), as aroma chemical. Preferred compounds of the formulae (II.a), (II.b), (II.c), (II.d), and (II.e) are those mentioned herein.

The compound of formula (I.a) as well as isomer mixtures of compounds of formula (I.a) have an aroma of herbaceous, green, technical, which disappears after 2-3 minutes, natural, fresh impression, floral, freesia, watery, sweet, pleasantly fresh and/or watery-ozone.

In a particular embodiment, the compositions comprising compounds of formula (I.a) comprise the syn-diastereomers (I.a1, I.a2) and anti-diastereomers (I.a3, I.a4) in a ratio of 48:52 to 68:32, preferably 56:44 to 60:40, whereas the main components are the syn-diastereomers (I.a1, I.a2). Such compositions have an aroma of herbaceous, green, technical, which disappears after 2-3 minutes, then, natural, fresh impression, slightly weak with an intensity of 2.

In particular, a racemic composition of syn-isomers (I.a1, I.a2) and anti-isomers (I.a3, I.a4) in the ratio of 58:42 has an aroma of herbaceous, green, technical, which disappears after 2-3 minutes, then, natural, fresh impression, slightly weak with an intensity of 2.

In a particular embodiment, the compositions comprising compounds of formula (I.a) comprise the syn-diastereomers (I.a1, I.a2) and anti-diastereomers (I.a3, I.a4) in a ratio of 12:88 to 32:68, preferably 20:80 to 24:76, whereas the main components are the anti-diastereomers (I.a3, I.a4). Such compositions have an aroma of floral, freesia, watery, sweet, pleasantly fresh, slightly weak with an intensity of 2.

In particular, a racemic composition of syn-isomers (I.a1, I.a2) and anti-isomers (I.a3, I.a4) in the ratio of 22:78 has an aroma of floral, freesia, watery, sweet, pleasantly fresh, slightly weak with an intensity of 2.

In a particular embodiment, the compositions comprising compounds of formula (I.a) comprise the syn-diastereomers (I.a1, I.a2) and anti-diastereomers (I.a3, I.a4) in a ratio of 72:28 to 92:8, preferably 80:20 to 84:16, whereas the main components are the syn-isomers (I.a1, I.a2). Such compositions have an aroma, after 5 minutes, of herbaceous, watery-ozone, weak.

In particular, a racemic composition of syn-isomers (I.a1, I.a2) and anti-isomers (I.a3, I.a4) in the ratio of 82:18 has an aroma, after 5 minutes, of herbaceous, watery-ozone, weak.

The compound of formula (I.b) as well as isomer mixtures of compounds of formula (I.b) have an aroma of floral, rose and/or waxy.

In a particular embodiment, the compositions comprising the compounds of the formulae (I.b1) and (I.b2) in ratios of 40:60 to 60:40, more particularly 45:55 to 55:45, even more particularly of 49:51 to 51:49. Such compositions have an aroma of floral, rose and/or waxy.

In a particular embodiment, the compositions comprising the compounds of the formulae (I.b1) and (I.b2) in ratios of 75:25 to 95:5, more particularly 80:20 to 90:10, even more particularly of 90:10 to 95:5. Such compositions have an aroma of floral and/or rose.

In a particular embodiment, the compositions comprising the compounds of the formula (I.b1). Such compositions have an aroma of floral, rose, citrus, sulphur-like and/or woody.

In a particular embodiment, the compositions comprising the compounds of the formula (I.b2). Such compositions have an aroma of floral and/or rose.

The compound of formula (II.b) as well as isomer mixtures of compounds of formula (II.b) have an aroma of citrus.

The compound of formula (II.c) as well as isomer mixtures of compounds of formula (II.c) have an aroma of rosy (room-filling), citrus, waxy.

The compound of formula (II.d) as well as isomer mixtures of compounds of formula (II.d) have an aroma of rose, geranium, honey, room-filling, good overall impression, fatty, green, woody, and/or herbaceous.

The compound of formula (II.e) as well as isomer mixtures of compounds of formula (II.e) have an aroma of rose.

A preferred embodiment of the invention thus provides the use of compound(s) of formula (I.a) for preparing a fragrance and/or aroma having a note of herbaceous, green, technical (which disappears after 2-3 minutes), natural, fresh impression, floral, freesia, watery, sweet, pleasantly fresh and/or watery-ozone.

Another preferred embodiment of the invention thus provides the use of compound(s) of formula (I.b) for preparing a fragrance and/or aroma having a note of floral, rose, citrus and/or woody.

Another preferred embodiment of the invention thus provides the use of compound(s) of formula (II.b) for preparing a fragrance and/or aroma having a note of citrus.

Another preferred embodiment of the invention thus provides the use of compound(s) of formula (II.c) for preparing a fragrance and/or aroma having a note of rosy (room-filling), citrus, waxy.

Another preferred embodiment of the invention thus provides the use of compound(s) of formula (II.d) for preparing a fragrance and/or aroma having a note of rose, geranium, honey, room-filling, good overall impression, fatty, green, woody, and/or herbaceous.

In a particular embodiment, the compositions comprising compounds of formula (II.d) comprise the syn-diastereomers (II.d1, II.d2) and anti-diastereomers (II.d3, II.d4) in a ratio of 91:9 to 99:1, preferably 93:7 to 97:3, whereas the main component are the syn-diastereomers (II.d1, II.d2). Such compositions have an aroma of geranium, rose, honey, room-filling, good overall impression with an intensity of 4.

In particular, a racemic composition of syn-isomers (II.d1, II.d2) and anti-isomers (II.d3, II.d4) in the ratio of 95:5 has an aroma of geranium, rose, honey, room-filling, good overall impression with an intensity of 4.

In another particular embodiment, the compositions comprising compounds of formula (II.d) comprise the syn-diastereomers (II.d1, II.d2) and anti-diastereomers (II.d3, II.d4) in a ratio of 11:89 to 31:69, preferably 19:81 to 23:77 whereas the main component are the anti-diastereomers (II.d3, II.d4). Such compositions have an aroma of geranium, rose, green, woody, room-filling, good overall impression with an intensity of 4.

In particular, a racemic composition of syn-isomers (II.d1, II.d2) and anti-isomers (II.d3, II.d4) in the ratio of 21:79 has an aroma of geranium, rose, green, woody, room-filling, good overall impression with an intensity of 4.

In another particular embodiment, the compositions comprising compounds of formula (II.d) comprise the syn-diastereomer (II.d1, II.d2) and the anti-diastereomers (II.d3, IId.4) in a ratio of 99:1 to 79:21, preferably 91:9 to 87:13, whereas the main component is component (II.d1). Such compositions have an aroma of geranium, rose, herbaceous, fatty, room-filling, good overall impression with an intensity of 4.

In particular, an enantiomerically enriched composition of syn-isomers (II.d1, II.d2) and anti-isomers (II.d3, II.d4) in the ratio of 89:11 has an aroma of geranium, rose, herbaceous, fatty, room-filling, good overall impression with an intensity of 4.

In another particular embodiment, the compositions comprising compounds of formula (II.d) comprise the syn-diastereomers (II.d1, II.d2) and anti-diastereomers (II.d3, II.d4) in a ratio of 13:87 to 33:67, preferably 21:79 to 25:75, whereas the main component is component (II.d3). Such compositions have an aroma of geranium, rose, green, herbaceous, room-filling, good overall impression with an intensity of 4.

In particular, an enantiomerically enriched composition of syn-isomers (II.d1, II.d2) and anti-isomers (II.d3, II.d4) in the ratio of 23:77 has an aroma of geranium, rose, green, herbaceous, room-filling, good overall impression with an intensity of 4.

Another preferred embodiment of the invention thus provides the use of compound(s) of formula (II.e) for preparing a fragrance and/or aroma having a note of rose.

The use as aroma chemical includes the use in various compositions such as compositions selected from perfumes, detergents and cleaning compositions, cosmetic agents, body care agents, hygiene articles, products for oral and dental hygiene, scent dispensers, fragrances and pharmaceutical agents.

Flavoring Compositions

The invention further provides a flavoring composition comprising a) at least one compound selected from compounds of formula (I), which are preferably selected from the compounds of the formulae (I.a1), (I.a2), (I.a3), (I.a4), (I.b1), and (I.b2), b) optionally at least one further aroma chemical different from the compounds of component a), and c) optionally at least one diluent, with the proviso that the composition comprises at least one of the components b) or c).

The invention further provides a flavoring composition comprising a) at least one compound selected from compounds of formula (I), which are preferably selected from the compounds of the formulae (II.a), (II.b), (II.c), (II.d), and (II.e),
b) optionally at least one further aroma chemical different from the compounds of component a), and
c) optionally at least one diluent,
with the proviso that the composition comprises at least one of the components b) or c).

In a preferred embodiment, the flavoring composition according to the invention comprises the component a) as the sole aroma chemical.

In a further preferred embodiment, the flavoring composition according to the invention comprises at least one further aroma chemical b) different from the compound of formula (I).

Further aroma chemicals, flavors and specifically odorants can be found e.g. in S. Arctander, Perfume and Flavor Chemicals, Vol. I and II, Montclair, N.J., 1969, self published or K. Bauer, D. Garbe and H. Surburg, Common Fragrance and Flavor Materials, $4^{th}$. Ed., Wiley-VCH, Weinheim 2001.

Preferably, the quantitative weight ratio of component a) to component b) is in a range from 100:1 to 1:100, particularly preferably from 50:1 to 1:50.

The aroma chemical or flavoring composition can optionally comprise at least one diluent c). Suitable diluents can be used individually or as a mixture of 2 or more than 2 diluents. Suitable diluents are those as are customarily used as solvents for flavoring compositions, fragrances, or flavors.

Preferably, the flavoring compositions comprise as diluents c), at least one compound which is liquid at 20° C. and 1013 mbar.

Preferably, the compounds of component a) have a solubility in component c) at 20° C. and 1013 mbar of at least 0.1 mg/ml, particularly preferably of at least 0.5 mg/ml. Preferably, if present, the compounds of component b) have a solubility in component c) at 20° C. and 1013 mbar of at least 0.1 mg/ml, particularly preferably of at least 0.5 mg/ml.

Component c) is preferably selected from aliphatic and cycloaliphatic monoalcohols, polyols, open-chain aliphatic ethers, cyclic ethers, polyol mono- and polyethers, esters and mixtures thereof.

Suitable aliphatic and cycloaliphatic monoalcohols are e.g. ethanol, n-propanol, isopropanol, n-butanol, sec-butanol, tert-butanol and cyclohexanol. Suitable polyols are ethylene glycol, propylene glycol, 1,2-butylene glycol, diethylene glycol, dipropylene glycol or glycerol. Suitable open-chain aliphatic ethers and cyclic ethers are e.g. diethyl ether, dipropyl ether, diisopropyl ether, methyl tert-butyl ether, tetrahydrofuran, tetrahydropyran, 1,4-dioxane or morpholine. Suitable polyol mono- and polyethers are e.g. ethylene glycol monomethyl ether, ethylene glycol dimethyl ether, ethylene glycol monoethyl ether, ethylene glycol diethyl ether, propylene glycol monoethyl ether, propylene glycol diethyl ether or diethylene glycol monoethyl ether. Suitable esters are ethyl acetate, methyl acetate, propyl acetate, isopropyl acetate, n-butyl acetate, sec-butyl acetate, tert-butyl acetate, isobutyl acetate, isoamyl acetate, ethyl butyrates, ethyl lactate, diethyl carbonate, ethylene carbonates, propylene carbonate, triethyl citrate, isopropyl myristate, diethyl phthalate, dialkyl esters of 1,2-cyclohexanedicarboxylic acid, specifically 1,2-cyclohexanedicarboxylic acid diisononyl ester (Hexamoll® DINCH, BASF SE), and the like.

Perfumed or Aromatized Product

The invention further provides a perfumed or aromatized product,
comprising an organoleptically effective amount of at least one compound selected from compounds of formula (I), which are preferably selected from the compounds of the formulae (I.a1), (I.a2), (I.a3), (I.a4), (I.b1), and (I.b2), and/or
comprising an organoleptically effective amount of at least one flavoring composition as defined herein.

A compound of formula (I) according to the invention and used according to the invention can be incorporated into a series of products and/or be applied to such products such as scent dispensers, fragrances perfumes, perfumes, detergents and cleaners, cosmetic compositions, bodycare compositions, hygiene articles, products for oral and dental hygiene.

Aroma chemicals according to the invention can be used in the production of perfumed articles. The olfactory properties, like the material properties (such as solubility in customary solvents and compatibility with further customary constituents of such products) of the aroma chemicals according to the invention underline their particular suitability for the stated use purposes. The positive properties contribute to the fact that the aroma chemicals used according to the invention and the flavoring compositions according to the invention are particularly preferably used in perfume products, body care products, hygiene articles, textile detergents, and in cleaners for solid surfaces.

The perfumed article is e.g. selected from perfume products, body care products, hygiene articles, textile detergents and cleaners for solid surfaces. Preferred perfumed articles according to the invention are also selected from among:
  perfume products selected from perfume extracts, Eau de Parfums, Eau de Toilettes, Eau de Colognes, Eau de Solide, Extrait Parfum, air fresheners in liquid form, gel-like form or a form applied to a solid carrier, aerosol sprays, scented cleaners and oils;
  body care products selected from aftershaves, pre-shave products, splash colognes, solid and liquid soaps, shower gels, shampoos, shaving soaps, saving foams, bath oils, cosmetic emulsions of the oil-in-water type, of the water-in-oil type and of the water-in-oil-in-water type, such as e.g. skin creams and lotions, face creams and lotions, sunscreen creams and lotions, aftersun creams and lotions, hand creams and lotions, foot creams and lotions, hair removal creams and lotions, aftershave creams and lotions, tanning creams and lotions, hair care products such as e.g. hairsprays, hair gels, setting hair lotions, hair conditioners, hair shampoo, permanent and semipermanent hair colorants, hair shaping compositions such as cold waves and hair smoothing compositions, hair tonics, hair creams and hair lotions, deodorants and antiperspirants such as e.g. underarm sprays, roll-ons, deodorant sticks, deodorant creams, products of decorative cosmetics such as e.g. eyeshadows, nail varnishes, make-ups, lipsticks, mascara, toothpaste, dental floss;
  hygiene articles selected from candles, lamp oils, joss sticks, insecticides, repellents, propellants, rust removers, perfumed freshening wipes, armpit pads, baby diapers, sanitary towels, toilet paper, cosmetic wipes, pocket tissues, dishwasher deodorizer;
  cleaners for solid surfaces selected from perfumed acidic, alkaline and neutral cleaners, such as e.g. floor cleaners, window cleaners, dishwashing detergents, bath and sanitary cleaners, scouring milk, solid and liquid toilet cleaners, powder and foam carpet cleaners, waxes and polishes such as furniture polishes, floor waxes, shoe creams, disinfectants, surface disinfectants and sanitary cleaners, brake cleaners, pipe cleaners, limescale removers, grill and oven cleaners, algae and moss removers, mold removers, facade cleaners;

textile detergents selected from liquid detergents, powder detergents, laundry pretreatments such as bleaches, soaking agents and stain removers, fabric softeners, washing soaps, washing tablets.

It is preferred if the perfumed article is one of the following:

an acidic, alkaline or neutral cleaner which is selected in particular from all-purpose cleaners, floor cleaners, window cleaners, dishwashing detergents, bath and sanitary cleaners, scouring milk, solid and liquid toilet cleaners, powder and foam carpet cleaners, liquid detergents, powder detergents, laundry pretreatments such as bleaches, soaking agents and stain removers, fabric softeners, washing soaps, washing tablets, disinfectants, surface disinfectants, an air freshener in liquid form, gel-like form or a form applied to a solid carrier or as an aerosol spray, a wax or a polish, which is selected in particular from furniture polishes, floor waxes and shoe creams, or a body care composition, which is selected in particular from shower gels and shampoos, shaving soaps, shaving foams, bath oils, cosmetic emulsions of the oil-in-water type, of the water-in-oil type and of the water-in-oil-in-water type, such as e.g. skin creams and lotions, face creams and lotions, sunscreen creams and lotions, aftersun creams and lotions, hand creams and lotions, foot creams and lotions, hair removal creams and lotions, aftershave creams and lotions, tanning creams and lotions, hair care products such as e.g. hairsprays, hair gels, setting hair lotions, hair conditioners, permanent and semipermanent hair colorants, hair shaping compositions such as cold waves and hair smoothing compositions, hair tonics, hair creams and hair lotions, deodorants and antiperspirants such as e.g. underarm sprays, roll-ons, deodorant sticks, deodorant creams, products of decorative cosmetics.

Ingredients with which aroma chemicals used according to the invention or flavoring compositions according to the invention can preferably be combined are, for example: preservatives, abrasives, antiacne agents, agents to combat skin aging, antibacterial agents, anticellulite agents, antidandruff agents, anti-inflammatory agents, irritation-preventing agents, irritation-alleviating agents, antimicrobial agents, antioxidants, astringents, sweat-inhibiting agents, antiseptics, antistatics, binders, buffers, carrier materials, chelating agents, cell stimulants, cleaning agents, care agents, hair removal agents, surface-active substances, deodorizing agents, antiperspirants, emollients, emulsifiers, enzymes, essential oils, fibers, film formers, fixatives, foam formers, foam stabilizers, substances for preventing foaming, foam boosters, fungicides, gelling agents, gel-forming agents, hair care agents, hair shaping agents, hair smoothing agents, moisture-donating agents, moisturizing substances, humectant substances, bleaching agents, strengthening agents, stain removal agents, optical brighteners, impregnating agents, soil repellents, friction-reducing agents, lubricants, moisturizing creams, ointments, opacifiers, plasticizers, covering agents, polish, shine agents, polymers, powders, proteins, refatting agents, exfoliating agents, silicones, skin-Calming agents, skin-Cleansing agents, skin care agents, skin-healing agents, skin lightening agents, skin-protective agents, skin-softening agents, cooling agents, skin-Cooling agents, warming agents, skin-warming agents, stabilizers, UV-absorbent agents, UV filters, detergents, fabric softeners, suspending agents, skin-tanning agents, thickeners, vitamins, oils, waxes, fats, phospholipids, saturated fatty acids, mono- or polyunsaturated fatty acids, α-hydroxy acids, polyhydroxy fatty acids, liquefiers, dyes, color-protection agents, pigments, anticorrosives, aromas, flavorings, odorants, polyols, surfactants, electrolytes, organic solvents or silicone derivatives.

According to a further aspect, the aroma chemicals are used in the production of the perfumed articles in liquid form, undiluted or diluted with a solvent or in the form of a flavoring composition. Suitable solvents for this purpose are those mentioned above as component c). Reference is made hereto in their entirety.

The aroma chemicals and/or flavoring compositions present in the perfumed articles according to the invention can in this connection, in one embodiment, be absorbed onto a carrier, which ensures both fine distribution of the odorant or odorant composition within the product and controlled release upon use. Carriers of this type may be porous inorganic materials such as light sulfate, silica gels, zeolites, gypsums, clays, clay granules, aerated concrete, etc. or organic materials such as woods and cellulose-based materials.

The aroma chemicals used according to the invention and the flavoring compositions according to the invention can also be in microencapsulated form, spray-dried form, in the form of inclusion complexes or in the form of extrusion products and be added in this form to the product or article to be perfumed. The properties can be further optimized by so-called "coating" with suitable materials with regard to a more targeted release of the scent, for which purpose preferably waxy synthetic substances such as e.g. polyvinyl alcohol are used.

The microencapsulation can take place for example by the so-called coacervation method with the help of capsule materials, e.g. made of polyurethane-like substances or soft gelatin. The spray-dried perfume oils can be produced for example by spray-drying an emulsion or dispersion comprising the perfume oil, wherein carrier substances that can be used are modified starches, proteins, dextrin and vegetable gums. Inclusion complexes can be prepared e.g. by introducing dispersions of odorant compositions and cyclodextrins or urea derivatives into a suitable solvent, e.g. water. Extrusion products can be produced by melting odorants used according to the invention and odorant compositions according to the invention with a suitable wax-like substance and by extrusion with subsequent solidification, optionally in a suitable solvent, e.g. isopropanol.

A further embodiment of the invention provides a method for scenting a product, particularly for imparting and/or enhancing an odor or flavor, in which at least one compound selected from the compounds of the formula (I), preferably from the compounds of the formulae (I.a) and (I.b), more preferably from the compounds of the formulae (I.a1), (I.a2), (I.a3), (I.a4), (I.b1), and (I.b2).

A further embodiment of the invention provides a method for scenting a product, particularly for imparting and/or enhancing an odor or flavor, in which at least one compound selected from the compounds of the formulae (II.a), (II.b), (II.c), (II.d), and (II.e).

EXAMPLES

Analysis of Odor

The odor of the compounds was determined by smelling/sniffing the sample on a smelling strip. If indicated, the number quantifies the intensity in the range of (1)=very low to (6)=very high.

Example 1

Compound (1)

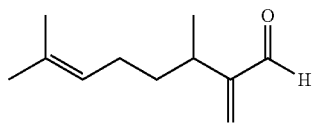
(1)

To a solution of citronellal (racemic, 10.0 kg, 64.9 mol), aqueous formaldehyde (37%, 6.0 kg, 73.8 mol) and isopropanol (iPrOH, 1.04 L), pyrrolidine (550 mL, 6.7 mol) was added over a period of 45 minutes at room temperature. Then, propanoic acid (503 g, 6.7 mol) was added over a period of 45 minutes. After complete addition, the reaction mixture was heated to 45° C. for 4 h, cooled back to room temperature, and diluted with water (20.0 L). The phases were separated and the aqueous layer was extracted with ethyl acetate (20.0 L). The combined organic phases were first washed with 5% aqueous NaHCO$_3$-solution (7.5 L) and then with demineralized water (10 L). The organic layer was separated and the solvent was removed under reduced pressure. The product was obtained as a slightly yellow oil (11 kg, GC purity 98%, yield 99%).

$^1$H-NMR (500 MHz, CDCl$_3$): δ=9.5 (s, 1H), 6.3 (s, 1H), 6.0 (s, 1H), 5.07-5.03 (m, 1H), 2.71-2.64 (m, 1H), 1.96-1.84 (m, 2H), 1.64 (s, 3H), 1.54 (s, 3H), 1.54-1.47 (m, 1H), 1.39-1.32 (m, 1H), 1.04 (d, J=7.0 Hz, 3H) ppm.

$^{13}$C-NMR (125 MHz, CDCl$_3$): δ=17.5, 19.4, 25.6, 25.7, 30.8, 35.5, 124.0, 131.4, 132.9, 155.3, 194.4 ppm.

Odor: citrus (racemic sample corresponding to II.b1 and II.b2).

Example 2

Compound (2)

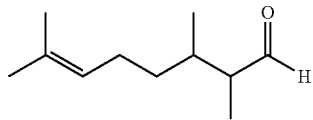
(2)

The compound (1) (3000 g, 18.04 mol), methanol (832.5 g) and Pd/C (35.1 g, 50% H$_2$O) were placed in an autoclave under N$_2$ atmosphere. Trimethylamine (277.3 g, 4.69 mol) was added and the mixture was stirred at room temperature for 30 min before it was heated to 70° C. Then, the autoclave was pressurized with hydrogen (8 bar) and stirring was continued for 29 h, during which 382 L of hydrogen were consumed. After cooling, the autoclave was purged with nitrogen and the reaction mixture was filtered to remove the catalyst. Then, the mixture was diluted with MTBE (2-Methoxy-2 methylpropane, methyl tert-butyl ether) (1.5 L) and extracted with water (1.5 L) three times. The organic phase was dried over Na$_2$SO$_4$, filtered again and the solvent was removed under reduced pressure (60° C., 350 mbar). The crude product was obtained in 95% purity and could directly be used in the next step (yellow oil, 2926 g, 92%).

$^1$H-NMR (500 MHz, CDCl$_3$, racemic mixture of syn- and anti-isomers): δ=9.67 (d, J=1.9 Hz, 1H), 9.65 (d, J=1.4 Hz, 1H), 5.12-5.06 (m, 2H), 2.38-2.27 (m, 2H), 2.09 1.90 (m, 6H), 1.69-1.68 (br dd, J=1.1, 4.7 Hz, 6H), 1.60 (d, J=4.7 Hz, 6H), 1.44-1.18 (m, 4H), 1.04 (d, J=7.0 Hz, 3H), 1.00 (d, J=2.9 Hz, 3H), 0.99 (d, J=2.8 Hz, 3H), 0.84 (d, J=6.9 Hz, 3H) ppm.

$^{13}$C-NMR (125 MHz, CDCl$_3$, syn-isomers corresponding to II.c1 and II.c2): δ=7.9, 15.2, 17.4, 25.60, 25.64, 32.0, 34.7, 50.4, 123.9, 131.6, 205.35 ppm.

$^{13}$C-NMR (125 MHz, CDCl$_3$, anti-isomers corresponding to II.c3 and II.c4): δ=9.7, 17.2, 17.5, 25.56, 25.59, 33.1, 33.2, 51.4, 124.0, 131.6, 205.44 ppm.

Odor: rosy (room-filling), citrus, waxy (racemic sample; d.r.=syn-isomers corresponding to II.c1 and II.c2:anti-isomers corresponding to II.c3 and II.c4=approx. 57:43).

Example 3

Compound (3)

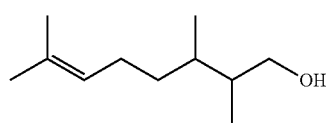
(3)

A solution of compound (2) (171.6 g, 1.02 Mol) in methanol (400 mL) was cooled to 0° C. and NaBH$_4$ (38.58 g, 1.02 Mol) was added in portions over 45 minutes. After complete addition, stirring was continued at 0° C. for 15 minutes. Brine (400 mL) was carefully added, followed by toluene (400 mL). Then, water was added until all precipitate was dissolved (300 mL). The phases were separated and the aqueous phase was re-extracted with toluene (300 mL). The combined organic phases were washed twice with saturated aqueous NaHCO$_3$-solution, dried over Na$_2$SO$_4$, and the solvent was removed under reduced pressure.

$^{13}$C-NMR (125 MHz, CDCl$_3$, syn-isomers corresponding to II.d1 and II.d2): δ=11.3, 14.2, 17.7, 25.7, 26.0, 32.9, 35.1, 39.5, 66.8, 124.8, 131.3 ppm.

$^{13}$C-NMR (125 MHz, CDCl$_3$, anti-isomers corresponding to II.d3 and II.d4): δ=13.5, 16.9, 17.7, 25.7, 26.0, 32.8, 34.1, 40.7, 66.0, 124.8, 131.4 ppm.

Odor: see below (compositions Z1, Z2, Z3, Z4).

Example 4

Compound (4)

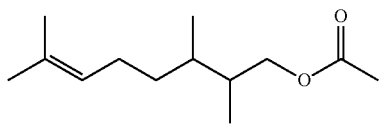
(4)

A mixture of compound (3) (9.27 g, 54.5 mMol), Zn-acetate dihydrate (5 mg, 0.05 W % Zn) and toluene (80 mL) was heated to 60° C. Then, ketene (obtained from pyrolysis of 0.411 mL/min acetone) was passed through the reaction mixture under fast stirring for 135 min. Then, the reaction mixture was cooled to room temperature, extracted with water and phases were separated. The solvent of the organic phase was removed under reduced pressure and the product was obtained as slightly yellow liquid (10.9 g, purity 97 GC-A %, yield 92%).

$^{13}$C-NMR (125 MHz, CDCl$_3$, syn-isomers corresponding to I.a1 and I.a2): δ=11.7, 14.4, 17.6, 21.0, 25.7, 25.9, 33.3, 34.7, 36.0, 68.2, 124.6, 131.3, 171.2 ppm.

$^{13}$C-NMR (125 MHz, CDCl$_3$, anti-isomers corresponding to I.a3 and I.a4): δ=13.9, 16.5, 17.6, 21.0, 25.7, 25.9, 33.0, 34.5, 37.0, 67.5, 124.6, 131.3, 171.2 ppm.

Odor: see below (compositions Z5, Z6, Z7).

Example 5

Compound (5)

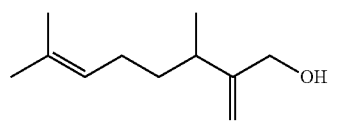

(5)

A solution of compound (1) (100 g, 0.60 mol) in methanol (200 mL) was cooled to 0° C. and NaBH$_4$ (22.75 g) was added portionwise over 45 minutes. After complete addition, stirring was continued for 15 minutes. Then, brine (100 mL) was added carefully followed by toluene (200 mL). Additional water was added until all precipitate was dissolved. After phase separation, the aqueous phase was re-extracted with toluene (100 mL) and the combined organic phases were washed with saturated aqueous NaHCO$_3$-solution (100 mL). The organic phase was dried over Na$_2$SO$_4$ and the solvent was removed under reduced pressure (60° C., 100 to 5 mbar). An analytically pure sample was prepared by column chromatography over SiO$_2$.

$^1$H-NMR (500 MHz, CDCl$_3$): δ=5.10-5.06 (m, 1H), 5.05-5.04 (m, 1H), 4.88 (br s, 1H), 4.09 (d, J=5.0 Hz, 2H), 2.20-2.13 (m, 1H), 1.94 (q, J=7.6 Hz, 2H), 1.67 (s, 3H), 1.58 (s, 3H), 1.54 (t, J=5.9 Hz, 1H), 1.52-1.45 (m, 1H), 1.37-1.30 (m, 1H), 1.05 (d, J=7.0, 3 H) ppm.

$^{13}$C-NMR (125 MHz, CDCl$_3$): δ=17.7, 20.2, 25.8, 25.9, 35.8, 36.6, 64.7, 107.8, 124.5, 131.5, 153.9 ppm.

Odor: rose

Example 6

Compound (6)

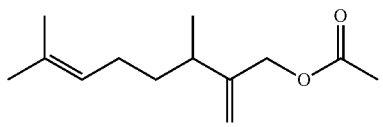

(6)

A mixture of compound (5) (69.8 g, 0.41 mol) and Zn-acetate dihydrate (35 mg, 0.05 W % Zn) was heated to 80° C. Then, ketene (obtained from pyrolysis of 0.411 mL/min acetone) was passed through the reaction mixture under fast stirring for 9 h 30 min. Then, the reaction mixture was cooled to room temperature, extracted with water and phases were separated. The solvent of the organic phase was removed under reduced pressure and the product was obtained as slightly yellow liquid (77.9 g, purity 87 GC-A %, yield 79%). The product was purified by fractional distillation under vacuum.

$^1$H-NMR (500 MHz, CDCl$_3$): δ=5.08-5.04 (m, 1H), 5.02 (q, J=1.4 Hz, 1H), 4.93 (br s, 1H), 4.52 (br s, 2H), 2.21-2.14 (m, 1H), 2.07 (s, 3H), 1.93 (q, J=7.6 Hz, 2H), 1.66 (br s, 3H), 1.57 (s, 3H), 1.52-1.44 (m, 1H), 1.36-1.29 (m, 1H), 1.05 (d, J=7.0 Hz, 3H) ppm.

$^{13}$C-NMR (125 MHz, CDCl$_3$): δ=17.7, 19.9, 21.0, 25.7, 25.8, 35.6, 36.9, 65.6, 111.0, 124.3, 131.5, 148.4, 170.8 ppm.

Odor: see below (composition Z8)

Example 7

Compound (7)

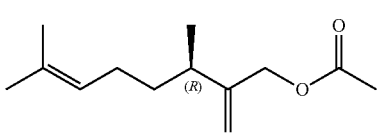

(7)

By the method described for example 6, the compound 7 can be prepared. (R)-3,7-Dimethyl-6-octen-1-al ((R)-citronellal) is used as starting material.

Odor: see below (Z9)

Example 8

Compound (8)

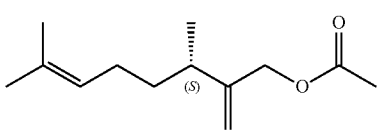

(8)

By the method described for example 6, the compound 8 can be prepared. (S)-3,7-Dimethyl-6-octen-1-al ((S)-citronellal) is used as starting material.

Odor: see below (Z10)

Odors and Aromas

For further odor characterization, the following compositions were produced.

| Comp. | Components | Purity | Enantiomeric purity[1,2] | Ratio of diastereomers[3] anti:syn |
|---|---|---|---|---|
| Z1 | main components: syn-isomers (II.d1) and (II.d2) | 99% | racemic | 5:95 |
| Z2 | main components: anti-isomers (II.d3) and (II.d4) | 99% | racemic | 79:21 |
| Z3 | main component: syn-isomer (II.d1) | 99% | approx. 88% ee | 11:89 |

-continued

| Comp. | Components | Purity | Enantiomeric purity[1,2] | Ratio of diastereomers[3] anti:syn |
|---|---|---|---|---|
| Z4 | main component: anti-isomer (II.d3) | 99% | approx. 88% ee | 77:23 |
| Z5 | main components: syn-isomers (I.a1) and (I.a2) | 97% | racemic | 42:58 |
| Z6 | main components: anti-isomers (I.a3) and (I.a4) | 93% | racemic | 78:22 |
| Z7 | main components: syn-isomers (I.a1) and (I.a2) | 99% | racemic | 18:82 |

[1] enantiomeric purity of starting material II.a
[2] ee = enantiomeric excess
[3] based on GC-A %
Z8 Composition comprising a racemic mixture of compounds (I.b1) and (I.b2)
Z9 Composition comprising compound (I.b1)
Z10 Composition comprising compound (I.b2)

The following odors and/or aromas were determined:
Z1: Geranium 4, rose 4, honey 2, room-filling, good overall impression. Intensity 4.
Z2: Geranium 4, rose 4, green 3, woody 2, room-filling, good overall impression. Intensity 4.
Z3: Geranium 4, rose 4, herbaceous 3, fatty 2, room-filling, good overall impression. Intensity 4.
Z4: Geranium 4, rose 4, green 3, herbaceous 3, room-filling, good overall impression. Intensity 4.
Z5: Herbaceous 3, green 2, in the beginning technical odor which disappears after 2-3 minutes. Then, natural, fresh impression, slightly weak. Intensity 2.
Z6: Floral 3, freesia 2, watery 2, sweet 2, pleasantly fresh, slightly weak. Intensity 2.
Z7: After 5 minutes herbaceous 3, watery-ozone 3, weak.
Z8: Floral 5, rose 5, waxy 2. Intensity 2.
Z9: Intensity 5; rose 6, citrus 4, in the beginning sulphur-like 4; after 24 h: Intensity 3; floral 4, rose 3, woody-dry 2.
Z10: Intensity 4; rose 3, citrus 3; after 24 h: Intensity 3; floral 4, rose 4.

The compound of example 1 can be used as the essentially pure R-isomer, or as the essentially pure S-isomer or as a mixture of these isomers; e.g. a mixture of the R- and the S-isomer, e.g. a 50:50 mixture, or a 5:95 mixture.

The compound of example 2 can be used as the essentially pure R,R-isomer or as the essentially pure S,S-isomer or as the essentially pure R,S-isomer, or as the essentially pure S,R-isomer or as a mixture of at least two of these isomers; e.g. a mixture of the R,R- and the S,S-isomer, e.g. a 50:50 mixture, 80:20 mixture; or a mixture of the R,S- and the S,R-isomer; e.g. a 50:50 mixture, or a mixture of all 4 isomers, e.g. a 25:25:25:25 mixture.

The compound of example 3 can be used as the essentially pure R,S-isomer or as the essentially pure S,S-isomer or as the essentially pure R,S-isomer, or as the essentially pure S,R-isomer or as a mixture of at least two of these isomers; e.g. a mixture of the R,R- and the S,S-isomer, e.g. a 50:50 mixture; or a mixture of the R,S- and the S,R-isomer; e.g. a 50:50 mixture, or a mixture of all 4 isomers, e.g. a 25:25:25:25 mixture.

The compound of example 4 can be used as the essentially pure R,R-isomer or as the essentially pure S,S-isomer or as the essentially pure R,S-isomer, or as the essentially pure S,R-isomer or as a mixture of at least two of these isomers; e.g. a mixture of the R,R- and the S,S-isomer, e.g. a 50:50 mixture; or a mixture of the R,S- and the S,R-isomer; e.g. a 50:50 mixture, or a mixture of all 4 isomers, e.g. a 25:25:25:25 mixture.

The compound of example 5 can be used as the essentially pure R-isomer or as the essentially pure S-isomer or as a mixture of at least two of these isomers; e.g. a 50:50 mixture.

The compound of example 6 can be used as the essentially pure R-isomer or as the essentially pure S-isomer or as a mixture of two of the isomers; e.g. a mixture of the R- and the S-isomer, e.g. a 70:30 mixture, or a 80:20 mixture.

The compound of example 7 can be used as the essentially pure R-isomer or as the essentially pure S-isomer or as a mixture of two of the isomers; e.g. a mixture of the R- and the S-isomer, e.g. a 70:30 mixture, or a 80:20 mixture.

The compound of example 8 can be used as the essentially pure R-isomer or as the essentially pure S-isomer or as a mixture of two of the isomers; e.g. a mixture of the R- and the S-isomer, e.g. a 70:30 mixture, or a 80:20 mixture.

The compounds obtained in the preparation examples, to be more precise in examples 1, 2, 3, 4, 5, 6, 7, 8 were formulated in the perfume compositions according to tables 3 and 4 (components are given as part by weight):

TABLE 3

Perfume oil compositions 1A and 1B

| | 1A | 1B |
|---|---|---|
| Benzoe Siam 20% | 711 | 711 |
| Rosewood Oil brasilian | 85 | 85 |
| Copaivabalm rect. | 9 | 9 |
| Linalyl-benzoate | 31 | 31 |
| 3-cis-Hexenyl-salicylate | 21 | 21 |
| Geranyl-acetate | 47 | 47 |
| Ethyl-benzoate | 12 | 12 |
| Cinnamyl-acetate | 2 | 2 |
| Benzyl-acetate | 71 | 71 |
| Methyl-anthranilate 10% | 5 | 5 |
| Bayoil St. Thomas 10% | 5 | 5 |
| Compound of example 1 | 0 | 20 |
| | 1000 | 1020 |

TABLE 4

Perfume oil compositions 2A and 2B

| | 2A | 2B |
|---|---|---|
| Ethyl Caproate | 1 | 1 |
| Ethyl Acetate | 1 | 1 |
| Iso Amyl Butyrate | 1 | 1 |
| Maltol or Veltol | 1 | 1 |
| Geranyl Butyrate | 2 | 2 |
| Ethyl Vanilline 10% DPG | 2 | 2 |
| Cis 3 Hexenyl Acetate | 3 | 3 |
| Allyl Caproate | 3 | 3 |
| Verdural B 10% DPG | 3 | 3 |
| Oxyphenylon | 3 | 3 |
| Hexyl Butyrate | 4 | 4 |
| Ethyl Decadienoate 10% DPG | 4 | 4 |
| DM.B.C. Butyrate | 4 | 4 |
| Ethyl Maltol or Veltol Plus | 4 | 4 |
| Cyclaprop | 5 | 5 |
| Iso Amyl Acetate | 5 | 5 |
| Cis 3 Hexenol 10% DPG | 6 | 6 |
| D.M.B.C. Acetate | 7 | 7 |
| Aldehyde C 16 100% | 8 | 8 |
| Geranyl Propionate | 8 | 8 |
| Ethyl 2 Methyl Butyrate | 8 | 8 |
| Decalactone Gamma | 10 | 10 |
| Orange Bresil Oil | 10 | 10 |
| Ethyl Aceto Acetate | 10 | 10 |
| Linalool | 15 | 15 |
| Benzyl Acetate | 15 | 15 |
| Aldehyde C 14 100% | 20 | 20 |
| Citronellol | 25 | 25 |

TABLE 4-continued

Perfume oil compositions 2A and 2B

|  | 2A | 2B |
|---|---|---|
| Linalyl Acetate | 30 | 30 |
| Geranyl Acetate | 35 | 35 |
| Vertenex | 45 | 45 |
| Citronellyl Acetate | 50 | 50 |
| Verdox | 54 | 54 |
| Galaxolide 50 DEP | 100 | 100 |
| Hexyl Acetate | 190 | 190 |
| Mono Propylene Glycol | 300 | 300 |
| Compound of example 1 | 0 | 200 |
|  | 1000 | 1200 |

Perfume oil composition 3 corresponds to perfume oil composition 1B, where the compound of example 1 is replaced by the same amount of the compound of example 2.

Perfume oil composition 4 corresponds to perfume oil composition 1B, where the compound of example 1 is replaced by the same amount of the compound of example 3.

Perfume oil composition 5 corresponds to perfume oil composition 1B, where the compound of example 1 is replaced by the same amount of the compound of example 4.

Perfume oil composition 6 corresponds to perfume oil composition 1B, where the compound of example 1 is replaced by the same amount of the compound of example 5.

Perfume oil composition 7 corresponds to perfume oil composition 1B, where the compound of example 1 is replaced by the same amount of the compound of example 6.

Perfume oil composition 8 corresponds to perfume oil composition 1B, where the compound of example 1 is replaced by the same amount of the compound of example 7.

Perfume oil composition 9 corresponds to perfume oil composition 1B, where the compound of example 1 is replaced by the same amount of the compound of example 8.

Perfume oil composition 10 corresponds to perfume oil composition 2B, where the compound of example 1 is replaced by the same amount of the compound of example 2.

Perfume oil composition 11 corresponds to perfume oil composition 2B, where the compound of example 1 is replaced by the same amount of the compound of example 3.

Perfume oil composition 12 corresponds to perfume oil composition 2B, where the compound of example 1 is replaced by the same amount of the compound of example 4.

Perfume oil composition 13 corresponds to perfume oil composition 2B, where the compound of example 1 is replaced by the same amount of the compound of example 5.

Perfume oil composition 14 corresponds to perfume oil composition 2B, where the compound of example 1 is replaced by the same amount of the compound of example 6.

Perfume oil composition 15 corresponds to perfume oil composition 2B, where the compound of example 1 is replaced by the same amount of the compound of example 7.

Perfume oil composition 16 corresponds to perfume oil composition 2B, where the compound of example 1 is replaced by the same amount of the compound of example 8.

The compounds of formula (I), in particular the compounds of examples 1, 2, 3, 4, 5, 6, 7 and 8, either as essentially pure isomers or as the enantiomeric or diastereomeric mixtures as described above, may be used in a broad range of fragrance applications, e.g. in any field of fine and functional perfumery, such as perfumes, household products, laundry products, body care products and cosmetics. The compounds of formula (I), in particular the compounds of examples 1, 2, 3, 4, 5, 6, 7 and 8, either as essentially pure isomers or as the enantiomeric or diastereomeric mixtures as described above, can be employed in widely varying amounts, depending upon the specific application and on the nature and quantity of other odorant ingredients. The proportion is typically from 0.001 to 20 weight percent of the application. In one embodiment, the compounds of formula (I), in particular the compounds of examples 1, 2, 3, 4, 5, 6, 7 and 8, either as essentially pure isomers or as the enantiomeric or diastereomeric mixtures as described above, are employed in a fabric softener in an amount of from 0.001 to 0.05 weight percent. In another embodiment, the compounds of formula (I), in particular the compounds of examples 1, 2, 3, 4, 5, 6, 7 and 8, either as essentially pure isomers or as the enantiomeric or diastereomeric mixtures as described above, are used in fine perfumery in amounts of from 0.1 to 20 weight percent, more preferably between 0.1 and 5 weight percent. However, these values are given only by way of example, since the experienced perfumer may also achieve effects or may create novel accords with lower or higher concentrations.

The compounds of formula (I), in particular the compounds of examples 1, 2, 3, 4, 5, 6, 7 and 8, either as essentially pure isomers or as the enantiomeric or diastereomeric mixtures as described above, may be employed into the fragrance application simply by directly mixing the fragrance composition with the fragrance application, or they may, in an earlier step be entrapped with an entrapment material, for example, polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzyme, or the like, and then mixed with the application.

Thus, the invention additionally provides a method of manufacturing a fragrance application, comprising the incorporation of a compound of formula (I), in particular a compound of examples 1, 2, 3, 4, 5, 6, 7 and 8, either as essentially pure isomers or as the enantiomeric or diastereomeric mixtures as described above, as a fragrance ingredient, either by directly admixing the compound of formula (I) to the application or by admixing a fragrance composition comprising a compound of the formula (I), in particular a compound of examples 1, 2, 3, 4, 5, 6, 7 and 8, either as essentially pure isomers or as the enantiomeric or diastereomeric mixtures as described above, which may then be mixed to a fragrance application, using conventional techniques and methods.

As used herein, "fragrance application" means any product, such as fine perfumery, e.g. perfume and Eau de Toilette; household products, e.g. detergents for dishwasher, surface cleaner; laundry products, e.g. softener, bleach, detergent; body care products, e.g. shampoo, shower gel; and cosmetics, e.g. deodorant, vanishing creme, comprising an odourant. This list of products is given by way of illustration and is not to be regarded as being in any way limiting.

The compounds of formula (I), in particular the compounds of examples 1, 2, 3, 4, 5, 6, 7 and 8, either as essentially pure isomers or as the enantiomeric or diastereomeric mixtures as described above, may be used as part of the perfume in the above mentioned applications. The compounds of formula (I), in particular the compounds of examples 1, 2, 3, 4, 5, 6, 7 and 8, either as essentially pure isomers or as the enantiomeric or diastereomeric mixtures as described above, may be used alone or as part of a perfume. The term "perfume" is used synonymously to "perfume oil" or "perfume (oil) composition".

In the following tables all amounts are given in weight-% (% b.w.). Conc. means concentration.

TABLE 5

Deo pump spray 1
Deo Pump Spray; PIT

| Component | INCI | amount % |
|---|---|---|
| EMULGADE ® SE-PF | Glyceryl Stearate (and) Ceteareth-20 (and) Ceteareth-12 (and) Cetearyl Alcohol (and) Cetyl Palmitate | 3.9 |
| EUMULGIN ® B2 | Ceteareth-20 | 1.6 |
| CETIOL ® OE | Dicaprylyl Ether | 5 |
| CETIOL ® PGL | Hexyldecanol (and) Hexyldecyl Laurate | 2 |
| Irgasan DP 300 | Triclosan | 0.25 |
| HYDAGEN ® DEO | Triethyl Citrate (and) BHT | 2.5 |
| Water, de ionized | Aqua | 19 |
| Eumulgin ® HRE 60 | PEG-60 Hydrogenated Castor Oil | 1.5 |
| Perfume oil composition 1B | Perfume | 0.5 |
| Water, de ionized | Aqua | ad 100 |
| Preservative | | q.s., |
| Viscosity mPas | | <100 |

Deo pump spray 2 corresponds to deo pump spray 1, where the perfume oil composition 1B is replaced by the same amount of the perfume oil composition 2B.

Deo pump spray 3 corresponds to deo pump spray 1, where the perfume oil composition 1B is replaced by the same amount of perfume oil composition 3.

Deo pump spray 4 corresponds to deo pump spray 1, where the perfume oil composition 1B is replaced by the same amount of the perfume oil composition 4.

Deo pump spray 5 corresponds to deo pump spray 1, where the perfume oil composition 1B is replaced by the same amount of the perfume oil composition 5.

Deo pump spray 6 corresponds to deo pump spray 1, where the perfume oil composition 1B is replaced by the same amount of the perfume oil composition 6.

Deo pump spray 7 corresponds to deo pump spray 1, where the perfume oil composition 1B is replaced by the same amount of the perfume oil composition 7.

Deo pump spray 8 corresponds to deo pump spray 1, where the perfume oil composition 1B is replaced by the same amount of the perfume oil composition 8.

Deo pump spray 9 corresponds to deo pump spray 1, where the perfume oil composition 1B is replaced by the same amount of the perfume oil composition 9.

Deo pump spray 10 corresponds to deo pump spray 1, where the perfume oil composition 1B is replaced by the same amount of the perfume oil composition 10.

Deo pump spray 11 corresponds to deo pump spray 1, where the perfume oil composition 1B is replaced by the same amount of the perfume oil composition 11.

Deo pump spray 12 corresponds to deo pump spray 1, where the perfume oil composition 1B is replaced by the same amount of the perfume oil composition 12.

Deo pump spray 13 corresponds to deo pump spray 1, where the perfume oil composition 1B is replaced by the same amount of the perfume oil composition 13.

Deo pump spray 14 corresponds to deo pump spray 1, where the perfume oil composition 1B is replaced by the same amount of the perfume oil composition 14.

Deo pump spray 15 corresponds to deo pump spray 1, where the perfume oil composition 1B is replaced by the same amount of the perfume oil composition 15.

Deo pump spray 16 corresponds to deo pump spray 1, where the perfume oil composition 1B is replaced by the same amount of the perfume oil composition 16.

TABLE 6

Deo pump spray 17
Deo Pump Spray

| Component | INCI | amount % |
|---|---|---|
| Eumulgin ® HRE 60 | PEG-60 Hydrogenated Castor Oil | 2 |
| Farnesol | Deo ingredient | 0.2 |
| HYDAGEN ® DCMF | Chitosan | 0.1 |
| glycolic acid (Fa. Merck) | glycolic acid | 0.04 |
| Water, de ionized | | ad 100 |
| Perfume oil composition 1B | Perfume | 0.5 |
| pH value | 4 | |

Deo pump spray 18 corresponds to deo pump spray 17, where the perfume oil composition 1B is replaced by the same amount of the perfume oil composition 2B.

Deo pump spray 19 corresponds to deo pump spray 17, where the perfume oil composition 1B is replaced by the same amount of the perfume oil composition 3.

Deo pump spray 20 corresponds to deo pump spray 17, where the perfume oil composition 1B is replaced by the same amount of the perfume oil composition 4.

Deo pump spray 21 corresponds to deo pump spray 17, where the perfume oil composition 1B is replaced by the same amount of the perfume oil composition 5.

Deo pump spray 22 corresponds to deo pump spray 17, where the perfume oil composition 1B is replaced by the same amount of the perfume oil composition 6.

Deo pump spray 23 corresponds to deo pump spray 17, where the perfume oil composition 1B is replaced by the same amount of the perfume oil composition 7.

Deo pump spray 24 corresponds to deo pump spray 17, where the perfume oil composition 1B is replaced by the same amount of the perfume oil composition 8.

Deo pump spray 25 corresponds to deo pump spray 17, where the perfume oil composition 1B is replaced by the same amount of the perfume oil composition 9.

Deo pump spray 26 corresponds to deo pump spray 17, where the perfume oil composition 1B is replaced by the same amount of the perfume oil composition 10.

Deo pump spray 27 corresponds to deo pump spray 17, where the perfume oil composition 1B is replaced by the same amount of the perfume oil composition 11.

Deo pump spray 28 corresponds to deo pump spray 17, where the perfume oil composition 1B is replaced by the same amount of the perfume oil composition 12.

Deo pump spray 29 corresponds to deo pump spray 17, where the perfume oil composition 1B is replaced by the same amount of the perfume oil composition 13.

Deo pump spray 30 corresponds to deo pump spray 17, where the perfume oil composition 1B is replaced by the same amount of the perfume oil composition 14.

Deo pump spray 31 corresponds to deo pump spray 17, where the perfume oil composition 1B is replaced by the same amount of the perfume oil composition 15.

Deo pump spray 32 corresponds to deo pump spray 17, where the perfume oil composition 1B is replaced by the same amount of the perfume oil composition 16.

TABLE 7

Clean hair conditioner 1
Clear Hair Conditioner

| Component | INCI | amount % |
|---|---|---|
| DEHYQUART ® L 80 | Dicocoylethyl Hydroxyethylmonium Methosulfate (and) Propylene Glycol | 1.0 |
| Propylene Glycol | solvent | 10.0 |
| Eumulgin ® HRE 60 | PEG-60 Hydrogenated Castor Oil | 1.0 |
| LAMESOFT ® PO 65 | Coco-Glucoside (and) Glyceryl Oleate | 1.0 |
| GLUADIN ® W 40 | Hydrolyzed Wheat Gluten Hydrolyzed Wheat Protein | 0.5 |
| Perfume oil composition 1B | Perfume | 0.02 |
| Preservative | | q.s |
| HYDAGEN ® HCMF | Chitosan | 10.0 (sol. 1%) |
| Water, deionized | | up to 100.0 |
| pH-value | | 3.5-4.0 |

Clean hair conditioner 2 corresponds to clean hair conditioner 1, where the perfume oil composition 1B is replaced by the same amount of the perfume oil composition 1B 2.

Clean hair conditioner 3 corresponds to clean hair conditioner 1, where the perfume oil composition 1B is replaced by the same amount of the perfume oil composition 1B 3.

Clean hair conditioner 4 corresponds to clean hair conditioner 1, where the perfume oil composition 1B is replaced by the same amount of the perfume oil composition 1B 4.

Clean hair conditioner 5 corresponds to clean hair conditioner 1, where the perfume oil composition 1B is replaced by the same amount of the perfume oil composition 1B 5.

Clean hair conditioner 6 corresponds to clean hair conditioner 1, where the perfume oil composition 1B is replaced by the same amount of the perfume oil composition 1B 6.

Clean hair conditioner 7 corresponds to clean hair conditioner 1, where the perfume oil composition 1B is replaced by the same amount of the perfume oil composition 1B 7.

Clean hair conditioner 8 corresponds to clean hair conditioner 1, where the perfume oil composition 1B is replaced by the same amount of the perfume oil composition 8.

Clean hair conditioner 9 corresponds to clean hair conditioner 1, where the perfume oil composition 1B is replaced by the same amount of the perfume oil composition 9.

Clean hair conditioner 10 corresponds to clean hair conditioner 1, where the perfume oil composition 1B is replaced by the same amount of the perfume oil composition 10.

Clean hair conditioner 11 corresponds to clean hair conditioner 1, where the perfume oil composition 1B is replaced by the same amount of the perfume oil composition 11.

Clean hair conditioner 12 corresponds to clean hair conditioner 1, where the perfume oil composition 1B is replaced by the same amount of the perfume oil composition 12.

Clean hair conditioner 13 corresponds to clean hair conditioner 1, where the perfume oil composition 1B is replaced by the same amount of the perfume oil composition 13.

Clean hair conditioner 14 corresponds to clean hair conditioner 1, where the perfume oil composition 1B is replaced by the same amount of the perfume oil composition 14.

Clean hair conditioner 15 corresponds to clean hair conditioner 1, where the perfume oil composition 1B is replaced by the same amount of the perfume oil composition 15.

Clean hair conditioner 16 corresponds to clean hair conditioner 1, where the perfume oil composition 1B is replaced by the same amount of the perfume oil composition 16.

TABLE 8

Face wash gel 1
Face Wash Gel

| Component | INCI | amount % |
|---|---|---|
| PLANTAPON ® 611 L | Sodium Laureth Sulfate (and) Lauryl Glucoside (and) Cocamidopropyl Betaine | 20 |
| PLANTAPON ® ACG 35 | Disodium Cocoyl Glutamate | 1 |
| LAMESOFT ® PO 65 | Coco-Glucoside (and) Glyceryl Oleate | 2 |
| NaCl | Sodium Chloride | 1.7 |
| PLANTACARE ® PS 10 | Sodium Laureth Sulfate (and) Lauryl Polyglucose | 0.3 |
| Perfume oil composition 1B | Perfume | 0.1 |
| Water | Aqua | QS |
| Preservative | | QS |
| Dye | | QS |
| pH 6 to 7 | | |

Face wash gel 2 corresponds to face wash gel 1, where the perfume oil composition 1B is replaced by the same amount of the perfume oil composition 2B.

Face wash gel 3 corresponds to face wash gel 1, where the perfume oil composition 1B is replaced by the same amount of the perfume oil composition 3.

Face wash gel 4 corresponds to face wash gel 1, where the perfume oil composition 1B is replaced by the same amount of the perfume oil composition 4.

Face wash gel 5 corresponds to face wash gel 1, where the perfume oil composition 1B is replaced by the same amount of the perfume oil composition 5.

Face wash gel 6 corresponds to face wash gel 1, where the perfume oil composition 1B is replaced by the same amount of the perfume oil composition 6.

Face wash gel 7 corresponds to face wash gel 1, where the perfume oil composition 1B is replaced by the same amount of perfume oil composition 7.

Face wash gel 8 corresponds to face wash gel 1, where the perfume oil composition 1B is replaced by the same amount of the perfume oil composition 8.

Face wash gel 9 corresponds to face wash gel 1, where the perfume oil composition 1B is replaced by the same amount of the perfume oil composition 9.

Face wash gel 10 corresponds to face wash gel 1, where the perfume oil composition 1B is replaced by the same amount of the perfume oil composition 10.

Face wash gel 11 corresponds to face wash gel 1, where the perfume oil composition 1B is replaced by the same amount of the perfume oil composition 11.

Face wash gel 12 corresponds to face wash gel 1, where the perfume oil composition 1B is replaced by the same amount of the perfume oil composition 12.

Face wash gel 13 corresponds to face wash gel 1, where the perfume oil composition 1B is replaced by the same amount of the perfume oil composition 13.

Face wash gel 14 corresponds to face wash gel 1, where the perfume oil composition 1B is replaced by the same amount of the perfume oil composition 14.

Face wash gel 15 corresponds to face wash gel 1, where the perfume oil composition 1B is replaced by the same amount of the perfume oil composition 15.

Face wash gel 16 corresponds to face wash gel 1, where the perfume oil composition 1B is replaced by the same amount of the perfume oil composition 16.

TABLE 9

Foam bath concentrate 1
Foam Bath Concentrate

| Component | INCI | Amount % |
|---|---|---|
| TEXAPON ® K 14 S 70spec. | Sodium Myreth Sulfate | 25 |
| PLANTACARE ® 2000 UP | Decyl Glucoside | 20 |
| DEHYTON ® K | Cocamidopropyl Betaine | 20 |
| GLUADIN ® WP | Hydrolyzed Wheat Gluten Hydrolyzed Wheat Protein | 1 |
| PLANTACARE ® PS 10 | Sodium Laureth Sulfate (and) Lauryl Polyglucose | 5 |
| Water, de ionized | | ad 100 |
| Citric Acid, 50% | | 0.5 |
| Perfume oil composition 1B | perfume | 2.0 |
| pH value | | 5.5 |

Foam bath concentrate 2 corresponds to foam bath concentrate 1, where the perfume oil composition 1B is replaced by the same amount of the perfume oil composition 2B.

Foam bath concentrate 3 corresponds to foam bath concentrate 1, where the perfume oil composition 1B is replaced by the same amount of the perfume oil composition 3.

Foam bath concentrate 4 corresponds to foam bath concentrate 1, where the perfume oil composition 1B is replaced by the same amount of the perfume oil composition 4.

Foam bath concentrate 5 corresponds to foam bath concentrate 1, where the perfume oil composition 1B is replaced by the same amount of the perfume oil composition 5.

Foam bath concentrate 6 corresponds to foam bath concentrate 1, where the perfume oil composition 1B is replaced by the same amount of the perfume oil composition 6.

Foam bath concentrate 7 corresponds to foam bath concentrate 1, where the perfume oil composition 1B is replaced by the same amount of the perfume oil composition 7.

Foam bath concentrate 8 corresponds to foam bath concentrate 1, where the perfume oil composition 1B is replaced by the same amount of the perfume oil composition 8.

Foam bath concentrate 9 corresponds to foam bath concentrate 1, where the perfume oil composition 1B is replaced by the same amount of the perfume oil composition 9.

Foam bath concentrate 10 corresponds to foam bath concentrate 1, where the perfume oil composition 1B is replaced by the same amount of the perfume oil composition 10.

Foam bath concentrate 11 corresponds to foam bath concentrate 1, where the perfume oil composition 1B is replaced by the same amount of the perfume oil composition 11.

Foam bath concentrate 12 corresponds to foam bath concentrate 1, where the perfume oil composition 1B is replaced by the same amount of the perfume oil composition 12.

Foam bath concentrate 13 corresponds to foam bath concentrate 1, where the perfume oil composition 1B is replaced by the same amount of the perfume oil composition 13.

Foam bath concentrate 14 corresponds to foam bath concentrate 1, where the perfume oil composition 1B is replaced by the same amount of the perfume oil composition 14.

Foam bath concentrate 15 corresponds to foam bath concentrate 1, where the perfume oil composition 1B is replaced by the same amount of the perfume oil composition 15.

Foam bath concentrate 16 corresponds to foam bath concentrate 1, where the perfume oil composition 1B is replaced by the same amount of the perfume oil composition 16.

TABLE 10

Hair gel 1
Hair Gel

| Component | INCI | amount % |
|---|---|---|
| HYDAGEN ® HCMF | Chitosan | 0.5 |
| Glycolic Acid (Fa. Merck) | Solvent | 0.2 |
| Water | | ad 100 |
| Jaguar HP 105 (2% swelling) | Thickener | 65 |
| Eumulgin ® HRE 60 | PEG-60 Hydrogenated Castor Oil | 1.5 |
| Perfume oil composition 1B | Perfume | 0.1 |
| Ethanol | Evaporation agent | 7 |
| pH-value | | 5.8 |

Viscosity (mPas), Brook. RVF, 23° C., sp. 7, 10 rpm = 20.000

Hair gel 2 corresponds to hair gel 1, where the perfume oil composition 1B is replaced by the same amount of the perfume oil composition 2B.

Hair gel 3 corresponds to hair gel 1, where the perfume oil composition 1B is replaced by the same amount of the perfume oil composition 3.

Hair gel 4 corresponds to hair gel 1, where the perfume oil composition 1B is replaced by the same amount of the perfume oil composition 4.

Hair gel 5 corresponds to hair gel 1, where the perfume oil composition 1B is replaced by the same amount of the perfume oil composition 5.

Hair gel 6 corresponds to hair gel 1, where the perfume oil composition 1B is replaced by the same amount of the perfume oil composition 6.

Hair gel 7 corresponds to hair gel 1, where the perfume oil composition 1B is replaced by the same amount of the perfume oil composition 7.

Hair gel 8 corresponds to hair gel 1, where the perfume oil composition 1B is replaced by the same amount of the perfume oil composition 8.

Hair gel 9 corresponds to hair gel 1, where the perfume oil composition 1B is replaced by the same amount of the perfume oil composition 9.

Hair gel 10 corresponds to hair gel 1, where the perfume oil composition 1B is replaced by the same amount of the perfume oil composition 10.

Hair gel 11 corresponds to hair gel 1, where the perfume oil composition 1B is replaced by the same amount of the perfume oil composition 11.

Hair gel 12 corresponds to hair gel 1, where the perfume oil composition 1B is replaced by the same amount of the perfume oil composition 12.

Hair gel 13 corresponds to hair gel 1, where the perfume oil composition 1B is replaced by the same amount of the perfume oil composition 13.

Hair gel 14 corresponds to hair gel 1, where the perfume oil composition 1B is replaced by the same amount of the perfume oil composition 14.

Hair gel 15 corresponds to hair gel 1, where the perfume oil composition 1B is replaced by the same amount of the perfume oil composition 15.

Hair gel 16 corresponds to hair gel 1, where the perfume oil composition 1B is replaced by the same amount of the perfume oil composition 16.

TABLE 11

Self foaming bodywash 1
Self foaming bodywash

| Component | INCI | amount % |
|---|---|---|
| TEXAPON ® SB 3 KC | Disodium Laureth Sulfosuccinate | 16.5 |
| DEHYTON ® K | Cocamidopropyl Betaine | 6.5 |
| PLANTACARE ® 818 UP | Coco Glucoside | 7.5 |
| TEXAPON ® NSO | Sodium laureth sulfate | 14.2 |
| LAMESOFT ® PO 65 | Coco-Glucoside (and) Glyceryl Oleate | 5 |
| Dow Corning 193 | Dimethicole Copolyol | 1 |
| PLANTACARE ® PS 10 | Sodium Laureth Sulfate (and) Lauryl Polyglucose | 0.5 |
| Perfume oil composition | Perfume | 0.5 |
| Kathon CG | Methylchloroisothiazolinone (and) Methylisothiazolinone | 0.05 |
| Water, de-ionized | Aqua | ad 100 |
| Hexylen Glycol (Elf Atochem) | Humectant | 3 |
| UCARE Polymer JR 400 | Polyquaternium-10 | 0.5 |
| pH: 5.5 | | |
| Viscosity: >100 mPas | | |

Self foaming bodywash 2 corresponds to self foaming bodywash, where the perfume oil composition 1B is replaced by the same amount of the perfume oil composition 2B.

Self foaming bodywash 3 corresponds to self foaming bodywash 1, where the perfume oil composition 1B is replaced by the same amount of the perfume oil composition 3.

Self foaming bodywash 4 corresponds to self foaming bodywash 1, where the perfume oil composition 1B is replaced by the same amount of the perfume oil composition 4.

Self foaming bodywash 5 corresponds to self foaming bodywash 1, where the perfume oil composition 1B is replaced by the same amount of the perfume oil composition 5.

Self foaming bodywash 6 corresponds to self foaming bodywash 1, where the perfume oil composition 1B is replaced by the same amount of the perfume oil composition 6.

Self foaming bodywash 7 corresponds to self foaming bodywash 1, where the perfume oil composition 1B is replaced by the same amount of the perfume oil composition 7.

Self foaming bodywash 8 corresponds to self foaming bodywash 1, where the perfume oil composition 1B is replaced by the same amount of the perfume oil composition 8.

Self foaming bodywash 9 corresponds to self foaming bodywash 1, where the perfume oil composition 1B is replaced by the same amount of the perfume oil composition 9.

Self foaming bodywash 10 corresponds to self foaming bodywash 1, where the perfume oil composition 1B is replaced by the same amount of the perfume oil composition 10.

Self foaming bodywash 11 corresponds to self foaming bodywash 1, where the perfume oil composition 1B is replaced by the same amount of the perfume oil composition 11.

Self foaming bodywash 12 corresponds to self foaming bodywash 1, where the perfume oil composition 1B is replaced by the same amount of the perfume oil composition 12.

Self foaming bodywash 13 corresponds to self foaming bodywash 1, where the perfume oil composition 1B is replaced by the same amount of the perfume oil composition 13.

Self foaming bodywash 14 corresponds to self foaming bodywash 1, where the perfume oil composition 1B is replaced by the same amount of the perfume oil composition 14.

Self foaming bodywash 15 corresponds to self foaming bodywash 1, where the perfume oil composition 1B is replaced by the same amount of the perfume oil composition 15.

Self foaming bodywash 16 corresponds to self foaming bodywash 1, where the perfume oil composition 1B is replaced by the same amount of the perfume oil composition 16.

TABLE 12

Sprayable sun care emulsion 1
Sprayable Sun Care Emulsion

| Component | INCI | amount |
|---|---|---|
| EMULGADE ® SE-PF | Glyceryl Stearate (and) Ceteareth-20 (and) Ceteareth-12 (and) Cetearyl Alcohol (and) Cetyl Palmitate | 7.8% |
| EUMULGIN ® B3 | Ceteareth-30 | 4.2% |
| CETIOL ® CC | Dicaprylyl Carbonate | 5.0% |
| CETIOL ® OE | Dicaprylyl Ether | 5.0% |
| Neo Heliopan BB (Haarmann&Reimer) | | 4.5% |
| Neo Heliopan AV (Haarmann&Reimer) | | 7.5% |
| Neo Heliopan 357 (Haarmann& Reimer) | | 2.0% |
| Water, de-ionized | | ad 100 |
| Perfume oil composition 1B | Perfume | 0.05 |
| Eumulgin ® HRE 60 | PEG-60 Hydrogenated Castor Oil | 1.2 |
| pH | | 5.5 |

Viscosity (mPas), RVF spindle 2, 20° C., 50 rpm < 100

Sprayable sun care emulsion 2 corresponds to sprayable sun care emulsion 1, where the perfume oil composition 1B is replaced by the same amount of the perfume oil composition 2B.

Sprayable sun care emulsion 3 corresponds to sprayable sun care emulsion 1, where the perfume oil composition 1B is replaced by the same amount of perfume oil composition 3.

Sprayable sun care emulsion 4 corresponds to sprayable sun care emulsion 1, where the perfume oil composition 1B is replaced by the same amount of the perfume oil composition 4.

Sprayable sun care emulsion 5 corresponds to sprayable sun care emulsion 1, where the perfume oil composition 1B is replaced by the same amount of the perfume oil composition 5.

Sprayable sun care emulsion 6 corresponds to sprayable sun care emulsion 1, where the perfume oil composition 1B is replaced by the same amount of the perfume oil composition 6.

Sprayable sun care emulsion 7 corresponds to sprayable sun care emulsion 1, where the perfume oil composition 1B is replaced by the same amount of the perfume oil composition 7.

Sprayable sun care emulsion 8 corresponds to sprayable sun care emulsion 1, where the perfume oil composition 1B is replaced by the same amount of the perfume oil composition 8.

Sprayable sun care emulsion 9 corresponds to sprayable sun care emulsion 1, where the perfume oil composition 1B is replaced by the same amount of the perfume oil composition 9.

Sprayable sun care emulsion 10 corresponds to sprayable sun care emulsion 1, where the perfume oil composition 1B is replaced by the same amount of the perfume oil composition 10.

Sprayable sun care emulsion 11 corresponds to sprayable sun care emulsion 1, where the perfume oil composition 1B is replaced by the same amount of the perfume oil composition 11.

Sprayable sun care emulsion 12 corresponds to sprayable sun care emulsion 1, where the perfume oil composition 1B is replaced by the same amount of the perfume oil composition 12.

Sprayable sun care emulsion 13 corresponds to sprayable sun care emulsion 1, where the perfume oil composition 1B is replaced by the same amount of the perfume oil composition 13.

Sprayable sun care emulsion 14 corresponds to sprayable sun care emulsion 1, where the perfume oil composition 1B is replaced by the same amount of the perfume oil composition 14.

Sprayable sun care emulsion 15 corresponds to sprayable sun care emulsion 1, where the perfume oil composition 1B is replaced by the same amount of the perfume oil composition 15.

Sprayable sun care emulsion 16 corresponds to sprayable sun care emulsion 1, where the perfume oil composition 1B is replaced by the same amount of the perfume oil composition 16.

TABLE 13

Sprayable sun protection emulsion 1
Sprayable Sun Protection Emulsion

| Component | INCI | amount % |
|---|---|---|
| EMULGADE ® SE-PF | Glyceryl Stearate (and) Ceteareth-20 (and) Ceteareth-12 (and) Cetearyl Alcohol (and) Cetyl Palmitate | 9.0 |
| Eumulgin B3 | Ceteareth-33 | 6.0 |
| CETIOL ® CC | Dicaprylyl Carbonate | 4.0 |
| Eusolex HMS | Homosalate | 7.0 |
| Parsol MCX (Givaudan Roure) | Ethylhexyl Methoxycinnamate | 7.5 |
| Parsol 1789 | Butyl Methoxydibenzoylmethane | 3.0 |
| Neo Heliopan OS | Ethylhexyl Salicylate | 5.0 |
| Preservative | | q.s. |
| Water, de-ionized | | ad 100 |
| perfume oil composition | Perfume | 0.2 |
| Eumulgin ® HRE 60 | PEG-60 Hydrogenated Castor Oil | 1.2 |
| pH-value | 6.2 | |

Sprayable sun protection emulsion 2 corresponds to sprayable sun protection emulsion 1, where the perfume oil composition 1B is replaced by the same amount of the perfume oil composition 2B.

Sprayable sun protection emulsion 3 corresponds to sprayable sun protection emulsion 1, where the perfume oil composition 1B is replaced by the same amount of the perfume oil composition 3.

Sprayable sun protection emulsion 4 corresponds to sprayable sun protection emulsion 1, where the perfume oil composition 1B is replaced by the same amount of the perfume oil composition 4.

Sprayable sun protection emulsion 5 corresponds to sprayable sun protection emulsion 1, where the perfume oil composition 1B is replaced by the same amount of the perfume oil composition 5.

Sprayable sun protection emulsion 6 corresponds to sprayable sun protection emulsion 1, where the perfume oil composition 1B is replaced by the same amount of the perfume oil composition 6.

Sprayable sun protection emulsion 7 corresponds to sprayable sun protection emulsion 1, where the perfume oil composition 1B is replaced by the same amount of the perfume oil composition 7.

Sprayable sun protection emulsion 8 corresponds to sprayable sun protection emulsion 1, where the perfume oil composition 1B is replaced by the same amount of the perfume oil composition 8.

Sprayable sun protection emulsion 9 corresponds to sprayable sun protection emulsion 1, where the perfume oil composition 1B is replaced by the same amount of the perfume oil composition 9.

Sprayable sun protection emulsion 10 corresponds to sprayable sun protection emulsion 1, where the perfume oil composition 1B is replaced by the same amount of the perfume oil composition 10.

Sprayable sun protection emulsion 11 corresponds to sprayable sun protection emulsion 1, where the perfume oil composition 1B is replaced by the same amount of the perfume oil composition 11.

Sprayable sun protection emulsion 12 corresponds to sprayable sun protection emulsion 1, where the perfume oil composition 1B is replaced by the same amount of the perfume oil composition 12.

Sprayable sun protection emulsion 13 corresponds to sprayable sun protection emulsion 1, where the perfume oil composition 1B is replaced by the same amount of the perfume oil composition 13.

Sprayable sun protection emulsion 14 corresponds to sprayable sun protection emulsion 1, where the perfume oil composition 1B is replaced by the same amount of the perfume oil composition 14.

Sprayable sun protection emulsion 15 corresponds to sprayable sun protection emulsion 1, where the perfume oil composition 1B is replaced by the same amount of the perfume oil composition 15.

Sprayable sun protection emulsion 16 corresponds to sprayable sun protection emulsion 1, where the perfume oil composition 1B is replaced by the same amount of the perfume oil composition 16.

TABLE 14

Emollient facial gel 1
Emollient facial Gel

| Component | INCI | amount % |
|---|---|---|
| Water | | Ad 100 |
| HISPAGEL ® 200 | Glycerin (and) Glyceryl Polyacrylate | 10 |

TABLE 14-continued

Emollient facial gel 1
Emollient facial Gel

| Component | INCI | amount % |
|---|---|---|
| CET-OE-Primasponge ®BLUE | | 0.5 |
| PLANTACARE ® PS 10 | Sodium Laureth Sulfate (and) Lauryl Polyglucose | 0.6 |
| Perfume oil composition 1B | | 0.1 |

Emollient facial gel 2 corresponds to emollient facial gel 1, where the perfume oil composition 1B is replaced by the same amount of the perfume oil composition 2B.

Emollient facial gel 3 corresponds to emollient facial gel 1, where the perfume oil composition 1B is replaced by the same amount of the perfume oil composition 3.

Emollient facial gel 4 corresponds to emollient facial gel 1, where the perfume oil composition 1B is replaced by the same amount of the perfume oil composition 4.

Emollient facial gel 5 corresponds to emollient facial gel 1, where the perfume oil composition 1B is replaced by the same amount of the perfume oil composition 5.

Emollient facial gel 6 corresponds to emollient facial gel 1, where the perfume oil composition 1B is replaced by the same amount of the perfume oil composition 6.

Emollient facial gel 7 corresponds to emollient facial gel 1, where the perfume oil composition 1B is replaced by the same amount of the perfume oil composition 7.

Emollient facial gel 8 corresponds to emollient facial gel 1, where the perfume oil composition 1B is replaced by the same amount of the perfume oil composition 8.

Emollient facial gel 9 corresponds to emollient facial gel 1, where the perfume oil composition 1B is replaced by the same amount of the perfume oil composition 9.

Emollient facial gel 10 corresponds to emollient facial gel 1, where the perfume oil composition 1B is replaced by the same amount of the perfume oil composition 10.

Emollient facial gel 11 corresponds to emollient facial gel 1, where the perfume oil composition 1B is replaced by the same amount of the perfume oil composition 11.

Emollient facial gel 12 corresponds to emollient facial gel 1, where the perfume oil composition 1B is replaced by the same amount of the perfume oil composition 12.

Emollient facial gel 13 corresponds to emollient facial gel 1, where the perfume oil composition 1B is replaced by the same amount of the perfume oil composition 13.

Emollient facial gel 14 corresponds to emollient facial gel 1, where the perfume oil composition 1B is replaced by the same amount of the perfume oil composition 14.

Emollient facial gel 15 corresponds to emollient facial gel 1, where the perfume oil composition 1B is replaced by the same amount of the perfume oil composition 15.

Emollient facial gel 16 corresponds to emollient facial gel 1, where the perfume oil composition 1B is replaced by the same amount of the perfume oil composition 16.

TABLE 15

2-phases oil foam bath 1
2-Phases-Oilfoambath

| Component | INCI | amount % b.w. |
|---|---|---|
| PLANTACARE ® PS 10 | Sodium Laureth Sulfate (and) Lauryl Polyglucose | 10 |
| Paraffin oil | (low viscosity) | 20 |
| TEXAPON ® N70 | Sodium Laureth sulfate | 13 |
| DEHYTON ® PK 45 | Cocamidopropyl Betaine | 8 |
| Perfume oil composition 1B | Perfume | 2 |
| Glycerin (86%) | | 5 |
| Preservative | | q.s. |
| Water, de-ionized | | ad 100.0 |
| pH-value | 5.5 | |

2-phases oil foam bath 2 corresponds to 2-phases oil foam bath 1, where the perfume oil composition 1B is replaced by the same amount of the perfume oil composition 2B.

2-phases oil foam bath 3 corresponds to 2-phases oil foam bath 1, where the perfume oil composition 1B is replaced by the same amount of the perfume oil composition 3.

2-phases oil foam bath 4 corresponds to 2-phases oil foam bath 1, where the perfume oil composition 1B is replaced by the same amount of the perfume oil composition 4.

2-phases oil foam bath 5 corresponds to 2-phases oil foam bath 1, where the perfume oil composition 1B is replaced by the same amount of the perfume oil composition 5.

2-phases oil foam bath 6 corresponds to 2-phases oil foam bath 1, where the perfume oil composition 1B is replaced by the same amount of the perfume oil composition 6.

2-phases oil foam bath 7 corresponds to 2-phases oil foam bath 1, where the perfume oil composition 1B is replaced by the same amount of the perfume oil composition 7.

2-phases oil foam bath 8 corresponds to 2-phases oil foam bath 1, where the perfume oil composition 1B is replaced by the same amount of the perfume oil composition 8.

2-phases oil foam bath 9 corresponds to 2-phases oil foam bath 1, where the perfume oil composition 1B is replaced by the same amount of the perfume oil composition 9.

2-phases oil foam bath 10 corresponds to 2-phases oil foam bath 1, where the perfume oil composition 1B is replaced by the same amount of the perfume oil composition 10.

2-phases oil foam bath 11 corresponds to 2-phases oil foam bath 1, where the perfume oil composition 1B is replaced by the same amount of the perfume oil composition 11.

2-phases oil foam bath 12 corresponds to 2-phases oil foam bath 1, where the perfume oil composition 1B is replaced by the same amount of the perfume oil composition 12.

2-phases oil foam bath 13 corresponds to 2-phases oil foam bath 1, where the perfume oil composition 1B is replaced by the same amount of the perfume oil composition 13.

2-phases oil foam bath 14 corresponds to 2-phases oil foam bath 1, where the perfume oil composition 1B is replaced by the same amount of the perfume oil composition 14.

2-phases oil foam bath 15 corresponds to 2-phases oil foam bath 1, where the perfume oil composition 1B is replaced by the same amount of the perfume oil composition 15.

2-phases oil foam bath 16 corresponds to 2-phases oil foam bath 1, where the perfume oil composition 1B is replaced by the same amount of the perfume oil composition 16.

TABLE 16

Shampoos 1, 2, 3 and 4

| Component | INCI | Conc. | Shampoo 1 | Shampoo 2 | Shampoo 3 | Shampoo 4 |
|---|---|---|---|---|---|---|
| | | | | % b.w. | | |
| Texapon N70 | Sodium Laureth Sulfate | 70% | 12.9 | 12.9 | 14.3 | 14.3 |
| Dehyton PK45 | Cocamidopropyl Betaine | 44-46% | 5.4 | 5.4 | 5.4 | 5.4 |
| Plantacare 818UP | Coco-Glucoside | 51-53% | 2.0 | 2.0 | — | — |
| PLANTACARE® PS 10 | Sodium Laureth Sulfate (and) Lauryl Polyglucose | 33% | 6.0 | 18.0 | 21.0 | 30.0 |
| Copherol 1250 C | Tocopheryl Acetate | 100% | 1.0 | — | — | — |
| Cetiol J 600 | Oleyl Erucate | 100% | — | 0.7 | — | 1.0 |
| Almond Oil | Prunus Amygdalus Dulcis (Sweet Almond) Oil | 100% | — | — | 0.3 | — |
| Jaguar C162 | Hydroxypropyl Guar Hydroxypropyltrimonium Chloride | 100% | 0.2 | 0.2 | — | — |
| Jaguar Excel | Guar Hydroxypropyltrimonium Chloride | 100% | — | — | 0.25 | 0.25 |
| Arlypon TT | PEG/PPG-120/10 Trimethylolpropane Trioleate (and) Laureth-2 | 40-50% 40-50% | 1.0 | 2.0 | 1.0 | 2.0 |
| Perfume oil composition 1B | Fragrance | 100% | 0.3 | 0.3 | 0.3 | 0.3 |
| Na-Benzoate | Sodium Benzoate | 100% | 0.5 | 0.5 | 0.5 | 0.5 |
| Citric Acid | Citric Acid | 50% | q.s. | q.s. | q.s. | q.s. |
| NaCl | Sodium Chloride | 100% | q.s. | q.s. | q.s. | q.s. |
| Water | Water | 100% | 70.7 | 49.0 | 56.95 | 46.25 |
| pH value | | | 5.0 | 4.9 | 5.2 | 5.1 |
| Viscosity [mPas] | | | 5600 | 3100 | 4600 | 2500 |

TABLE 17

Shampoos 5, 6, 7 and 8

| Component | INCI | Conc. | Shampoo 5 | Shampoo 6 | Shampoo 7 | Shampoo 8 |
|---|---|---|---|---|---|---|
| | | | | % b.w. | | |
| Sulfopon 1216 G | Sodium Coco-Sulfate | 90-95% | — | — | 12.8 | — |
| Texapon ALS Benz | Ammonium Lauryl Sulfate | 27-28% | — | — | — | 32.0 |
| Plantacare 1200UP | Lauryl Glucoside | 51-53% | 15.0 | — | — | — |
| Plantacare 2000UP | Decyl Glucoside | 51-55% | — | — | — | 6.0 |
| Plantacare 818UP | Coco-Glucoside | 51-53% | — | 30.0 | 20.4 | — |
| Plantacare 810UP | Caprylyl/Capryl Glucoside | 62-65% | 12.0 | — | — | — |
| Jaguar Excel | Guar Hydroxypropyltrimonium Chloride | 100% | 0.2 | 0.25 | 0.2 | 0.3 |
| Dehyton PK45 | Cocamidopropyl Betaine | 44-46% | — | — | — | 11.0 |
| Lamesoft PO65 | Coco-Glucoside (and) Glyceryl Oleate water | 15-25 10-20 62-67 | 28.5-34% | 2.0 | 2.0 | 2.0 | 3.0 |
| Euperlan Green | Lauryl Glucoside (and) Stearyl Citrate water | 15-25 15-25 55-65 | 38-44% | — | — | 2.0 |
| Gluadin WLM Benz | Hydrolyzed Wheat Protein | 21-24% | — | 0.5 | 1.0 | — |
| PLANTACARE® PS 10 | Sodium Laureth Sulfate (and) Lauryl Polyglucose | 33% | 6.0 | 15.0 | 7.5 | 10.5 |

TABLE 17-continued

Shampoos 5, 6, 7 and 8

| Component | INCI | Conc. | Shampoo 5 | 6 | 7 | 8 |
|---|---|---|---|---|---|---|
| | | | | % b.w. | | |
| Copherol 1250 C | Tocopheryl Acetate | 100% | 0.25 | — | — | — |
| Cetiol J 600 | Oleyl Erucate | 100% | — | 0.3 | — | — |
| Almond Oil | Prunus Amygdalus Dulcis (Sweet Almond) Oil | 100% | — | — | 0.2 | 0.25 |
| Keltrol CG-SFT | Xanthan Gum | 100% | 1.0 | 1.0 | | |
| Perfume oil composition 1B | Fragrance | 100% | 0.25 | 0.25 | 0.25 | 0.25 |
| Na-Benzoate | Sodium Benzoate | 100% | 0.5 | 0.5 | 0.5 | 0.5 |
| Citric Acid | Citric Acid | 50% | q.s. | q.s. | q.s. | q.s. |
| NaCl | Sodium Chloride | 100% | q.s. | q.s. | q.s. | q.s. |
| Floral water | Floral water | 100% | — | — | — | 10,0 |
| Water | Water | 100% | 62.8 | 50.2 | 55.15 | 24.2 |
| pH value | | | 5.1 | 5.0 | 5.3 | 4.8 |
| Viscosity [mPas] | | | 6200 | 4600 | 6800 | 5800 |
| Density | g/cm³ | | | | | 1.028 |

Shampoo 9 corresponds to shampoo 1, where the perfume oil composition 1B is replaced by the same amount of the perfume oil composition 2B.

Shampoo 10 corresponds to shampoo 2, where the perfume oil composition 1B is replaced by the same amount of the perfume oil composition 2B.

Shampoo 11 corresponds to shampoo 3, where the perfume oil composition 1B is replaced by the same amount of the perfume oil composition 2B.

Shampoo 12 corresponds to shampoo 4, where the perfume oil composition 1B is replaced by the same amount of the perfume oil composition 2B.

Shampoo 13 corresponds to shampoo 5, where the perfume oil composition 1B is replaced by the same amount of the perfume oil composition 2B.

Shampoo 14 corresponds to shampoo 6, where the perfume oil composition 1B is replaced by the same amount of the perfume oil composition 2B.

Shampoo 15 corresponds to shampoo 7, where the perfume oil composition 1B is replaced by the same amount of the perfume oil composition 2B.

Shampoo 16 corresponds to shampoo 8, where the perfume oil composition 1B is replaced by the same amount of the perfume oil composition 2B.

Shampoo 17 corresponds to shampoo 1, where the perfume oil composition 1B is replaced by the same amount of the perfume oil composition 3.

Shampoo 18 corresponds to shampoo 2, where the perfume oil composition 1B is replaced by the same amount of the perfume oil composition 3.

Shampoo 19 corresponds to shampoo 3, where the perfume oil composition 1B is replaced by the same amount of the perfume oil composition 3.

Shampoo 20 corresponds to shampoo 4, where the perfume oil composition 1B is replaced by the same amount of the perfume oil composition 3.

Shampoo 21 corresponds to shampoo 5, where the perfume oil composition 1B is replaced by the same amount of the perfume oil composition 3.

Shampoo 22 corresponds to shampoo 6, where the perfume oil composition 1B is replaced by the same amount of the perfume oil composition 3.

Shampoo 23 corresponds to shampoo 7, where the perfume oil composition 1B is replaced by the same amount of the perfume oil composition 3.

Shampoo 24 corresponds to shampoo 8, where the perfume oil composition 1B is replaced by the same amount of the perfume oil composition 3.

Shampoo 25 corresponds to shampoo 1, where the perfume oil composition 1B is replaced by the same amount of the perfume oil composition 4.

Shampoo 26 corresponds to shampoo 2, where the perfume oil composition 1B is replaced by the same amount of the perfume oil composition 4.

Shampoo 27 corresponds to shampoo 3, where the perfume oil composition 1B is replaced by the same amount of the perfume oil composition 4.

Shampoo 28 corresponds to shampoo 4, where the perfume oil composition 1B is replaced by the same amount of the perfume oil composition 4.

Shampoo 29 corresponds to shampoo 5, where the perfume oil composition 1B is replaced by the same amount of the perfume oil composition 4.

Shampoo 30 corresponds to shampoo 6, where the perfume oil composition 1B is replaced by the same amount of the perfume oil composition 4.

Shampoo 31 corresponds to shampoo 7, where the perfume oil composition 1B is replaced by the same amount of the perfume oil composition 4.

Shampoo 32 corresponds to shampoo 8, where the perfume oil composition 1B is replaced by the same amount of the perfume oil composition 4.

Shampoo 33 corresponds to shampoo 1, where the perfume oil composition 1B is replaced by the same amount of the perfume oil composition 5.

Shampoo 34 corresponds to shampoo 2, where the perfume oil composition 1B is replaced by the same amount of the perfume oil composition 5.

Shampoo 35 corresponds to shampoo 3, where the perfume oil composition 1B is replaced by the same amount of the perfume oil composition 5.

Shampoo 36 corresponds to shampoo 4, where the perfume oil composition 1B is replaced by the same amount of the perfume oil composition 5.

Shampoo 37 corresponds to shampoo 5, where the perfume oil composition 1B is replaced by the same amount of the perfume oil composition 5.

Shampoo 38 corresponds to shampoo 6, where the perfume oil composition 1B is replaced by the same amount of the perfume oil composition 5.

Shampoo 39 corresponds to shampoo 7, where the perfume oil composition 1B is replaced by the same amount of the perfume oil composition 5.

Shampoo 40 corresponds to shampoo 8, where the perfume oil composition 1B is replaced by the same amount of the perfume oil composition 5.

Shampoo 41 corresponds to shampoo 1, where the perfume oil composition 1B is replaced by the same amount of the perfume oil composition 6.

Shampoo 42 corresponds to shampoo 2, where the perfume oil composition 1B is replaced by the same amount of the perfume oil composition 6.

Shampoo 43 corresponds to shampoo 3, where the perfume oil composition 1B is replaced by the same amount of the perfume oil composition 6.

Shampoo 44 corresponds to shampoo 4, where the perfume oil composition 1B is replaced by the same amount of the perfume oil composition 6.

Shampoo 45 corresponds to shampoo 5, where the perfume oil composition 1B is replaced by the same amount of the perfume oil composition 6.

Shampoo 46 corresponds to shampoo 6, where the perfume oil composition 1B is replaced by the same amount of the perfume oil composition 6.

Shampoo 47 corresponds to shampoo 7, where the perfume oil composition 1B is replaced by the same amount of the perfume oil composition 6.

Shampoo 48 corresponds to shampoo 8, where the perfume oil composition 1B is replaced by the same amount of the perfume oil composition 6.

Shampoo 49 corresponds to shampoo 1, where the perfume oil composition 1B is replaced by the same amount of the perfume oil composition 7.

Shampoo 50 corresponds to shampoo 2, where the perfume oil composition 1B is replaced by the same amount of the perfume oil composition 7.

Shampoo 51 corresponds to shampoo 3, where the perfume oil composition 1B is replaced by the same amount of the perfume oil composition 7.

Shampoo 52 corresponds to shampoo 4, where the perfume oil composition 1B is replaced by the same amount of the perfume oil composition 7.

Shampoo 53 corresponds to shampoo 5, where the perfume oil composition 1B is replaced by the same amount of the perfume oil composition 7.

Shampoo 54 corresponds to shampoo 6, where the perfume oil composition 1B is replaced by the same amount of the perfume oil composition 7.

Shampoo 55 corresponds to shampoo 7, where the perfume oil composition 1B is replaced by the same amount of the perfume oil composition 7.

Shampoo 56 corresponds to shampoo 8, where the perfume oil composition 1B is replaced by the same amount of the perfume oil composition 7.

Shampoo 57 corresponds to shampoo 1, where the perfume oil composition 1B is replaced by the same amount of the perfume oil composition 8.

Shampoo 58 corresponds to shampoo 2, where the perfume oil composition 1B is replaced by the same amount of the perfume oil composition 8.

Shampoo 59 corresponds to shampoo 3, where the perfume oil composition 1B is replaced by the same amount of the perfume oil composition 8.

Shampoo 60 corresponds to shampoo 4, where the perfume oil composition 1B is replaced by the same amount of the perfume oil composition 8.

Shampoo 61 corresponds to shampoo 5, where the perfume oil composition 1B is replaced by the same amount of the perfume oil composition 8.

Shampoo 62 corresponds to shampoo 6, where the perfume oil composition 1B is replaced by the same amount of the perfume oil composition 8.

Shampoo 63 corresponds to shampoo 7, where the perfume oil composition 1B is replaced by the same amount of the perfume oil composition 8.

Shampoo 64 corresponds to shampoo 8, where the perfume oil composition 1B is replaced by the same amount of the perfume oil composition 8.

Shampoo 65 corresponds to shampoo 1, where the perfume oil composition 1B is replaced by the same amount of the perfume oil composition 9.

Shampoo 66 corresponds to shampoo 2, where the perfume oil composition 1B is replaced by the same amount of the perfume oil composition 9.

Shampoo 67 corresponds to shampoo 3, where the perfume oil composition 1B is replaced by the same amount of the perfume oil composition 9.

Shampoo 68 corresponds to shampoo 4, where the perfume oil composition 1B is replaced by the same amount of the perfume oil composition 9.

Shampoo 69 corresponds to shampoo 5, where the perfume oil composition 1B is replaced by the same amount of the perfume oil composition 9.

Shampoo 70 corresponds to shampoo 6, where the perfume oil composition 1B is replaced by the same amount of the perfume oil composition 9.

Shampoo 71 corresponds to shampoo 7, where the perfume oil composition 1B is replaced by the same amount of the perfume oil composition 9.

Shampoo 72 corresponds to shampoo 8, where the perfume oil composition 1B is replaced by the same amount of the perfume oil composition 9.

Shampoo 73 corresponds to shampoo 1, where the perfume oil composition 1B is replaced by the same amount of the perfume oil composition 10.

Shampoo 74 corresponds to shampoo 2, where the perfume oil composition 1B is replaced by the same amount of the perfume oil composition 10.

Shampoo 75 corresponds to shampoo 3, where the perfume oil composition 1B is replaced by the same amount of the perfume oil composition 10.

Shampoo 76 corresponds to shampoo 4, where the perfume oil composition 1B is replaced by the same amount of the perfume oil composition 10.

Shampoo 77 corresponds to shampoo 5, where the perfume oil composition 1B is replaced by the same amount of the perfume oil composition 10.

Shampoo 78 corresponds to shampoo 6, where the perfume oil composition 1B is replaced by the same amount of the perfume oil composition 10.

Shampoo 79 corresponds to shampoo 7, where the perfume oil composition 1B is replaced by the same amount of the perfume oil composition 10.

Shampoo 80 corresponds to shampoo 8, where the perfume oil composition 1B is replaced by the same amount of the perfume oil composition 10.

Shampoo 81 corresponds to shampoo 1, where the perfume oil composition 1B is replaced by the same amount of the perfume oil composition 11.

Shampoo 82 corresponds to shampoo 2, where the perfume oil composition 1B is replaced by the same amount of the perfume oil composition 11.

Shampoo 83 corresponds to shampoo 3, where the perfume oil composition 1B is replaced by the same amount of the perfume oil composition 11.

Shampoo 84 corresponds to shampoo 4, where the perfume oil composition 1B is replaced by the same amount of the perfume oil composition 11.

Shampoo 85 corresponds to shampoo 5, where the perfume oil composition 1B is replaced by the same amount of the perfume oil composition 11.

Shampoo 86 corresponds to shampoo 6, where the perfume oil composition 1B is replaced by the same amount of the perfume oil composition 11.

Shampoo 87 corresponds to shampoo 7, where the perfume oil composition 1B is replaced by the same amount of the perfume oil composition 11.

Shampoo 88 corresponds to shampoo 8, where the perfume oil composition 1B is replaced by the same amount of the perfume oil composition 11.

Shampoo 89 corresponds to shampoo 1, where the perfume oil composition 1B is replaced by the same amount of the perfume oil composition 12.

Shampoo 90 corresponds to shampoo 2, where the perfume oil composition 1B is replaced by the same amount of the perfume oil composition 12.

Shampoo 91 corresponds to shampoo 3, where the perfume oil composition 1B is replaced by the same amount of the perfume oil composition 12.

Shampoo 92 corresponds to shampoo 4, where the perfume oil composition 1B is replaced by the same amount of the perfume oil composition 12.

Shampoo 93 corresponds to shampoo 5, where the perfume oil composition 1B is replaced by the same amount of the perfume oil composition 12.

Shampoo 94 corresponds to shampoo 6, where the perfume oil composition 1B is replaced by the same amount of the perfume oil composition 12.

Shampoo 95 corresponds to shampoo 7, where the perfume oil composition 1B is replaced by the same amount of the perfume oil composition 12.

Shampoo 96 corresponds to shampoo 8, where the perfume oil composition 1B is replaced by the same amount of the perfume oil composition 12.

Shampoo 97 corresponds to shampoo 1, where the perfume oil composition 1B is replaced by the same amount of the perfume oil composition 13.

Shampoo 98 corresponds to shampoo 2, where the perfume oil composition 1B is replaced by the same amount of the perfume oil composition 13.

Shampoo 99 corresponds to shampoo 3, where the perfume oil composition 1B is replaced by the same amount of the perfume oil composition 13.

Shampoo 100 corresponds to shampoo 4, where the perfume oil composition 1B is replaced by the same amount of the perfume oil composition 13.

Shampoo 101 corresponds to shampoo 5, where the perfume oil composition 1B is replaced by the same amount of the perfume oil composition 13.

Shampoo 102 corresponds to shampoo 6, where the perfume oil composition 1B is replaced by the same amount of the perfume oil composition 13.

Shampoo 103 corresponds to shampoo 7, where the perfume oil composition 1B is replaced by the same amount of the perfume oil composition 13.

Shampoo 104 corresponds to shampoo 8, where the perfume oil composition 1B is replaced by the same amount of the perfume oil composition 13.

Shampoo 105 corresponds to shampoo 1, where the perfume oil composition 1B is replaced by the same amount of the perfume oil composition 14.

Shampoo 106 corresponds to shampoo 2, where the perfume oil composition 1B is replaced by the same amount of the perfume oil composition 14.

Shampoo 107 corresponds to shampoo 3, where the perfume oil composition 1B is replaced by the same amount of the perfume oil composition 14.

Shampoo 108 corresponds to shampoo 4, where the perfume oil composition 1B is replaced by the same amount of the perfume oil composition 14.

Shampoo 109 corresponds to shampoo 5, where the perfume oil composition 1B is replaced by the same amount of the perfume oil composition 14.

Shampoo 110 corresponds to shampoo 6, where the perfume oil composition 1B is replaced by the same amount of the perfume oil composition 14.

Shampoo 111 corresponds to shampoo 7, where the perfume oil composition 1B is replaced by the same amount of the perfume oil composition 14.

Shampoo 112 corresponds to shampoo 8, where the perfume oil composition 1B is replaced by the same amount of the perfume oil composition 14.

Shampoo 113 corresponds to shampoo 1, where the perfume oil composition 1B is replaced by the same amount of the perfume oil composition 15.

Shampoo 114 corresponds to shampoo 2, where the perfume oil composition 1B is replaced by the same amount of the perfume oil composition 15.

Shampoo 115 corresponds to shampoo 3, where the perfume oil composition 1B is replaced by the same amount of the perfume oil composition 15.

Shampoo 116 corresponds to shampoo 4, where the perfume oil composition 1B is replaced by the same amount of the perfume oil composition 15.

Shampoo 117 corresponds to shampoo 5, where the perfume oil composition 1B is replaced by the same amount of the perfume oil composition 15.

Shampoo 118 corresponds to shampoo 6, where the perfume oil composition 1B is replaced by the same amount of the perfume oil composition 15.

Shampoo 119 corresponds to shampoo 7, where the perfume oil composition 1B is replaced by the same amount of the perfume oil composition 15.

Shampoo 120 corresponds to shampoo 8, where the perfume oil composition 1B is replaced by the same amount of the perfume oil composition 15.

Shampoo 121 corresponds to shampoo 1, where the perfume oil composition 1B is replaced by the same amount of the perfume oil composition 16.

Shampoo 122 corresponds to shampoo 2, where the perfume oil composition 1B is replaced by the same amount of the perfume oil composition 16.

Shampoo 123 corresponds to shampoo 3, where the perfume oil composition 1B is replaced by the same amount of the perfume oil composition 16.

Shampoo 124 corresponds to shampoo 4, where the perfume oil composition 1B is replaced by the same amount of the perfume oil composition 16.

Shampoo 125 corresponds to shampoo 5, where the perfume oil composition 1B is replaced by the same amount of the perfume oil composition 16.

Shampoo 126 corresponds to shampoo 6, where the perfume oil composition 1B is replaced by the same amount of the perfume oil composition 16.

Shampoo 127 corresponds to shampoo 7, where the perfume oil composition 1B is replaced by the same amount of the perfume oil composition 16.

Shampoo 128 corresponds to shampoo 8, where the perfume oil composition 1B is replaced by the same amount of the perfume oil composition 16.

TABLE 18

Shower bath 1, 2, 3 and 4

| Component | INCI | Conc. | | Shower bath 1 | 2 % b.w. | 3 | 4 |
|---|---|---|---|---|---|---|---|
| Plantapon SF | Sodium Cocoamphoacetate (and) Glycerin (and) Lauryl Glucoside (and) Sodium Cocoyl Glutamate (and) Sodium Lauryl Glucose Carboxylate water | 10-20 5-15 5-15 5 5 48-58 | 42-52% | 45.0 | 50.0 | 48.0 | 44.0 |
| Lamesoft PO65 | Coco-Glucoside (and) Glyceryl Oleate water | 15-25 10-20 62-67 | 28.5-34% | 2.0 | 2.0 | 2.0 | 3.0 |
| Euperlan Green | Lauryl Glucoside (and) Stearyl Citrate water | 15-25 15-25 55-65 | 38-44% | — | — | — | 2.0 |
| Gluadin WLM Benz | Hydrolyzed Wheat Protein | | 21-24% | — | — | 1.0 | 0.5 |
| Keltrol CG-SFT | Xanthan Gum | | 100% | 1.0 | 0.5 | — | — |
| PLANTACARE ® PS 10 | Sodium Laureth Sulfate (and) Lauryl Polyglucose | | 33% | 4.5 | 6.0 | 10.5 | 7.5 |
| Copherol1250 C | Tocopheryl Acetate | | 100% | 0.1 | — | — | — |
| Cetiol J 600 | Oleyl Erucate | | 100% | — | 0.2 | — | — |
| Almond Oil | Prunus Amygdalus Dulcis (Sweet Almond) Oil | | 100% | — | — | 0.15 | 0.1 |
| Perfume oil composition1B | Fragrance | | 100% | 0.25 | 0.25 | 0.25 | 0.25 |
| Na-Benzoate | Sodium Benzoate | | 100% | 0.5 | 0.5 | 0.5 | 0.5 |
| Citric Acid | Citric Acid | | 50% | q.s. | q.s. | q.s. | q.s. |
| Water | Water | | 100% | 46.65 | 40.55 | 37.6 | 42.15 |
| pH value | | | | 5.1 | 4.7 | 4.9 | 4.9 |
| Viscosity [mPas] | | | | 4200 | 4600 | 2900 | 2800 |
| Density | g/cm$^3$ | | | | | | 1.039 |

TABLE 19

Shower bath 5, 6, 7 and 8

| Component | INCI | Conc. | Shower bath 5 | 6 % b.w. | 7 | 8 |
|---|---|---|---|---|---|---|
| Texapon N70 | Sodium Laureth Sulfate | 70% | 12.9 | 12.9 | 14.3 | 14.3 |
| Dehyton PK45 | Cocamidopropyl Betaine | 44-46% | 5.4 | 5.4 | 5.4 | 5.4 |
| Plantacare 818UP | Coco-Glucoside | 51-53% | 2.0 | 2.0 | — | — |
| PLANTACARE ® PS 10 | Sodium Laureth Sulfate (and) Lauryl Polyglucose | 33% | 9.0 | 9.0 | 10.5 | 10.5 |
| DC 245 | Cyclopentasiloxane | 100% | 1.0 | — | 1.1 | — |
| Synfluid PAO2 | Hydrogenated Didecene | 100% | — | 0.8 | — | 1.0 |
| Jaguar C162 | Hydroxypropyl Guar Hydroxypropyltrimonium Chloride | 100% | 0.2 | 0.2 | — | — |
| AquaCAT CG518 | Guar Hydroxypropyltrimonium Chloride | 10% | — | — | 2.5 | 2.5 |

TABLE 19-continued

Shower bath 5, 6, 7 and 8

| Component | INCI | Conc. | Shower bath 5 | 6 % b.w. | 7 | 8 |
|---|---|---|---|---|---|---|
| Arlypon TT | PEG/PPG-120/10 Trimethylolpropane Trioleate (and) Laureth-2 | 40-50% 40-50% | 1.0 | 1.5 | 1.0 | 1.5 |
| Perfume oil composition 1B | Fragrance | 100% | 0.3 | 0.3 | 0.3 | 0.3 |
| Na-Benzoate | Sodium Benzoate | 100% | 0.5 | 0.5 | 0.5 | 0.5 |
| Citric Acid | Citric Acid | 50% | q.s. | q.s. | q.s. | q.s. |
| NaCl | Sodium Chloride | 100% | q.s. | q.s. | q.s. | q.s. |
| Water | Water | 100% | 67.7 | 67.4 | 64.4 | 64.0 |
| pH value | | | 5.0 | 4.9 | 5.2 | 5.1 |
| Viscosity [mPas] | | | 6600 | 8100 | 6900 | 9300 |

Shower bath 9 corresponds to shower bath 1, where the perfume oil composition 1B is replaced by the same amount of the perfume oil composition 2B.

Shower bath 10 corresponds to shower bath 2, where the perfume oil composition 1B is replaced by the same amount of the perfume oil composition 2B.

Shower bath 11 corresponds to shower bath 3, where the perfume oil composition 1B is replaced by the same amount of the perfume oil composition 2B.

Shower bath 12 corresponds to shower bath 4, where the perfume oil composition 1B is replaced by the same amount of the perfume oil composition 2B.

Shower bath 13 corresponds to shower bath 5, where the perfume oil composition 1B is replaced by the same amount of the perfume oil composition 2B.

Shower bath 14 corresponds to shower bath 6, where the perfume oil composition 1B is replaced by the same amount of the perfume oil composition 2B.

Shower bath 15 corresponds to shower bath 7, where the perfume oil composition 1B is replaced by the same amount of the perfume oil composition 2B.

Shower bath 16 corresponds to shower bath 8, where the perfume oil composition 1B is replaced by the same amount of the perfume oil composition 2B.

Shower bath 17 corresponds to shower bath 1, where the perfume oil composition 1B is replaced by the same amount of the perfume oil composition 3.

Shower bath 18 corresponds to shower bath 2, where the perfume oil composition 1B is replaced by the same amount of the perfume oil composition 3.

Shower bath 19 corresponds to shower bath 3, where the perfume oil composition 1B is replaced by the same amount of the perfume oil composition 3.

Shower bath 20 corresponds to shower bath 4, where the perfume oil composition 1B is replaced by the same amount of the perfume oil composition 3.

Shower bath 21 corresponds to shower bath 5, where the perfume oil composition 1B is replaced by the same amount of the perfume oil composition 3.

Shower bath 22 corresponds to shower bath 6, where the perfume oil composition 1B is replaced by the same amount of the perfume oil composition 3.

Shower bath 23 corresponds to shower bath 7, where the perfume oil composition 1B is replaced by the same amount of the perfume oil composition 3.

Shower bath 24 corresponds to shower bath 8, where the perfume oil composition 1B is replaced by the same amount of the perfume oil composition 3.

Shower bath 25 corresponds to shower bath 1, where the perfume oil composition 1B is replaced by the same amount of the perfume oil composition 4.

Shower bath 26 corresponds to shower bath 2, where the perfume oil composition 1B is replaced by the same amount of the perfume oil composition 4.

Shower bath 27 corresponds to shower bath 3, where the perfume oil composition 1B is replaced by the same amount of the perfume oil composition 4.

Shower bath 28 corresponds to shower bath 4, where the perfume oil composition 1B is replaced by the same amount of the perfume oil composition 4.

Shower bath 29 corresponds to shower bath 5, where the perfume oil composition 1B is replaced by the same amount of the perfume oil composition 4.

Shower bath 30 corresponds to shower bath 6, where the perfume oil composition 1B is replaced by the same amount of the perfume oil composition 4.

Shower bath 31 corresponds to shower bath 7, where the perfume oil composition 1B is replaced by the same amount of the perfume oil composition 4.

Shower bath 32 corresponds to shower bath 8, where the perfume oil composition 1B is replaced by the same amount of the perfume oil composition 4.

Shower bath 33 corresponds to shower bath 1, where the perfume oil composition 1B is replaced by the same amount of the perfume oil composition 5.

Shower bath 34 corresponds to shower bath 2, where the perfume oil composition 1B is replaced by the same amount of the perfume oil composition 5.

Shower bath 35 corresponds to shower bath 3, where the perfume oil composition 1B is replaced by the same amount of the perfume oil composition 5.

Shower bath 36 corresponds to shower bath 4, where the perfume oil composition 1B is replaced by the same amount of the perfume oil composition 5.

Shower bath 37 corresponds to shower bath 5, where the perfume oil composition 1B is replaced by the same amount of the perfume oil composition 5.

Shower bath 38 corresponds to shower bath 6, where the perfume oil composition 1B is replaced by the same amount of the perfume oil composition 5.

Shower bath 39 corresponds to shower bath 7, where the perfume oil composition 1B is replaced by the same amount of the perfume oil composition 5.

Shower bath 40 corresponds to shower bath 8, where the perfume oil composition 1B is replaced by the same amount of the perfume oil composition 5.

Shower bath 41 corresponds to shower bath 1, where the perfume oil composition 1B is replaced by the same amount of the perfume oil composition 6.

Shower bath 42 corresponds to shower bath 2, where the perfume oil composition 1B is replaced by the same amount of the perfume oil composition 6.

Shower bath 43 corresponds to shower bath 3, where the perfume oil composition 1B is replaced by the same amount of the perfume oil composition 6.

Shower bath 44 corresponds to shower bath 4, where the perfume oil composition 1B is replaced by the same amount of the perfume oil composition 6.

Shower bath 45 corresponds to shower bath 5, where the perfume oil composition 1B is replaced by the same amount of the perfume oil composition 6.

Shower bath 46 corresponds to shower bath 6, where the perfume oil composition 1B is replaced by the same amount of the perfume oil composition 6.

Shower bath 47 corresponds to shower bath 7, where the perfume oil composition 1B is replaced by the same amount of the perfume oil composition 6.

Shower bath 48 corresponds to shower bath 8, where the perfume oil composition 1B is replaced by the same amount of the perfume oil composition 6.

Shower bath 49 corresponds to shower bath 1, where the perfume oil composition 1B is replaced by the same amount of the perfume oil composition 7.

Shower bath 50 corresponds to shower bath 2, where the perfume oil composition 1B is replaced by the same amount of the perfume oil composition 7.

Shower bath 51 corresponds to shower bath 3, where the perfume oil composition 1B is replaced by the same amount of the perfume oil composition 7.

Shower bath 52 corresponds to shower bath 4, where the perfume oil composition 1B is replaced by the same amount of the perfume oil composition 7.

Shower bath 53 corresponds to shower bath 5, where the perfume oil composition 1B is replaced by the same amount of the perfume oil composition 7.

Shower bath 54 corresponds to shower bath 6, where the perfume oil composition 1B is replaced by the same amount of the perfume oil composition 7.

Shower bath 55 corresponds to shower bath 7, where the perfume oil composition 1B is replaced by the same amount of the perfume oil composition 7.

Shower bath 56 corresponds to shower bath 8, where the perfume oil composition 1B is replaced by the same amount of the perfume oil composition 7.

Shower bath 57 corresponds to shower bath 1, where the perfume oil composition 1B is replaced by the same amount of the perfume oil composition 8.

Shower bath 58 corresponds to shower bath 2, where the perfume oil composition 1B is replaced by the same amount of the perfume oil composition 8.

Shower bath 59 corresponds to shower bath 3, where the perfume oil composition 1B is replaced by the same amount of the perfume oil composition 8.

Shower bath 60 corresponds to shower bath 4, where the perfume oil composition 1B is replaced by the same amount of the perfume oil composition 8.

Shower bath 61 corresponds to shower bath 5, where the perfume oil composition 1B is replaced by the same amount of the perfume oil composition 8.

Shower bath 62 corresponds to shower bath 6, where the perfume oil composition 1B is replaced by the same amount of the perfume oil composition 8.

Shower bath 63 corresponds to shower bath 7, where the perfume oil composition 1B is replaced by the same amount of the perfume oil composition 8.

Shower bath 64 corresponds to shower bath 8, where the perfume oil composition 1B is replaced by the same amount of the perfume oil composition 8.

Shower bath 65 corresponds to shower bath 1, where the perfume oil composition 1B is replaced by the same amount of the perfume oil composition 9.

Shower bath 66 corresponds to shower bath 2, where the perfume oil composition 1B is replaced by the same amount of the perfume oil composition 9.

Shower bath 67 corresponds to shower bath 3, where the perfume oil composition 1B is replaced by the same amount of the perfume oil composition 9.

Shower bath 68 corresponds to shower bath 4, where the perfume oil composition 1B is replaced by the same amount of the perfume oil composition 9.

Shower bath 69 corresponds to shower bath 5, where the perfume oil composition 1B is replaced by the same amount of the perfume oil composition 9.

Shower bath 70 corresponds to shower bath 6, where the perfume oil composition 1B is replaced by the same amount of the perfume oil composition 9.

Shower bath 71 corresponds to shower bath 7, where the perfume oil composition 1B is replaced by the same amount of the perfume oil composition 9.

Shower bath 72 corresponds to shower bath 8, where the perfume oil composition 1B is replaced by the same amount of the perfume oil composition 9.

Shower bath 73 corresponds to shower bath 1, where the perfume oil composition 1B is replaced by the same amount of the perfume oil composition 10.

Shower bath 74 corresponds to shower bath 2, where the perfume oil composition 1B is replaced by the same amount of the perfume oil composition 10.

Shower bath 75 corresponds to shower bath 3, where the perfume oil composition 1B is replaced by the same amount of the perfume oil composition 10.

Shower bath 76 corresponds to shower bath 4, where the perfume oil composition 1B is replaced by the same amount of the perfume oil composition 10.

Shower bath 77 corresponds to shower bath 5, where the perfume oil composition 1B is replaced by the same amount of the perfume oil composition 10.

Shower bath 78 corresponds to shower bath 6, where the perfume oil composition 1B is replaced by the same amount of the perfume oil composition 10.

Shower bath 79 corresponds to shower bath 7, where the perfume oil composition 1B is replaced by the same amount of the perfume oil composition 10.

Shower bath 80 corresponds to shower bath 8, where the perfume oil composition 1B is replaced by the same amount of the perfume oil composition 10.

Shower bath 81 corresponds to shower bath 1, where the perfume oil composition 1B is replaced by the same amount of the perfume oil composition 11.

Shower bath 82 corresponds to shower bath 2, where the perfume oil composition 1B is replaced by the same amount of the perfume oil composition 11.

Shower bath 83 corresponds to shower bath 3, where the perfume oil composition 1B is replaced by the same amount of the perfume oil composition 11.

Shower bath 84 corresponds to shower bath 4, where the perfume oil composition 1B is replaced by the same amount of the perfume oil composition 11.

Shower bath 85 corresponds to shower bath 5, where the perfume oil composition 1B is replaced by the same amount of the perfume oil composition 11.

Shower bath 86 corresponds to shower bath 6, where the perfume oil composition 1B is replaced by the same amount of the perfume oil composition 11.

Shower bath 87 corresponds to shower bath 7, where the perfume oil composition 1B is replaced by the same amount of the perfume oil composition 11.

Shower bath 88 corresponds to shower bath 8, where the perfume oil composition 1B is replaced by the same amount of the perfume oil composition 11.

Shower bath 89 corresponds to shower bath 1, where the perfume oil composition 1B is replaced by the same amount of the perfume oil composition 12.

Shower bath 90 corresponds to shower bath 2, where the perfume oil composition 1B is replaced by the same amount of the perfume oil composition 12.

Shower bath 91 corresponds to shower bath 3, where the perfume oil composition 1B is replaced by the same amount of the perfume oil composition 12.

Shower bath 92 corresponds to shower bath 4, where the perfume oil composition 1B is replaced by the same amount of the perfume oil composition 12.

Shower bath 93 corresponds to shower bath 5, where the perfume oil composition 1B is replaced by the same amount of the perfume oil composition 12.

Shower bath 94 corresponds to shower bath 6, where the perfume oil composition 1B is replaced by the same amount of the perfume oil composition 12.

Shower bath 95 corresponds to shower bath 7, where the perfume oil composition 1B is replaced by the same amount of the perfume oil composition 12.

Shower bath 96 corresponds to shower bath 8, where the perfume oil composition 1B is replaced by the same amount of the perfume oil composition 12.

Shower bath 97 corresponds to shower bath 1, where the perfume oil composition 1B is replaced by the same amount of the perfume oil composition 13.

Shower bath 98 corresponds to shower bath 2, where the perfume oil composition 1B is replaced by the same amount of the perfume oil composition 13.

Shower bath 99 corresponds to shower bath 3, where the perfume oil composition 1B is replaced by the same amount of the perfume oil composition 13.

Shower bath 100 corresponds to shower bath 4, where the perfume oil composition 1B is replaced by the same amount of the perfume oil composition 13.

Shower bath 101 corresponds to shower bath 5, where the perfume oil composition 1B is replaced by the same amount of the perfume oil composition 13.

Shower bath 102 corresponds to shower bath 6, where the perfume oil composition 1B is replaced by the same amount of the perfume oil composition 13.

Shower bath 103 corresponds to shower bath 7, where the perfume oil composition 1B is replaced by the same amount of the perfume oil composition 13.

Shower bath 104 corresponds to shower bath 8, where the perfume oil composition 1B is replaced by the same amount of the perfume oil composition 13.

Shower bath 105 corresponds to shower bath 1, where the perfume oil composition 1B is replaced by the same amount of the perfume oil composition 14.

Shower bath 106 corresponds to shower bath 2, where the perfume oil composition 1B is replaced by the same amount of the perfume oil composition 14.

Shower bath 107 corresponds to shower bath 3, where the perfume oil composition 1B is replaced by the same amount of the perfume oil composition 14.

Shower bath 108 corresponds to shower bath 4, where the perfume oil composition 1B is replaced by the same amount of the perfume oil composition 14.

Shower bath 109 corresponds to shower bath 5, where the perfume oil composition 1B is replaced by the same amount of the perfume oil composition 14.

Shower bath 110 corresponds to shower bath 6, where the perfume oil composition 1B is replaced by the same amount of the perfume oil composition 14.

Shower bath 111 corresponds to shower bath 7, where the perfume oil composition 1B is replaced by the same amount of the perfume oil composition 14.

Shower bath 112 corresponds to shower bath 8, where the perfume oil composition 1B is replaced by the same amount of the perfume oil composition 14.

Shower bath 113 corresponds to shower bath 1, where the perfume oil composition 1B is replaced by the same amount of the perfume oil composition 15.

Shower bath 114 corresponds to shower bath 2, where the perfume oil composition 1B is replaced by the same amount of the perfume oil composition 15.

Shower bath 115 corresponds to shower bath 3, where the perfume oil composition 1B is replaced by the same amount of the perfume oil composition 15.

Shower bath 116 corresponds to shower bath 4, where the perfume oil composition 1B is replaced by the same amount of the perfume oil composition 15.

Shower bath 117 corresponds to shower bath 5, where the perfume oil composition 1B is replaced by the same amount of the perfume oil composition 15.

Shower bath 118 corresponds to shower bath 6, where the perfume oil composition 1B is replaced by the same amount of the perfume oil composition 15.

Shower bath 119 corresponds to shower bath 7, where the perfume oil composition 1B is replaced by the same amount of the perfume oil composition 15.

Shower bath 120 corresponds to shower bath 8, where the perfume oil composition 1B is replaced by the same amount of the perfume oil composition 15.

Shower bath 121 corresponds to shower bath 1, where the perfume oil composition 1B is replaced by the same amount of the perfume oil composition 16.

Shower bath 122 corresponds to shower bath 2, where the perfume oil composition 1B is replaced by the same amount of the perfume oil composition 16.

Shower bath 123 corresponds to shower bath 3, where the perfume oil composition 1B is replaced by the same amount of the perfume oil composition 16.

Shower bath 124 corresponds to shower bath 4, where the perfume oil composition 1B is replaced by the same amount of the perfume oil composition 16.

Shower bath 125 corresponds to shower bath 5, where the perfume oil composition 1B is replaced by the same amount of the perfume oil composition 16.

Shower bath 126 corresponds to shower bath 6, where the perfume oil composition 1B is replaced by the same amount of the perfume oil composition 16.

Shower bath 127 corresponds to shower bath 7, where the perfume oil composition 1B is replaced by the same amount of the perfume oil composition 16.

Shower bath 128 corresponds to shower bath 8, where the perfume oil composition 1B is replaced by the same amount of the perfume oil composition 16.

TABLE 20

Hydro-alcoholic AP/Deo pump spray

| Component | INCI | amount % |
|---|---|---|
| Ethanol, cosm. | Alcohol | 40.0 |
| water, demin. | Aqua | 37.5 |
| Hydagen CAT | Triethyl Citrate | 2.0 |
| Hydagen DCMF | Chitosan | 10.0 |
| Eumulgin ® HRE 60 | PEG-60 Hydrogenated Castor Oil | 1.5 |
| Chlorhydrol (50% solut.) | Aluminium Chlorohydrate | 8.0 |
| Perfume oil composition 1B | | 1.0 |

Deo pump spray according to table 20, where the perfume oil composition 1B is replaced by the same amount of the perfume oil composition 2B.

Deo pump spray according to table 20, where the perfume oil composition 1B is replaced by the same amount of the perfume oil composition 3.

Deo pump spray according to table 20, where the perfume oil composition 1B is replaced by the same amount of the perfume oil composition 4.

Deo pump spray according to table 20, where the perfume oil composition 1B is replaced by the same amount of the perfume oil composition 5.

Deo pump spray according to table 20, where the perfume oil composition 1B is replaced by the same amount of the perfume oil composition 6.

Deo pump spray according to table 20, where the perfume oil composition 1B is replaced by the same amount of the perfume oil composition 7.

Deo pump spray according to table 20, where the perfume oil composition 1B is replaced by the same amount of the perfume oil composition 8.

Deo pump spray according to table 20, where the perfume oil composition 1B is replaced by the same amount of the perfume oil composition 9.

Deo pump spray according to table 20, where the perfume oil composition 1B is replaced by the same amount of the perfume oil composition 10.

Deo pump spray according to table 20, where the perfume oil composition 1B is replaced by the same amount of the perfume oil composition 11.

Deo pump spray according to table 20, where the perfume oil composition 1B is replaced by the same amount of the perfume oil composition 12.

Deo pump spray according to table 20, where the perfume oil composition 1B is replaced by the same amount of the perfume oil composition 13.

Deo pump spray according to table 20, where the perfume oil composition 1B is replaced by the same amount of the perfume oil composition 14.

Deo pump spray according to table 20, where the perfume oil composition 1B is replaced by the same amount of the perfume oil composition 15.

Deo pump spray according to table 20, where the perfume oil composition 1B is replaced by the same amount of the perfume oil composition 16.

TABLE 21

Aerosol 1

| Component | INCI | amount % |
|---|---|---|
| Ethanol, cosm. | Alcohol | 80.0 |
| water, demin. | Aqua | 16.7 |
| Propylene glycol | Propylene Glycol | 1.0 |
| Eumulgin ® HRE 60 | PEG-60 Hydrogenated Castor Oil | 1.5 |
| alpha-Bisabolol | Bisabolol | 0.05 |
| Triclosan | Triclosan | 0.25 |
| perfume oil composition 1B | | 1.0 |

Aerosol 2 corresponds to aerosol 1, where the perfume oil composition 1B is replaced by the same amount of the perfume oil composition 2B.

Aerosol 3 corresponds to aerosol 1, where the perfume oil composition 1B is replaced by the same amount of the perfume oil composition 3.

Aerosol 4 corresponds to aerosol 1, where the perfume oil composition 1B is replaced by the same amount of the perfume oil composition 4.

Aerosol 5 corresponds to aerosol 1, where the perfume oil composition 1B is replaced by the same amount of the perfume oil composition 5.

Aerosol 6 corresponds to aerosol 1, where the perfume oil composition 1B is replaced by the same amount of the perfume oil composition 6.

Aerosol 7 corresponds to aerosol 1, where the perfume oil composition 1B is replaced by the same amount of the perfume oil composition 7.

Aerosol 8 corresponds to aerosol 1, where the perfume oil composition 1B is replaced by the same amount of the perfume oil composition 8.

Aerosol 9 corresponds to aerosol 1, where the perfume oil composition 1B is replaced by the same amount of the perfume oil composition 9.

Aerosol 10 corresponds to aerosol 1, where the perfume oil composition 1B is replaced by the same amount of the perfume oil composition 10.

Aerosol 11 corresponds to aerosol 1, where the perfume oil composition 1B is replaced by the same amount of the perfume oil composition 11.

Aerosol 12 corresponds to aerosol 1, where the perfume oil composition 1B is replaced by the same amount of the perfume oil composition 12.

Aerosol 13 corresponds to aerosol 1, where the perfume oil composition 1B is replaced by the same amount of the perfume oil composition 13.

Aerosol 14 corresponds to aerosol 1, where the perfume oil composition 1B is replaced by the same amount of the perfume oil composition 14.

Aerosol 15 corresponds to aerosol 1, where the perfume oil composition 1B is replaced by the same amount of the perfume oil composition 15.

Aerosol 16 corresponds to aerosol 1, where the perfume oil composition 1B is replaced by the same amount of the perfume oil composition 16.

TABLE 22

Aqueous/alcoholic AP/Deo roll-on

| Component | INCI | amount % |
|---|---|---|
| Ethanol, cosm. | Alcohol | 40.0 |
| water, demin. | Aqua | 37.0 |
| Hydagen CAT | Triethyl Citrate | 2.0 |
| Hydagen DCMF | Chitosan | 10.0 |
| Eumulgin ® HRE 60 | PEG-60 Hydrogenated Castor Oil | 1.5 |
| Chlorhydrol (50% solut.) | Aluminium Chlorohydarte | 8.0 |
| Klucel M | Hydroxypropylcellulose | 0.5 |
| Perfume oil composition 1B |  | 1.0 |

Aqueous/alcoholic AP/Deo roll-on according to table 22, where the perfume oil composition 1B is replaced by the same amount of the perfume oil composition 2B.

Aqueous/alcoholic AP/Deo roll-on according to table 22, where the perfume oil composition 1B is replaced by the same amount of the perfume oil composition 3.

Aqueous/alcoholic AP/Deo roll-on according to table 22, where the perfume oil composition 1B is replaced by the same amount of the perfume oil composition 4.

Aqueous/alcoholic AP/Deo roll-on according to table 22, where the perfume oil composition 1B is replaced by the same amount of the perfume oil composition 5.

Aqueous/alcoholic AP/Deo roll-on according to table 22, where the perfume oil composition 1B is replaced by the same amount of the perfume oil composition 6.

Aqueous/alcoholic AP/Deo roll-on according to table 22, where the perfume oil composition 1B is replaced by the same amount of the perfume oil composition 7.

Aqueous/alcoholic AP/Deo roll-on according to table 22, where the perfume oil composition 1B is replaced by the same amount of the perfume oil composition 8.

Aqueous/alcoholic AP/Deo roll-on according to table 22, where the perfume oil composition 1B is replaced by the same amount of the perfume oil composition 9.

Aqueous/alcoholic AP/Deo roll-on according to table 22, where the perfume oil composition 1B is replaced by the same amount of the perfume oil composition 10.

Aqueous/alcoholic AP/Deo roll-on according to table 22, where the perfume oil composition 1B is replaced by the same amount of the perfume oil composition 11.

Aqueous/alcoholic AP/Deo roll-on according to table 22, where the perfume oil composition 1B is replaced by the same amount of the perfume oil composition 12.

Aqueous/alcoholic AP/Deo roll-on according to table 22, where the perfume oil composition 1B is replaced by the same amount of the perfume oil composition 13.

Aqueous/alcoholic AP/Deo roll-on according to table 22, where the perfume oil composition 1B is replaced by the same amount of the perfume oil composition 14.

Aqueous/alcoholic AP/Deo roll-on according to table 22, where the perfume oil composition 1B is replaced by the same amount of the perfume oil composition 15.

Aqueous/alcoholic AP/Deo roll-on according to table 22, where the perfume oil composition 1B is replaced by the same amount of the perfume oil composition 16.

TABLE 23

Styling Gel Type "Out of Bed"

| Phase | Component | INCI | % | Function |
|---|---|---|---|---|
| I | Alcool 96% (Prolabo) | Alcohol 96% | 12.00 | Solvent |
|  | Luviskol VA 64 (BASF) | PVPA/A | 4.50 | Styling agent |
|  | Polyox WSR-301 | PEG-90M | 0.25 | Styling agent |
|  | Methocel E4M Premium EP (DOW) | Hydroxypropyl Methylcellulose | 0.60 | Thickener |
|  | DEHYQUART ® L 80 | Dicocoylethyl Hydroxyethylmonium Methosulfate (and) Propylene Glycol | 0.60 | Active agent |
| II. | Eumulgin ® HRE 60 | Hardened castor oil with approx. 60 mol EO | 1.00 | Solubilizer |
|  | CETIOL ® OE | Dicaprylyl Ether | 1.50 | Emollient |
| III. | Water, de-ionized | Aqua | a.d. |  |
| IV. | HISPAGEL ® 200 | Glycerin (and) Glyceryl Polyacrylate | 36.70 | Thickener |
| V. | Perfume oil composition 1B |  | 0.02 |  |
| >> |  | pH-value | 6.8 |  |
| >> |  | Viscosity (mPas) Brookfield RVT 23° C. spindle 5, 10 rpm | 220.000 mPas |  |

Styling gel according to table 23, where the perfume oil composition 1B is replaced by the same amount of the perfume oil composition 2B.

Styling gel according to table 23, where the perfume oil composition 1B is replaced by the same amount of the perfume oil composition 3.

Styling gel according to table 23, where the perfume oil composition 1B is replaced by the same amount of the perfume oil composition 4.

Styling gel according to table 23, where the perfume oil composition 1B is replaced by the same amount of the perfume oil composition 5.

Styling gel according to table 23, where the perfume oil composition 1B is replaced by the same amount of the perfume oil composition 6.

Styling gel according to table 23, where the perfume oil composition 1B is replaced by the same amount of the perfume oil composition 7.

Styling gel according to table 23, where the perfume oil composition 1B is replaced by the same amount of the perfume oil composition 8.

Styling gel according to table 23, where the perfume oil composition 1B is replaced by the same amount of the perfume oil composition 9.

Styling gel according to table 23, where the perfume oil composition 1B is replaced by the same amount of the perfume oil composition 10.

Styling gel according to table 23, where the perfume oil composition 1B is replaced by the same amount of the perfume oil composition 11.

Styling gel according to table 23, where the perfume oil composition 1B is replaced by the same amount of the perfume oil composition 12.

Styling gel according to table 23, where the perfume oil composition 1B is replaced by the same amount of the perfume oil composition 13.

Styling gel according to table 23, where the perfume oil composition 1B is replaced by the same amount of the perfume oil composition 14.

Styling gel according to table 23, where the perfume oil composition 1B is replaced by the same amount of the perfume oil composition 15.

Styling gel according to table 23, where the perfume oil composition 1B is replaced by the same amount of the perfume oil composition 16.

Shaving foam according to table 24, where the perfume oil composition 1B is replaced by the same amount of the perfume oil composition 6.

Shaving foam according to table 24, where the perfume oil composition 1B is replaced by the same amount of the perfume oil composition 7.

Shaving foam according to table 24, where the perfume oil composition 1B is replaced by the same amount of the perfume oil composition 8.

Shaving foam according to table 24, where the perfume oil composition 1B is replaced by the same amount of the perfume oil composition 9.

Shaving foam according to table 24, where the perfume oil composition 1B is replaced by the same amount of the perfume oil composition 10.

Shaving foam according to table 24, where the perfume oil composition 1B is replaced by the same amount of the perfume oil composition 11.

Shaving foam according to table 24, where the perfume oil composition 1B is replaced by the same amount of the perfume oil composition 12.

TABLE 24

Shaving Foam

| Phase | Component | INCI | % | Function |
|---|---|---|---|---|
| | CUTINA ® FS 45 | Stearic Acid (and) Palmitic Acid | 7.6 | Surfactant (foam consistency) |
| | PLANTACARE ® 1200 UP | Lauryl Glucoside | 6.0 | Surfactant (inhibitory effect) |
| | MONOMULS ® 90-0 18 | Glyceryl Oleate | 1.2 | W/O emulsifier (moisturizing) |
| | EUMULGIN ® O20 S | Oleth-20 | 1.2 | O/W-emulsifier (stability) |
| | CETIOL ® CC | Dicaprylyl Carbonate | 2.0 | Emollient (low viscosity) |
| | DEHYQUART ® SP | Quaternium-52 | 0.5 | Surfactant (inhibitor |
| | TEA (99%) | | 4.0 | Neutralizer (for Cutina FS 45) |
| | Glycerin | Glycerin | 3.0 | Humectant |
| | Propylene Glycol | Propylene Glycol | 3.0 | Humectant (low viscosiy) |
| | Emulgin ® HRE 60 | Hardened castor oil with approx. 60 mol EO | 2.0 | Solubilizer |
| | D-Panthenol | Panthenol | 0.2 | Care additive |
| | Phenonip | Phenoxyethanol (and) Parabens | 0.5 | Preservative |
| | Perfume oil composition 1B | | 0.3 | Fragrance |
| | Distilled or Deionized Water | Aqua | ad 100 | |

Shaving foam according to table 24, where the perfume oil composition 1B is replaced by the same amount of the perfume oil composition 2B.

Shaving foam according to table 24, where the perfume oil composition 1B is replaced by the same amount of the perfume oil composition 3.

Shaving foam according to table 24, where the perfume oil composition 1B is replaced by the same amount of the perfume oil composition 4.

Shaving foam according to table 24, where the perfume oil composition 1B is replaced by the same amount of the perfume oil composition 5.

Shaving foam according to table 24, where the perfume oil composition 1B is replaced by the same amount of the perfume oil composition 13.

Shaving foam according to table 24, where the perfume oil composition 1B is replaced by the same amount of the perfume oil composition 14.

Shaving foam according to table 24, where the perfume oil composition 1B is replaced by the same amount of the perfume oil composition 15.

Shaving foam according to table 24, where the perfume oil composition 1B is replaced by the same amount of the perfume oil composition 16.

TABLE 25

Sensitive skin Baby shampoo

| | Ingredients | INCI/Chemistry | % | Function |
|---|---|---|---|---|
| I. | PLANTAPON ® LGC SORB | Sodium Lauryl Glucose Carboxylate (and) Lauryl Glucoside | 28.00 | Surfactant, cleaning |
| | ARLYPON ® TT | PEG/PPG-120/10 Trimethylolpropane Trioleate (and) Laureth-2 | 2.00 | Thickener |
| | DEHYTON ® MC | Sodium Cocoamphoacetate | 6.00 | Surfactant |
| | EUMULGIN ® SML 20 | Polysorbate 20 | 3.00 | Solubilizer |
| | LAMESOFT ® PO 65 | Coco-Glucoside (and) Glyceryl Oleate | 2.20 | Lipid layer enhancer |
| | MELHYDRAN ™ LS 4420 | Honey Extract | 1.00 | Active ingredient |
| | Perfume oil composition 1B | Perfume | 0.20 | Perfume |
| | Dermosoft 1388 (Dr. Straetmans) | Water (and) Glycerin (and) Sodium Levulinate (and) Sodium Anisate | 4.00 | Active ingredient |
| | Water, demin. | Aqua | 53.60 | |

Sensitive skin baby shampoo according to table 25, where the perfume oil composition 1B is replaced by the same amount of the perfume oil composition 2B.

Sensitive skin baby shampoo according to table 25, where the perfume oil composition 1B is replaced by the same amount of the perfume oil composition 3.

Sensitive skin baby shampoo according to table 25, where the perfume oil composition 1B is replaced by the same amount of the perfume oil composition 4.

Sensitive skin baby shampoo according to table 25, where the perfume oil composition 1B is replaced by the same amount of the perfume oil composition 5.

Sensitive skin baby shampoo according to table 25, where the perfume oil composition 1B is replaced by the same amount of the perfume oil composition 6.

Sensitive skin baby shampoo according to table 25, where the perfume oil composition 1B is replaced by the same amount of the perfume oil composition 7.

Sensitive skin baby shampoo according to table 25, where the perfume oil composition 1B is replaced by the same amount of the perfume oil composition 8.

Sensitive skin baby shampoo according to table 25, where the perfume oil composition 1B is replaced by the same amount of the perfume oil composition 9.

Sensitive skin baby shampoo according to table 25, where the perfume oil composition 1B is replaced by the same amount of the perfume oil composition 10.

Sensitive skin baby shampoo according to table 25, where the perfume oil composition 1B is replaced by the same amount of the perfume oil composition 11.

Sensitive skin baby shampoo according to table 25, where the perfume oil composition 1B is replaced by the same amount of the perfume oil composition 12.

Sensitive skin baby shampoo according to table 25, where the perfume oil composition 1B is replaced by the same amount of the perfume oil composition 13.

Sensitive skin baby shampoo according to table 25, where the perfume oil composition 1B is replaced by the same amount of the perfume oil composition 14.

Sensitive skin baby shampoo according to table 25, where the perfume oil composition 1B is replaced by the same amount of the perfume oil composition 15.

Sensitive skin baby shampoo according to table 25, where the perfume oil composition 1B is replaced by the same amount of the perfume oil composition 16.

TABLE 26

Body wash for Sensitive Skin

| | Ingredients | INCI/Chemistry | % | Function |
|---|---|---|---|---|
| I. | Water, demin. | Aqua | 70.90 | |
| | TEXAPON ® N 70 | Sodium Laureth Sulfate | 13.00 | Surfactant |
| | PLANTACARE ® 818 UP | Coco-Glucoside | 3.00 | Surfactant |
| | LAMESOFT ® PO 65 | Coco-Glucoside (and) Glyceryl Oleate | 5.00 | Active, skin conditioning |
| | Perfume oil composition 1B | Fragrance | 0.15 | Perfume |
| | Sodium Benzoate | Sodium Benzoate | 0.55 | Preservative |
| II. | DEHYQUART ® CC7 BZ | Polyquaternium-7 | 2.00 | Active, hair conditioning |
| III. | MELHYDRAN ™ LS 4420 | Honey Extract | 1.00 | Active, moisturizing |
| | ARLYPON ® TT | PEG/PPG-120/10 Trimethylolpropane Trioleate (and) Laureth-2 | 0.50 | Thickener |
| | DEHYTON ® PK 45 | Cocamidopropyl Betaine | 3.80 | Surfactant |
| IV. | Sodium Chloride | Sodium Chloride | 0.10 | Agent, thickening |

Body wash for sensitive skin according to table 26, where the perfume oil composition 1B is replaced by the same amount of the perfume oil composition 2B.

Body wash for sensitive skin according to table 26, where the perfume oil composition 1B is replaced by the same amount of the perfume oil composition 3.

Body wash for sensitive skin according to table 26, where the perfume oil composition 1B is replaced by the same amount of the perfume oil composition 4.

Body wash for sensitive skin according to table 26, where the perfume oil composition 1B is replaced by the same amount of the perfume oil composition 5.

Body wash for sensitive skin according to table 26, where the perfume oil composition 1B is replaced by the same amount of the perfume oil composition 6.

Body wash for sensitive skin according to table 26, where the perfume oil composition 1B is replaced by the same amount of the perfume oil composition 7.

Body wash for sensitive skin according to table 26, where the perfume oil composition 1B is replaced by the same amount of the perfume oil composition 8.

Body wash for sensitive skin according to table 26, where the perfume oil composition 1B is replaced by the same amount of the perfume oil composition 9.

Body wash for sensitive skin according to table 26, where the perfume oil composition 1B is replaced by the same amount of the perfume oil composition 10.

Body wash for sensitive skin according to table 26, where the perfume oil composition 1B is replaced by the same amount of the perfume oil composition 11.

Body wash for sensitive skin according to table 26, where the perfume oil composition 1B is replaced by the same amount of the perfume oil composition 12.

Body wash for sensitive skin according to table 26, where the perfume oil composition 1B is replaced by the same amount of the perfume oil composition 13.

Body wash for sensitive skin according to table 26, where the perfume oil composition 1B is replaced by the same amount of the perfume oil composition 14.

Body wash for sensitive skin according to table 26, where the perfume oil composition 1B is replaced by the same amount of the perfume oil composition 15.

Body wash for sensitive skin according to table 26, where the perfume oil composition 1B is replaced by the same amount of the perfume oil composition 16.

TABLE 27

Gloss Enhancing Shampoo for Sensitive Scalp

| | Ingredients | INCI/Chemistry | % | Function |
|---|---|---|---|---|
| I. | Water, demin. | Aqua | 71.60 | |
| | Luviquat Ultra Care (BASF) | Polyquaternium-44 | 1.50 | Active, hair conditioning |
| II. | Sodium Benzoate | Sodium Benzoate | 0.55 | Preservative |
| III. | TEXAPON ® N 70 | Sodium Laureth Sulfate | 14.30 | Surfactant |
| | DEHYTON ® PK 45 | Cocamidopropyl Betaine | 5.40 | Surfactant |
| | MELHYDRAN ™ LS 4420 | Honey Extract | 1.00 | Active, moisturizing |
| | Perfume oil composition 1B | Fragrance | 0.15 | Perfume |
| IV. | DEHYDOL ® LS 2 DEO N | Laureth-2 | 1.00 | Thickener |
| V. | LAMESOFT ® CARE | PEG-4 Distearyl Ether (and) Sodium Laureth sulfate (and) Distearyl Ether (and) Dicaprylyl Ether | 3.00 | Active, hair conditioning |
| VI. | Sodium Chloride | Sodium Chloride | 1.50 | Agent, thickening |

Gloss enhancing shampoo for sensitive scalp according to table 27, where the perfume oil composition 1B is replaced by the same amount of the perfume oil composition 2B.

Gloss enhancing shampoo for sensitive scalp according to table 27, where the perfume oil composition 1B is replaced by the same amount of the perfume oil composition 3.

Gloss enhancing shampoo for sensitive scalp according to table 27, where the perfume oil composition 1B is replaced by the same amount of the perfume oil composition 4.

Gloss enhancing shampoo for sensitive scalp according to table 27, where the perfume oil composition 1B is replaced by the same amount of the perfume oil composition 5.

Gloss enhancing shampoo for sensitive scalp according to table 27, where the perfume oil composition 1B is replaced by the same amount of the perfume oil composition 6.

Gloss enhancing shampoo for sensitive scalp according to table 27, where the perfume oil composition 1B is replaced by the same amount of the perfume oil composition 7.

Gloss enhancing shampoo for sensitive scalp according to table 27, where the perfume oil composition 1B is replaced by the same amount of the perfume oil composition 8.

Gloss enhancing shampoo for sensitive scalp according to table 27, where the perfume oil composition 1B is replaced by the same amount of the perfume oil composition 9.

Gloss enhancing shampoo for sensitive scalp according to table 27, where the perfume oil composition 1B is replaced by the same amount of the perfume oil composition 10.

Gloss enhancing shampoo for sensitive scalp according to table 27, where the perfume oil composition 1B is replaced by the same amount of the perfume oil composition 11.

Gloss enhancing shampoo for sensitive scalp according to table 27, where the perfume oil composition 1B is replaced by the same amount of the perfume oil composition 12.

Gloss enhancing shampoo for sensitive scalp according to table 27, where the perfume oil composition 1B is replaced by the same amount of the perfume oil composition 13.

Gloss enhancing shampoo for sensitive scalp according to table 27, where the perfume oil composition 1B is replaced by the same amount of the perfume oil composition 14.

Gloss enhancing shampoo for sensitive scalp according to table 27, where the perfume oil composition 1B is replaced by the same amount of the perfume oil composition 15.

Gloss enhancing shampoo for sensitive scalp according to table 27, where the perfume oil composition 1B is replaced by the same amount of the perfume oil composition 16.

TABLE 28

Deo Stick

| | Ingredients | INCI/Chemistry | % | Function |
|---|---|---|---|---|
| I. | LANETTE ® 18 DEO | Stearyl Alcohol | 18.50 | Consistency factor |
| | CUTINA ® HR POWDER | Hydrogenated Castor Oil | 4.50 | Consistency factor |
| | CUTINA ® CP | Cetyl Palmitate | 25.00 | Emollient |
| | CETIOL ® MM | Myristyl Myristate | 10.00 | Emollient |
| | CETIOL ® RLF | Caprylyl Caprylate/Caprate | 5.00 | Emollient |
| | MYRITOL ® 312 | Caprylic/Capric Triglyceride | 29.30 | Emollient |
| | HYDAGEN ® C.A.T. | Triethyl Citrate | 5.00 | Active, antiperspirant |
| II. | COSMEDIA ® SILC | Silica | 2.00 | Skin feel modifier |
| | PHYTOSOOTHE ™ LS 9766 | *Brassica Campestris* (Rapeseed) Sterols (and) Cetearyl Alcohol | 0.50 | Active ingredient |
| III. | Perfume oil composition 1B | Fragrance | 0.20 | Perfume |

Deo stick according to table 28, where the perfume oil composition 1B is replaced by the same amount of the perfume oil composition 2B.

Deo stick according to table 28, where the perfume oil composition 1B is replaced by the same amount of the perfume oil composition 3.

Deo stick according to table 28, where the perfume oil composition 1B is replaced by the same amount of the perfume oil composition 4.

Deo stick according to table 28, where the perfume oil composition 1B is replaced by the same amount of the perfume oil composition 5.

Deo stick according to table 28, where the perfume oil composition 1B is replaced by the same amount of the perfume oil composition 6.

Deo stick according to table 28, where the perfume oil composition 1B is replaced by the same amount of the perfume oil composition 7.

Deo stick according to table 28, where the perfume oil composition 1B is replaced by the same amount of the perfume oil composition 8.

Deo stick according to table 28, where the perfume oil composition 1B is replaced by the same amount of the perfume oil composition 9.

Deo stick according to table 28, where the perfume oil composition 1B is replaced by the same amount of the perfume oil composition 10.

Deo stick according to table 28, where the perfume oil composition 1B is replaced by the same amount of the perfume oil composition 11.

Deo stick according to table 28, where the perfume oil composition 1B is replaced by the same amount of the perfume oil composition 12.

Deo stick according to table 28, where the perfume oil composition 1B is replaced by the same amount of the perfume oil composition 13.

Deo stick according to table 28, where the perfume oil composition 1B is replaced by the same amount of the perfume oil composition 14.

Deo stick according to table 28, where the perfume oil composition 1B is replaced by the same amount of the perfume oil composition 15.

Deo stick according to table 28, where the perfume oil composition 1B is replaced by the same amount of the perfume oil composition 16.

TABLE 29

Baby Wipe

| | Ingredients | INCI/Chemistry | % | Function |
|---|---|---|---|---|
| I. | Water, demin. | Water | 95.25 | |
| | Sodium Benzoate | Sodium Benzoate | 0.50 | Preservative |
| II. | EMULGADE ® CPE | Vegetable Oil (and) Glycerin (and) Lauryl Glucoside (and) Polyglyceryl-2-Dipolyhydroxystearate (and) Glyceryl Oleate | 4.00 | Emulsion base (O/W) |
| | LIPOFRUCTYL ™ ARGAN LS 9779 | *Argania Spinosa* Kernel Oil | 0.10 | Active ingredient |
| | Perfume oil composition 1B | Fragrance | 0.10 | Perfume |
| III. | Citric Acid (50%) | Citric Acid | 0.15 | Agent, pH adjusting |

Baby wipe according to table 29, where the perfume oil composition 1B is replaced by the same amount of the perfume oil composition 2B.

Baby wipe according to table 29, where the perfume oil composition 1B is replaced by the same amount of the perfume oil composition 3.

Baby wipe according to table 29, where the perfume oil composition 1B is replaced by the same amount of the perfume oil composition 4.

Baby wipe according to table 29, where the perfume oil composition 1B is replaced by the same amount of the perfume oil composition 5.

Baby wipe according to table 29, where the perfume oil composition 1B is replaced by the same amount of the perfume oil composition 6.

Baby wipe according to table 29, where the perfume oil composition 1B is replaced by the same amount of the perfume oil composition 7.

Baby wipe according to table 29, where the perfume oil composition 1B is replaced by the same amount of the perfume oil composition 8.

Baby wipe according to table 29, where the perfume oil composition 1B is replaced by the same amount of the perfume oil composition 9.

Baby wipe according to table 29, where the perfume oil composition 1B is replaced by the same amount of the perfume oil composition 10.

Baby wipe according to table 29, where the perfume oil composition 1B is replaced by the same amount of the perfume oil composition 11.

Baby wipe according to table 29, where the perfume oil composition 1B is replaced by the same amount of the perfume oil composition 12.

Baby wipe according to table 29, where the perfume oil composition 1B is replaced by the same amount of the perfume oil composition 13.

Baby wipe according to table 29, where the perfume oil composition 1B is replaced by the same amount of the perfume oil composition 14.

Baby wipe according to table 29, where the perfume oil composition 1B is replaced by the same amount of the perfume oil composition 15.

Baby wipe according to table 29, where the perfume oil composition 1B is replaced by the same amount of the perfume oil composition 16.

After shave balm according to table 30, where the perfume oil composition 1B is replaced by the same amount of the perfume oil composition 5.

After shave balm according to table 30, where the perfume oil composition 1B is replaced by the same amount of the perfume oil composition 6.

After shave balm according to table 30, where the perfume oil composition 1B is replaced by the same amount of the perfume oil composition 7.

After shave balm according to table 30, where the perfume oil composition 1B is replaced by the same amount of the perfume oil composition 8.

After shave balm according to table 30, where the perfume oil composition 1B is replaced by the same amount of the perfume oil composition 9.

After shave balm according to table 30, where the perfume oil composition 1B is replaced by the same amount of the perfume oil composition 10.

After shave balm according to table 30, where the perfume oil composition 1B is replaced by the same amount of the perfume oil composition 11.

After shave balm according to table 30, where the perfume oil composition 1B is replaced by the same amount of the perfume oil composition 12.

After shave balm according to table 30, where the perfume oil composition 1B is replaced by the same amount of the perfume oil composition 13.

TABLE 30

After shave balm

| | Ingredients | INCI | % | Function |
|---|---|---|---|---|
| I | Myritol ® 331 | Cocoglycerides | 2.50 | Emollient |
| | Cetiol ® Sensoft | Propylheptyl Caprylate | 5.00 | Emollient |
| | Cetiol ® C5 | Coco-Caprylate | 2.50 | Emollient |
| | Cosmedia ® Triple C | Polyquaternium-37 (and) Dicaprylyl Carbonate (and) Lauryl Glucoside | 1.50 | Cationic Polymer |
| II | Deionized Water | Aqua | 84.80 | |
| | Glycerine | Glycerin | 1.00 | Humectant |
| III | Anasensyl ™ LS 9322 | Mannitol (and) Ammonium Glycyrrhizate (and) Caffeine (and) Zinc Gluconate (and) *Aesculus Hippocastanum* Extract | 1.00 | Soothing Active |
| IV | Perfume oil composition 1B | Fragrance | 0.10 | Perfume |
| V | Euxyl PE 9010 (Schülke) | Phenoxyethanol (and) Ethylhexylglycerin | 1.00 | Preservative |
| | Sensiva SC 50 (Schülke) | Ethylhexylglycerin | 0.50 | Preservative |
| VI | NaOH (Aq. Sol. 25%) | Sodium Hydroxide | 0.10 | Neutralizing Agent |

After shave balm according to table 30, where the perfume oil composition 1B is replaced by the same amount of the perfume oil composition 2B.

After shave balm according to table 30, where the perfume oil composition 1B is replaced by the same amount of the perfume oil composition 3.

After shave balm according to table 30, where the perfume oil composition 1B is replaced by the same amount of the perfume oil composition 4.

After shave balm according to table 30, where the perfume oil composition 1B is replaced by the same amount of the perfume oil composition 14.

After shave balm according to table 30, where the perfume oil composition 1B is replaced by the same amount of the perfume oil composition 15.

After shave balm according to table 30, where the perfume oil composition 1B is replaced by the same amount of the perfume oil composition 16.

TABLE 31

Face Gel

| | Ingredients | INCI | % | Function |
|---|---|---|---|---|
| I | Deionized Water | Aqua | 71.65 | |
| | Glycerine | Glycerin | 3.00 | Humectant |
| | EDETA B Powder (BASF) | Tetrasodium EDTA | 0.05 | Complexing Agent |
| II | Cosmedia ® SP | Sodium Polyacrylate | 1.20 | Emulsifying Polymer |
| III | Cegesoft ® PFO | *Passiflora Incarnata* Oil | 2.00 | Emollient |
| | Uvinul MC 80 (BASF) | Ethylhexyl Methoxycinnamate | 2.00 | UVB Filter |
| | KF 96, 100 cs (Shin Etsu) | Dimethicone | 2.00 | Emollient |
| IV | Cetiol ® CC | Dicaprylyl Carbonate | 5.00 | Emollient |
| | Cetiol ® C5 | Coco-Caprylate | 4.00 | Emollient |
| | Uvinul A Plus Granular (BASF) | Diethylamino Hydroxybenzoyl Hexyl Benzoate | 0.50 | UVA Filter |
| | Cegesoft ® SBE | *Butyrospermum Parkii* | 1.50 | Emollient |
| | Eumulgin ® SG | Sodium Stearoyl Glutamate | 0.10 | O/W Emulsifier |
| V | Deionized Water | Aqua | 5.00 | |
| | Skinasensyl ™ PW LS 9852 | Mannitol (and) Sodium Citrate (and) Acetyl Tetrapeptide-15 | 0.30 | Soothing Active |
| VI | Covi-ox ® T70C | Tocopherol | 0.10 | Antioxidant |
| | Perfume oil composition 1B | Fragrance | 0.10 | Perfume |
| VII | Euxyl PE 9010 (Schülke) | Phenoxyethanol (and) Ethylhexylglycerin | 1.00 | Preservative |
| | Sensiva SC 50 (Schülke) | Ethylhexylglycerin | 0.50 | Preservative |

Face gel according to table 31, where the perfume oil composition 1B is replaced by the same amount of the perfume oil composition 2B.

Face gel according to table 31, where the perfume oil composition 1B is replaced by the same amount of the perfume oil composition 3.

Face gel according to table 31, where the perfume oil composition 1B is replaced by the same amount of the perfume oil composition 4.

Face gel according to table 31, where the perfume oil composition 1B is replaced by the same amount of the perfume oil composition 5.

Face gel according to table 31, where the perfume oil composition 1B is replaced by the same amount of the perfume oil composition 6.

Face gel according to table 31, where the perfume oil composition 1B is replaced by the same amount of the perfume oil composition 7.

Face gel according to table 31, where the perfume oil composition 1B is replaced by the same amount of the perfume oil composition 8.

Face gel according to table 31, where the perfume oil composition 1B is replaced by the same amount of the perfume oil composition 9.

Face gel according to table 31, where the perfume oil composition 1B is replaced by the same amount of the perfume oil composition 10.

Face gel according to table 31, where the perfume oil composition 1B is replaced by the same amount of the perfume oil composition 11.

Face gel according to table 31, where the perfume oil composition 1B is replaced by the same amount of the perfume oil composition 12.

Face gel according to table 31, where the perfume oil composition 1B is replaced by the same amount of the perfume oil composition 13.

Face gel according to table 31, where the perfume oil composition 1B is replaced by the same amount of the perfume oil composition 14.

Face gel according to table 31, where the perfume oil composition 1B is replaced by the same amount of the perfume oil composition 15.

Face gel according to table 31, where the perfume oil composition 1B is replaced by the same amount of the perfume oil composition 16.

TABLE 32

Face Day Care Cream

| | Ingredients | INCI | % | Function |
|---|---|---|---|---|
| I | Deionized Water | Aqua | 69.55 | |
| | Glycerine | Glycerin | 3.00 | Humectant |
| | EDETA B Powder (BASF) | Tetrasodium EDTA | 0.05 | Complexing Agent |
| II | Cosmedia ® SP | Sodium Polyacrylate | 0.80 | Emulsifying Polymer |
| III | Emulgade ® PL 68/50 | Cetearyl Glucoside (and) Cetearyl Alcohol | 2.00 | Self-Emulsifying Base |
| | Eumulgin ® SG | Sodium Stearoyl Glutamate | 0.50 | O/W Emulsifier |
| | Monomuls ® 90-O-18 | Glyceryl Oleate | 2.00 | W/O Emulsifier |

TABLE 32-continued

Face Day Care Cream

| | Ingredients | INCI | % | Function |
|---|---|---|---|---|
| | Cutina ® GMS-V | Glyceryl Stearate | 2.00 | Consistency Giving Factor |
| | Cetiol ® Sensoft | Propylheptyl Caprylate | 5.00 | Emollient |
| | Myritol ® 331 | Cocoglycerides | 3.00 | Emollient |
| | Cegesoft ® PFO | *Passiflora Incarnata* Oil | 3.00 | Emollient |
| | Lipodermol ™ LS 8656 | Octyldodecanol (and) Lecithin (and) Arachidyl Propionate (and) Tocopheryl Acetate (and) Retinyl Palmitate (and) Ethyl Linoleate (and) Ethyl Linolenate (and) Ethyl Oleate | 1.00 | Anti-Ageing Active |
| | General ® R | *Brassica Campestris* (Rapeseed) Sterols | 1.00 | Anti-inflammatory Active |
| IV | Sphingoceryl ™ WS LS 9859 | Aqua (and) Glycerin (and) *Helianthus Annuus* Seed Extract (and) Decyl Glucoside | 1.00 | Moisturizing Active |
| | Deionized Water | Aqua | 4.00 | |
| | Perfume oil composition 1B | Fragrance | 0.10 | Perfume |
| V | Covi-ox ® T70C | Tocopherol | 0.50 | Antioxidant |
| VI | Euxyl PE 9010 (Schülke) | Phenoxyethanol (and) Ethylhexylglycerin | 1.00 | Preservative |
| | Sensiva SC 50 (Schülke) | Ethylhexylglycerin | 0.50 | Preservative |

Face day care cream according to table 32, where the perfume oil composition 1B is replaced by the same amount of the perfume oil composition 2B.

Face day care cream according to table 32, where the perfume oil composition 1B is replaced by the same amount of the perfume oil composition 3.

Face day care cream according to table 32, where the perfume oil composition 1B is replaced by the same amount of the perfume oil composition 4.

Face day care cream according to table 32, where the perfume oil composition 1B is replaced by the same amount of the perfume oil composition 5.

Face day care cream according to table 32, where the perfume oil composition 1B is replaced by the same amount of the perfume oil composition 6.

Face day care cream according to table 32, where the perfume oil composition 1B is replaced by the same amount of the perfume oil composition 7.

Face day care cream according to table 32, where the perfume oil composition 1B is replaced by the same amount of the perfume oil composition 8.

Face day care cream according to table 32, where the perfume oil composition 1B is replaced by the same amount of the perfume oil composition 9.

Face day care cream according to table 32, where the perfume oil composition 1B is replaced by the same amount of the perfume oil composition 10.

Face day care cream according to table 32, where the perfume oil composition 1B is replaced by the same amount of the perfume oil composition 11.

Face day care cream according to table 32, where the perfume oil composition 1B is replaced by the same amount of the perfume oil composition 12.

Face day care cream according to table 32, where the perfume oil composition 1B is replaced by the same amount of the perfume oil composition 13.

Face day care cream according to table 32, where the perfume oil composition 1B is replaced by the same amount of the perfume oil composition 14.

Face day care cream according to table 32, where the perfume oil composition 1B is replaced by the same amount of the perfume oil composition 15.

Face day care cream according to table 32, where the perfume oil composition 1B is replaced by the same amount of the perfume oil composition 16.

TABLE 33

Face Cleanser

| | Ingredients | INCI | % | Function |
|---|---|---|---|---|
| I | Deionized Water | Aqua | 80.15 | |
| | EDETA B Powder (BASF) | Tetrasodium EDTA | 0.05 | Complexing Agent |
| | Eumulgin ® SG | Sodium Stearoyl Glutamate | 0.30 | O/W Emulsifier |
| II | Cosmedia ® SP | Sodium Polyacrylate | 1.20 | Emulsifier |
| III | Isopropylpalmitate | Isopropyl palmitate | 5.00 | Emollient |
| | Cetiol ® CC | Dicaprylyl Carbonate | 3.00 | Emollient |
| | Cetiol ® C5 | Coco-Caprylate | 7.00 | Emollient |
| IV | Plantacare ® 818 UP | Coco Glucoside | 0.75 | Non Ionic Surfactant |
| V | Indinyl ® CA LS 8998 | Water (and) *Cassia Angustifolia* Seed Polysaccharide | 0.50 | Smoothing and Moisturizing Active |
| | Perfume oil composition 1B | Fragrance | 0.10 | Perfume |

TABLE 33-continued

Face Cleanser

| | Ingredients | INCI | % | Function |
|---|---|---|---|---|
| VI | Euxyl PE 9010 (Schülke) | Phenoxyethanol (and) Ethylhexylglycerin | 1.00 | Preservative |
| | Sensiva SC 50 (Schülke) | Ethylhexylglycerin | 0.50 | Preservative |
| VII | NaOH (Aq. Sol. 25%) | Sodium Hydroxide | 0.45 | Neutralizing Agent |

Face cleanser according to table 33, where the perfume oil composition 1B is replaced by the same amount of the perfume oil composition 2B.

Face cleanser according to table 33, where the perfume oil composition 1B is replaced by the same amount of the perfume oil composition 3.

Face cleanser according to table 33, where the perfume oil composition 1B is replaced by the same amount of the perfume oil composition 4.

Face cleanser according to table 33, where the perfume oil composition 1B is replaced by the same amount of the perfume oil composition 5.

Face cleanser according to table 33, where the perfume oil composition 1B is replaced by the same amount of the perfume oil composition 6.

Face cleanser according to table 33, where the perfume oil composition 1B is replaced by the same amount of the perfume oil composition 7.

Face cleanser according to table 33, where the perfume oil composition 1B is replaced by the same amount of the perfume oil composition 8.

Face cleanser according to table 33, where the perfume oil composition 1B is replaced by the same amount of the perfume oil composition 9.

Face cleanser according to table 33, where the perfume oil composition 1B is replaced by the same amount of the perfume oil composition 10.

Face cleanser according to table 33, where the perfume oil composition 1B is replaced by the same amount of the perfume oil composition 11.

Face cleanser according to table 33, where the perfume oil composition 1B is replaced by the same amount of the perfume oil composition 12.

Face cleanser according to table 33, where the perfume oil composition 1B is replaced by the same amount of the perfume oil composition 13.

Face cleanser according to table 33, where the perfume oil composition 1B is replaced by the same amount of the perfume oil composition 14.

Face cleanser according to table 33, where the perfume oil composition 1B is replaced by the same amount of the perfume oil composition 15.

Face cleanser according to table 33, where the perfume oil composition 1B is replaced by the same amount of the perfume oil composition 16.

TABLE 34

Sun Care SPF50+, Sprayable Lotion

| | Ingredients | INCI/Chemistry | % | Function |
|---|---|---|---|---|
| I. | DEHYMULS ® PGPH | Polyglyceryl-2 Dipolyhydroxystearate | 4.00 | Emulsifier (W/O) |
| | CETIOL ® B | Dibutyl Adipate | 8.00 | Emollient |
| | MYRITOL ® 331 | Cocoglycerides | 5.00 | Emollient |
| | Tinosorb S (BASF) | Bis-Ethylhexyloxyphenol Methoxyphenyl Triazine | 3.00 | UV filter, UV-A + UV-B |
| | Uvinul T 150 (BASF) | Ethylhexyl Triazone Diethylamino | 2.50 | UV filter, UV-B |
| | Uvinul A Plus (BASF) | Hydroxybenzoyl Hexyl Benzoate | 10.00 | UV filter, UV-A |
| | Uvinul MC 80 (BASF) | Ethylhexyl Methoxycinnamate | 10.00 | UV filter, UV-B |
| | Sensiva SC 50 (Schülke) | Ethylhexylglycerin | 0.50 | Preservative |
| II. | Water, demin. | Water | 45.55 | |
| | Glycerin | Glycerin | 3.00 | Agent, humectant |
| | EDETA BD (BASF) | Disodium EDTA | 0.05 | Chelating agent |
| | Euxyl PE 9010 (Schülke) | Phenoxyethanol, Ethylhexylglycerin | 1.00 | Preservative |
| | Keltrol CG-T (CP Kelco) | Xanthan Gum | 0.10 | Agent, thickening |
| | Veegum Ultra (RT Vanderbilt, Inc.) | Magnesium Aluminum Silicate | 2.00 | Stabilizer |
| III. | PLANTAPON ® LGC SORB | Sodium Lauryl Glucose Carboxylate (and) Lauryl Glucoside | 1.50 | Surfactant |
| IV. | Eusolex T 2000 (Merck) | Titanium Dioxide and Alumina and Simethicone | 3.5 | UV filter, UV-A + UV-B |

TABLE 34-continued

Sun Care SPF50+, Sprayable Lotion

| | Ingredients | INCI/Chemistry | % | Function |
|---|---|---|---|---|
| V. | DN-AGE ™ PW LS 9827 | *Cassia Alata* Leaf Extract (and) Maltodextrin | 0.10 | Active ingredient |
| | Perfume oil composition 1B | Fragrance | 0.20 | Perfume |

Sun Care SPF50+, sprayable lotion according to table 34, where the perfume oil composition 1B is replaced by the same amount of the perfume oil composition 2B.

Sun Care SPF50+, sprayable lotion according to table 34, where the perfume oil composition 1B is replaced by the same amount of the perfume oil composition 3.

Sun Care SPF50+, sprayable lotion according to table 34, where the perfume oil composition 1B is replaced by the same amount of the perfume oil composition 4.

Sun Care SPF50+, sprayable lotion according to table 34, where the perfume oil composition 1B is replaced by the same amount of the perfume oil composition 5.

Sun Care SPF50+, sprayable lotion according to table 34, where the perfume oil composition 1B is replaced by the same amount of the perfume oil composition 6.

Sun Care SPF50+, sprayable lotion according to table 34, where the perfume oil composition 1B is replaced by the same amount of the perfume oil composition 7.

Sun Care SPF50+, sprayable lotion according to table 34, where the perfume oil composition 1B is replaced by the same amount of the perfume oil composition 8.

Sun Care SPF50+, sprayable lotion according to table 34, where the perfume oil composition 1B is replaced by the same amount of the perfume oil composition 9.

Sun Care SPF50+, sprayable lotion according to table 34, where the perfume oil composition 1B is replaced by the same amount of the perfume oil composition 10.

Sun Care SPF50+, sprayable lotion according to table 34, where the perfume oil composition 1B is replaced by the same amount of the perfume oil composition 11.

Sun Care SPF50+, sprayable lotion according to table 34, where the perfume oil composition 1B is replaced by the same amount of the perfume oil composition 12.

Sun Care SPF50+, sprayable lotion according to table 34, where the perfume oil composition 1B is replaced by the same amount of the perfume oil composition 13.

Sun Care SPF50+, sprayable lotion according to table 34, where the perfume oil composition 1B is replaced by the same amount of the perfume oil composition 14.

Sun Care SPF50+, sprayable lotion according to table 34, where the perfume oil composition 1B is replaced by the same amount of the perfume oil composition 15.

Sun Care SPF50+, sprayable lotion according to table 34, where the perfume oil composition 1B is replaced by the same amount of the perfume oil composition 16.

TABLE 35

Hand dish cleaner, regular
Hand dish cleaner, regular

| Component | INCI | amount % |
|---|---|---|
| Lutensit ® A-LBN 50 | Benzenesulfonic acid, C10-13-alkyl derivs., sodium salts | 25 |
| Lutensol ® GD 70 | Alkyl polyglucoside | 3 |
| Lutensol ® A 7 N | Fatty alcohol ethoxylate | 2 |
| Perfume oil composition 1B | Fragrance | 0.7 |
| Dyes | Dye | 0.05 |
| Water, de ionized | Aqua | ad 100 |

Hand dish cleaner according to table 35, where the perfume oil composition 1B is replaced by the same amount of the perfume oil composition 2B.

Hand dish cleaner according to table 35, where the perfume oil composition 1B is replaced by the same amount of the perfume oil composition 3.

Hand dish cleaner according to table 35, where the perfume oil composition 1B is replaced by the same amount of the perfume oil composition 4.

Hand dish cleaner according to table 35, where the perfume oil composition 1B is replaced by the same amount of the perfume oil composition 5.

Hand dish cleaner according to table 35, where the perfume oil composition 1B is replaced by the same amount of the perfume oil composition 6.

Hand dish cleaner according to table 35, where the perfume oil composition 1B is replaced by the same amount of the perfume oil composition 7.

Hand dish cleaner according to table 35, where the perfume oil composition 1B is replaced by the same amount of the perfume oil composition 8.

Hand dish cleaner according to table 35, where the perfume oil composition 1B is replaced by the same amount of the perfume oil composition 9.

Hand dish cleaner according to table 35, where the perfume oil composition 1B is replaced by the same amount of the perfume oil composition 10.

Hand dish cleaner according to table 35, where the perfume oil composition 1B is replaced by the same amount of the perfume oil composition 11.

Hand dish cleaner according to table 35, where the perfume oil composition 1B is replaced by the same amount of the perfume oil composition 12.

Hand dish cleaner according to table 35, where the perfume oil composition 1B is replaced by the same amount of the perfume oil composition 13.

Hand dish cleaner according to table 35, where the perfume oil composition 1B is replaced by the same amount of the perfume oil composition 14.

Hand dish cleaner according to table 35, where the perfume oil composition 1B is replaced by the same amount of the perfume oil composition 15.

Hand dish cleaner according to table 35, where the perfume oil composition 1B is replaced by the same amount of the perfume oil composition 16.

TABLE 36

Body lotion

| | Ingredients | INCI | % | Function |
|---|---|---|---|---|
| I | Eumulgin ® SG | Sodium Stearoyl Glutamate | 0.40 | O/W Emulsifier |
| | Cutina ® GMS-V | Glyceryl Stearate | 1.50 | Consistency Giving Factor |
| | Cetiol ® SB 45 | *Butyrospermum Parkii* (Shea) Butter | 3.00 | Emollient |
| | Cetiol ® C5 | Coco-Caprylate | 2.00 | Emollient |
| | Irwinol ™ LS 9890 | Octyldodecanol (and) *Irvingia Gabonensis* (and) Hydrogenated Coco-Glycerides | 1.00 | Moisturizing Active |
| II | Water, demin. | Aqua | 86.77 | |
| | Glycerine | Glycerin | 3.00 | Humectant |
| | EDETA B Powder (BASF) | Tetrasodium EDTA | 0.05 | Complexing Agent |
| III | Rheocare ™ C Plus | Carbomer | 0.35 | Thickener |
| IV | NaOH (Aq sol. 25%) | Sodium Hydroxide | 0.10 | Neutralizing Agent |
| V | Covi-ox ® T70C | Tocopherol | 0.05 | Antioxidant |
| | Perfume oil composition 1B | Fragrance | 0.10 | Perfume |
| VI | Euxyl PE 9010 (Schülke) | Phenoxyethanol (and) Ethylhexylglycerin | 1.00 | Preservative |
| | Sensiva SC50 (Schülke) | Ethylhexylglycerin | 0.50 | Preservative |
| VII | NaOH (Aq sol. 25%) | Sodium Hydroxide | 0.18 | Neutralizing Agent |

Body lotion according to table 36, where the perfume oil composition 1B is replaced by the same amount of the perfume oil composition 2B.

Body lotion according to table 36, where the perfume oil composition 1B is replaced by the same amount of the perfume oil composition 3.

Body lotion according to table 36, where the perfume oil composition 1B is replaced by the same amount of the perfume oil composition 4.

Body lotion according to table 36, where the perfume oil composition 1B is replaced by the same amount of the perfume oil composition 5.

Body lotion according to table 36, where the perfume oil composition 1B is replaced by the same amount of the perfume oil composition 6.

Body lotion according to table 36, where the perfume oil composition 1B is replaced by the same amount of the perfume oil composition 7.

Body lotion according to table 36, where the perfume oil composition 1B is replaced by the same amount of the perfume oil composition 8.

Body lotion according to table 36, where the perfume oil composition 1B is replaced by the same amount of the perfume oil composition 9.

Body lotion according to table 36, where the perfume oil composition 1B is replaced by the same amount of the perfume oil composition 10.

Body lotion according to table 36, where the perfume oil composition 1B is replaced by the same amount of the perfume oil composition 11.

Body lotion according to table 36, where the perfume oil composition 1B is replaced by the same amount of the perfume oil composition 12.

Body lotion according to table 36, where the perfume oil composition 1B is replaced by the same amount of the perfume oil composition 13.

Body lotion according to table 36, where the perfume oil composition 1B is replaced by the same amount of the perfume oil composition 14.

Body lotion according to table 36, where the perfume oil composition 1B is replaced by the same amount of the perfume oil composition 15.

Body lotion according to table 36, where the perfume oil composition 1B is replaced by the same amount of the perfume oil composition 16.

TABLE 37

Hand dish cleaner, concentrate: Hand dish cleaner, concentrate

| Component | INCI | amount % |
|---|---|---|
| Lutensit ® A-LBN 50 | Benzenesulfonic acid, C10-13-alkyl derivs., sodium salts | 40 |
| Lutensit ® AS 2230 | Alkylether sulphate | 25 |
| Lutensol ® GD 70 | Alkyl polyglucoside | 7 |
| Lutensol ® A 7 N | Fatty alcohol ethoxylate | 4 |
| Perfume oil composition 1B | Perfume | 1 |
| Dyes | Dye | 0.05 |
| Water, de ionized | Aqua | ad 100 |

Hand dish cleaner according to table 37, where the perfume oil composition 1B is replaced by the same amount of the perfume oil composition 2B.

Hand dish cleaner according to table 37, where the perfume oil composition 1B is replaced by the same amount of the perfume oil composition 3.

Hand dish cleaner according to table 37, where the perfume oil composition 1B is replaced by the same amount of the perfume oil composition 4.

Hand dish cleaner according to table 37, where the perfume oil composition 1B is replaced by the same amount of the perfume oil composition 5.

Hand dish cleaner according to table 37, where the perfume oil composition 1B is replaced by the same amount of the perfume oil composition 6.

Hand dish cleaner according to table 37, where the perfume oil composition 1 is replaced by the same amount of the perfume oil composition 7.

Hand dish cleaner according to table 37, where the perfume oil composition 1B is replaced by the same amount of the perfume oil composition 8.

Hand dish cleaner according to table 37, where the perfume oil composition 1B is replaced by the same amount of the perfume oil composition 9.

Hand dish cleaner according to table 37, where the perfume oil composition 1B is replaced by the same amount of the perfume oil composition 10.

Hand dish cleaner according to table 37, where the perfume oil composition 1B is replaced by the same amount of the perfume oil composition 11.

Hand dish cleaner according to table 37, where the perfume oil composition 1B is replaced by the same amount of the perfume oil composition 12.

Hand dish cleaner according to table 37, where the perfume oil composition 1B is replaced by the same amount of the perfume oil composition 13.

Hand dish cleaner according to table 37, where the perfume oil composition 1B is replaced by the same amount of the perfume oil composition 14.

Hand dish cleaner according to table 37, where the perfume oil composition 1B is replaced by the same amount of the perfume oil composition 15.

Hand dish cleaner according to table 37, where the perfume oil composition 1B is replaced by the same amount of the perfume oil composition 16.

TABLE 38

Sanitary cleaner, concentrate
Sanitary cleaner, concentrate

| Component | INCI | amount % |
| --- | --- | --- |
| Lutensol ® TO 8 | isotridecanolethoxylate | 5 |
| Phosphoric acid | Phosphoric acid | 20 |
| Korantin ® PM | 2-propyn-1-ol, ethoxylated | 3 |
| Citric acid | Citric acid | 3 |
| Perfume oil composition 1B | Fragrance | 1 |
| Water, deionized | Aqua | ad 100 |

Sanitary cleaner according to table 38, where the perfume oil composition 1B is replaced by the same amount of the perfume oil composition 2B.

Sanitary cleaner according to table 38, where the perfume oil composition 1B is replaced by the same amount of the perfume oil composition 3.

Sanitary cleaner according to table 38, where the perfume oil composition 1B is replaced by the same amount of the perfume oil composition 4.

Sanitary cleaner according to table 38, where the perfume oil composition 1B is replaced by the same amount of the perfume oil composition 5.

Sanitary cleaner according to table 38, where the perfume oil composition 1B is replaced by the same amount of the perfume oil composition 6.

Sanitary cleaner according to table 38, where the perfume oil composition 1B is replaced by the same amount of the perfume oil composition 7.

Sanitary cleaner according to table 38, where the perfume oil composition 1B is replaced by the same amount of the perfume oil composition 8.

Sanitary cleaner according to table 38, where the perfume oil composition 1B is replaced by the same amount of the perfume oil composition 9.

Sanitary cleaner according to table 38, where the perfume oil composition 1B is replaced by the same amount of the perfume oil composition 10.

Sanitary cleaner according to table 38, where the perfume oil composition 1B is replaced by the same amount of the perfume oil composition 11.

Sanitary cleaner according to table 38, where the perfume oil composition 1B is replaced by the same amount of the perfume oil composition 12.

Sanitary cleaner according to table 38, where the perfume oil composition 1B is replaced by the same amount of the perfume oil composition 13.

Sanitary cleaner according to table 38, where the perfume oil composition 1B is replaced by the same amount of the perfume oil composition 14.

Sanitary cleaner according to table 38, where the perfume oil composition 1B is replaced by the same amount of the perfume oil composition 15.

Sanitary cleaner according to table 38, where the perfume oil composition 1B is replaced by the same amount of the perfume oil composition 16.

TABLE 39

All purpose cleaner
All purpose cleaner

| Component | INCI | amount % |
| --- | --- | --- |
| Lutensit ® A LBA | Benzenesulfonic acid, 4-C10-13-sec-alkyl derivs | 1 |
| Ammonia | Ammonia | 0.2 |
| Lutensol ® CS 6250 | Hexan-1-ol, ethoxylated | 3 |
| Trilon ® A | trisodium nitrilotriacetate | 1 |
| Citric acid | Citric acid | 0.65 |
| Ethanol | Ethanol | 5 |
| Perfume oil composition 1B | Perfume | 0.5 |
| Water, de ionized | Aqua | ad 100 |

All purpose cleaner according to table 39, where the perfume oil composition 1B is replaced by the same amount of the perfume oil composition 2B.

All purpose cleaner according to table 39, where the perfume oil composition 1B is replaced by the same amount of the perfume oil composition 3.

All purpose cleaner according to table 39, where the perfume oil composition 1B is replaced by the same amount of the perfume oil composition 4.

All purpose cleaner according to table 39, where the perfume oil composition 1B is replaced by the same amount of the perfume oil composition 5.

All purpose cleaner according to table 39, where the perfume oil composition 1B is replaced by the same amount of the perfume oil composition 6.

All purpose cleaner according to table 39, where the perfume oil composition 1B is replaced by the same amount of the perfume oil composition 7.

All purpose cleaner according to table 39, where the perfume oil composition 1B is replaced by the same amount of the perfume oil composition 8.

All purpose cleaner according to table 39, where the perfume oil composition 1B is replaced by the same amount of the perfume oil composition 9.

All purpose cleaner according to table 39, where the perfume oil composition 1B is replaced by the same amount of the perfume oil composition 10.

All purpose cleaner according to table 39, where the perfume oil composition 1B is replaced by the same amount of the perfume oil composition 11.

All purpose cleaner according to table 39, where the perfume oil composition 1B is replaced by the same amount of the perfume oil composition 12.

All purpose cleaner according to table 39, where the perfume oil composition 1B is replaced by the same amount of the perfume oil composition 13.

All purpose cleaner according to table 39, where the perfume oil composition 1B is replaced by the same amount of the perfume oil composition 14.

All purpose cleaner according to table 39, where the perfume oil composition 1B is replaced by the same amount of the perfume oil composition 15.

All purpose cleaner according to table 39, where the perfume oil composition 1B is replaced by the same amount of the perfume oil composition 16.

TABLE 40

Anti bacterial fabric softener
Anti-bacterial fabric softener

| Component | INCI | amount % |
|---|---|---|
| Tinosan ® HP 100 | Hydroxydichlordiphenyl ether | 0.3 |
| Dehyquat AU-46 | Esterquat | 4 |
| Lutensol ® AO 7 | Alcohols, C13-15, ethoxylated | 0.5 |
| Perfume oil composition 1B | Fragrance | 0.5 |
| Water, deionized | Aqua | ad 100 |

Anti bacterial fabric softener according to table 40, where the perfume oil composition 1B is replaced by the same amount of the perfume oil composition 2B.

Anti bacterial fabric softener according to table 40, where the perfume oil composition 1B is replaced by the same amount of the perfume oil composition 3.

Anti bacterial fabric softener according to table 40, where the perfume oil composition 1B is replaced by the same amount of the perfume oil composition 4.

Anti bacterial fabric softener according to table 40, where the perfume oil composition 1B is replaced by the same amount of the perfume oil composition 5.

Anti bacterial fabric softener according to table 40, where the perfume oil composition 1B is replaced by the same amount of the perfume oil composition 6.

Anti bacterial fabric softener according to table 40, where the perfume oil composition 1B is replaced by the same amount of the perfume oil composition 7.

Anti bacterial fabric softener according to table 40, where the perfume oil composition 1B is replaced by the same amount of the perfume oil composition 8.

Anti bacterial fabric softener according to table 40, where the perfume oil composition 1B is replaced by the same amount of the perfume oil composition 9.

Anti bacterial fabric softener according to table 40, where the perfume oil composition 1B is replaced by the same amount of the perfume oil composition 10.

Anti bacterial fabric softener according to table 40, where the perfume oil composition 1B is replaced by the same amount of the perfume oil composition 11.

Anti bacterial fabric softener according to table 40, where the perfume oil composition 1B is replaced by the same amount of the perfume oil composition 12.

Anti bacterial fabric softener according to table 40, where the perfume oil composition 1B is replaced by the same amount of the perfume oil composition 13.

Anti bacterial fabric softener according to table 40, where the perfume oil composition 1B is replaced by the same amount of the perfume oil composition 14.

Anti bacterial fabric softener according to table 40, where the perfume oil composition 1B is replaced by the same amount of the perfume oil composition 15.

Anti bacterial fabric softener according to table 40, where the perfume oil composition 1B is replaced by the same amount of the perfume oil composition 16.

The invention claimed is:

1. A compound selected from a compound of the formula (I.a)

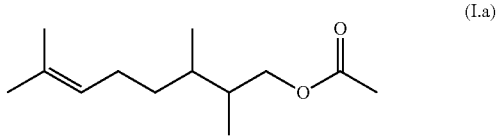

a stereo isomer thereof and mixtures thereof.

2. The compounds according to claim 1, selected from the compounds of formulae (I.a1), (I.a2), (I.a3), (I.a4) and mixtures thereof

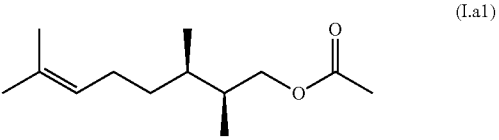

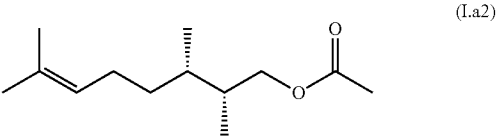

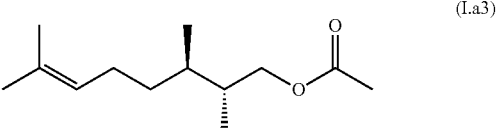

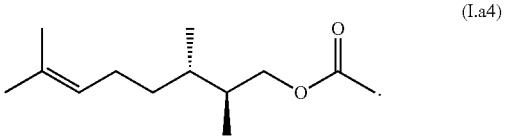

3. A composition comprising at least two compounds selected from the compound of the formula (I.a1), (I.a2), (I.a3) and (I.a4) as in claim 2.

4. A composition comprising at least one compound selected from the compound of the formula (I.a1), (I.a2), (I.a3) and (I.a4) of claim 2 and at least one compound selected from the compound of the formula (I.b1) and (I.b2)

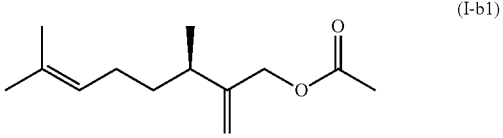

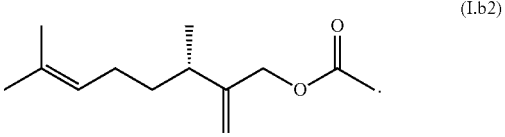

5. The composition according to claim 4, wherein one compound (I.b1) or (I.b2) is present in an amount of at least 60% by weight, based on the total weight of compound (I.b1) and (I.b2).

6. A method for preparing a compound of the formula (I.a),

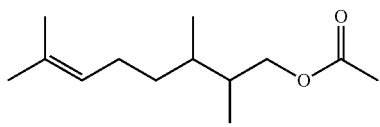
(I.a)

comprising the steps of
a) providing a compound of the formula (II.a),

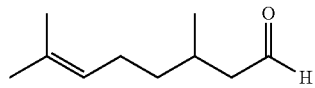
(II.a)

b) subjecting the compound of the formula (II.a) to an aldol condensation reaction with formaldehyde to obtain a compound of the formula (II.b)

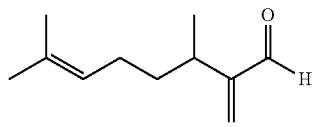
(II.b)

c11) subjecting the compound of the formula (II.b) obtained in step b) to a hydrogenation reaction to obtain a compound of the formula (II.c)

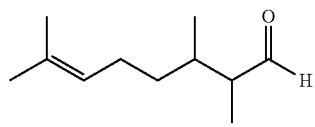
(II.c)

c12) reacting the compound of the formula (II.c) with a reducing agent to obtain a compound of the formula (II.d)

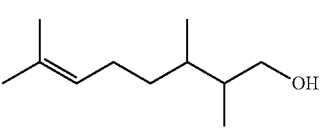
(II.d)

c13) subjecting the compound of the formula (II.d) to an esterification reaction using ethenone to obtain the compound of the formula (I.a).

7. A method for preparing a compound of the formula (I.b),

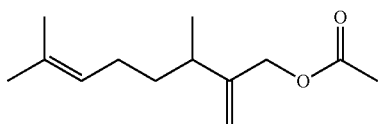
(I.b)

comprising the steps of
a) providing a compound of the formula (II.a),

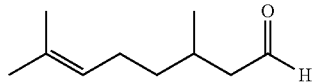
(II.a)

b) subjecting the compound of the formula (II.a) to an aldol condensation reaction formaldehyde to obtain a compound of the formula (II.b)

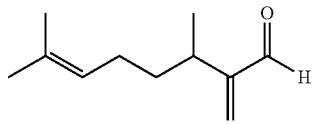
(II.b)

c21) reacting the compound of the formula (II.b) obtained in step b) with a reducing reaction to obtain a compound of the formula (II.e),

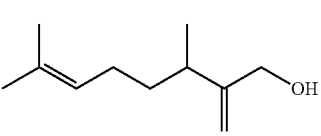
(II.e)

c22) subjecting the compound of the formula (II.e) to an esterification reaction using ethenone to obtain the compound of the formula (I.b).

8. A method for aromatizing a composition, comprising incorporating the compound of the formula (I.a) according to claim 1 in said composition.

9. The method according to claim 8,
for preparing a fragrance and/or aroma having a note of herbaceous, green, technical, natural, fresh impression, floral, freesia, watery, sweet, pleasantly fresh and/or watery-ozone.

10. A method for aromatizing a composition, comprising incorporating into the composition at least two compounds selected from compounds of the formulae (II.a), (II.b), (II.c), (II.d), and (II.e),

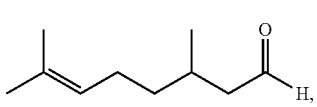
(II.a)

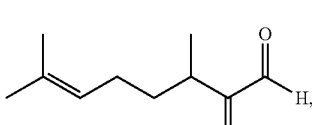
(II.b)

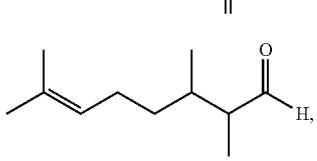
(II.c)

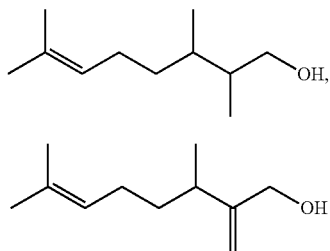

11. The method according to claim 10, wherein
i) the compound of formula (II.b) is used for preparing a fragrance and/or aroma having a note of citrus, and/or
ii) the compound of formula (II.c) is used for preparing a fragrance and/or aroma having a note of rosy, citrus, waxy, and/or
iii) the compound of formula (II.d) is used for preparing a fragrance and/or aroma having a note of rose, geranium, honey, room-filling, good overall impression, fatty, green, woody, and/or herbaceous, and/or
iv) the compound of formula (II.e) is used for preparing a fragrance and/or aroma having a note of rose.

12. The method according to claim 8 wherein the composition is selected from the group consisting of perfumes, detergents, cleaning compositions, cosmetic agents, body care agents, hygiene articles, products for oral and dental hygiene, scent dispensers, fragrances and pharmaceutical agents.

13. An aroma substance and/or fragrance composition comprising
i) at least a compound of the formula (I.a) according to claim 1,
ii) optionally at least one further aroma chemical different from the component i), and
iii) optionally at least one diluent,
with the proviso that the composition comprises at least one component ii) or iii).

14. A perfumed or fragranced product comprising at least a compound of the formula (I.a) according to claim 1.

15. A method for scenting a product, particularly for imparting and/or enhancing an odor or flavor, in which at least one compound of the formula (I.a) according to claim 1 is used.

16. The method according to claim 15,
i) in which at least one compound selected from the compound of formula (I.a) is used for preparing a fragrance and/or aroma having a note of herbaceous, green, technical, natural, fresh impression, floral, freesia, watery, sweet, pleasantly fresh, and/or watery-ozone.

17. A method for aromatizing a composition, comprising incorporating the composition according to claim 3 into the composition to be aromatized.

18. A method for aromatizing a composition, comprising incorporating the composition according to claim 4 into the composition to be aromatized.

19. An aroma substance and/or fragrance composition comprising
i) a composition according to claim 3,
ii) optionally at least one further aroma chemical different from component i), and
iii) optionally at least one diluent,
with the proviso that the composition comprises at least one component ii) or iii).

20. An aroma substance and/or fragrance composition comprising
i) a composition according to claim 4,
ii) optionally at least one further aroma chemical different from the component i), and
iii) optionally at least one diluent,
with the proviso that the composition comprises at least one component ii) or iii).

* * * * *